US008513423B2

(12) United States Patent
Connolly et al.

(10) Patent No.: US 8,513,423 B2
(45) Date of Patent: Aug. 20, 2013

(54) PIPERIDIN-4-YL-AZETIDINE DIAMIDES AS MONOACYLGLYCEROL LIPASE INHIBITORS

(75) Inventors: Peter J. Connolly, New Providence, NJ (US); Haiyan Bian, Princeton, NJ (US); Xun Li, New Hope, PA (US); Li Liu, Germantown, MD (US); Mark J. Macielag, Gwynedd Valley, PA (US); Mark E. McDonnell, Lansdale, PA (US)

(73) Assignee: Janssen Pharmaceutica, NV (BE)

( * ) Notice: Subject to any disclaimer, the term of this patent is extended or adjusted under 35 U.S.C. 154(b) by 0 days.

(21) Appl. No.: 13/277,702

(22) Filed: Oct. 20, 2011

(65) Prior Publication Data
US 2013/0102584 A1 Apr. 25, 2013

Related U.S. Application Data

(60) Provisional application No. 61/405,876, filed on Oct. 22, 2010.

(51) Int. Cl.
*C07D 401/00* (2006.01)
*A61K 31/00* (2006.01)

(52) U.S. Cl.
USPC ..................................... 546/208; 514/210.18

(58) Field of Classification Search
USPC ..................................... 546/208; 514/210.18
See application file for complete search history.

(56) References Cited

U.S. PATENT DOCUMENTS

| 7,217,705 | B2 | 5/2007 | Benavides et al. |
| 7,863,279 | B2 | 1/2011 | Even et al. |
| 2003/0119810 | A1 | 6/2003 | Achard et al. |
| 2004/0167224 | A1 | 8/2004 | Ozaki et al. |
| 2006/0148844 | A1 | 7/2006 | Nakade et al. |
| 2007/0142394 | A1 | 6/2007 | Solomon et al. |
| 2007/0197654 | A1 | 8/2007 | Benavides et al. |
| 2007/0293496 | A1 | 12/2007 | Ozaki et al. |
| 2009/0269785 | A1 | 10/2009 | Schubert et al. |
| 2010/0041651 | A1 | 2/2010 | Even et al. |
| 2010/0324011 | A1 | 12/2010 | Bian et al. |
| 2010/0324012 | A1 | 12/2010 | Bian et al. |
| 2010/0324013 | A1 | 12/2010 | Bian et al. |
| 2010/0324014 | A1 | 12/2010 | Bian et al. |
| 2010/0324015 | A1 | 12/2010 | Chevalier et al. |
| 2010/0324016 | A1 | 12/2010 | Flores et al. |
| 2010/0331299 | A1 | 12/2010 | Bian et al. |
| 2010/0331300 | A1 | 12/2010 | Bian et al. |
| 2011/0015170 | A1 | 1/2011 | Bian et al. |
| 2011/0015171 | A1 | 1/2011 | Bian et al. |
| 2011/0071162 | A1 | 3/2011 | Even et al. |

FOREIGN PATENT DOCUMENTS

| EP | 2180048 A1 | 4/2010 |
| FR | 2915199 A1 | 10/2008 |
| WO | WO 98/37077 A1 | 8/1998 |
| WO | WO 99/19297 A1 | 4/1999 |
| WO | WO 00/63168 A1 | 10/2000 |
| WO | WO 01/77101 A1 | 10/2001 |
| WO | 03/020314 A1 | 3/2003 |
| WO | 2004/056800 A1 | 7/2004 |
| WO | 2006/097175 A1 | 9/2006 |
| WO | 2008/025736 A1 | 3/2008 |
| WO | 2008/145842 A2 | 12/2008 |
| WO | WO 2008/145843 A1 | 12/2008 |
| WO | 2009/132267 A1 | 10/2009 |
| WO | 2010/124121 A1 | 10/2010 |
| WO | WO 2010/124082 A1 | 10/2010 |

OTHER PUBLICATIONS

Benito et al., "Cannabinoid CB2 receptors in human braininflammation.", *Brit. J. Pharmacol.*, 2008, pp. 277-285, vol. 153.
Bennett et al., "A peripheral mononeuropathy in rat that produces disorders of pain sensation like those seen in man.", *Pain*, 1988, pp. 87-107, vol. 33(1).
Ben-Shabat et al., "An entourage effect: inactive endogenous fatty acid glycerol esters enhance 2-arachidonoyl-glycerol cannabinoid activity.", *Eur. J. Pharmacol.*, 1998, pp. 23-31, vol. 353.
Cavuoto et al.,"The expression of receptors for endocannabinoids in human and rodent skeletal muscle.", *Biochem. Biophys. Res. Commun.*, 2007, pp. 105-110, vol. 364.
Comelli et al., "The inhibition of monoacylglycerol lipase by URB602 showed an anti-inflammatory and anti-nociceptive effect in a murine model of acute inflammation.", *Brit. J. Pharmacol.*, 2007, pp. 787-794, vol. 152.
Cravatt et al.,"The Endogenous Cannabinoid System and Its Role in Nociceptive Behavior.", *J. Neurobiol.*, 2004, pp. 149-160, vol. 61.
Devane et al., "Isolation and Structure of a Brain Constituent That Binds to the Cannabinoid Receptor.", *Science*, 1992, pp. 1946-1969, vol. 258.
Di Marzo et al., "Endocannabinoids and the Regulation of their levels in Health and Disease.", *Curr. Opin. Lipidol.*, 2007, pp. 129-140, vol. 18.
Di Marzo et al., "Endocannabinoids: New Targets for Drug Development.", *Curr. Pharm. Des.*, 2000, pp. 1361-1380, vol. 6.
Dogrul et al., "Knock-down' of spinal CB1 receptors produces abnormal pain and elevates spinal dynorphin content in mice.", *Pain*, 2002, pp. 203-209, vol. 100.
Guindon et al.,"Cannabinoid CB2 receptors: a therapeutic target for the treatment of inflammatory and neuropathic pain.", *Brit. J. Pharmacol.*, 2008, pp. 319-334, vol. 153.

(Continued)

*Primary Examiner* — John Mabry

(57) ABSTRACT

Disclosed are compounds, compositions and methods for treating various diseases, syndromes, conditions and disorders, including pain. Such compounds, and enantiomers, diastereomers, and pharmaceutically acceptable salts thereof, are represented by Formula (I) as follows:

wherein Y, Z, and R are defined herein.

16 Claims, No Drawings

(56) References Cited

OTHER PUBLICATIONS

Hajrasouliha et al., "Endogenous cannabinoids contribute to remote ischemic preconditioning via cannabinoid CB2 receptors in the rat heart.", *Eur. J. Pharmacol.*, 2008, pp. 246-252, vol. 579.

Jhaveri et al., "Endocannabinoid metabolism and uptake: novel targets for neuropathic and inflammatory pain.", *Brit. J. Pharmacol.*, 2007, pp. 624-632, vol. 152.

Kathuria et al., "Modulation of anxiety through blockade of anandamide hydrolysis.", *Nat. Med.*, 2003, pp. 76-81, vol. 9.

Lichtman et al., "Pharmacological Activity of Fatty Acid Amides Is Regulated, but Not Mediated, by Fatty Acid Amide Hydrolase in Vivo.", *J. Pharmacol. Exp. Ther.*, 2002, pp. 73-79, vol. 302(1).

Lichtman et al., "Mice lacking fatty acid amide hydrolase exhibit a cannabinoid receptor-mediated phenotypic hypoalgesia.", *Pain*, 2004, pp. 319-327, vol. 109.

Matsuda et al., "Structure of a Cannabinoid Receptor and Functional Expression of the cloned cDNA.", *Nature*, 1990, pp. 561-564, vol. 346.

Matulis et al., "Thermodynamic Stability of Carbonic Anhydrase: Measurements of Binding Affinity and Stoichiometry Using ThermoFluor.", *Biochemistry*, 2005, pp. 5258-5266, vol. 44.

McCarberg et al., "The Future of Cannabinoids as Analgesic Agents: A Pharmacologic, Pharmacokinetic, and Pharmacodynamic Overview.", *Amer. J. Ther.*, 2007, pp. 475-483, vol. 14.

Mechoulam et al., "Identification of an Endogenous 2-Monoglyceride, Present in Canine Gut, that Binds to Cannabinoid Receptors.", *Biochem. Pharmacol.*, 1995, pp. 83-90, vol. 50.

Munro et al., "Molecular Characterization of a Peripheral Receptor for Cannabinoids.", *Nature*, 1993, pp. 61-665, vol. 365.

Njie et al., "Aqueous humor outflow effects of 2-arachidonylglycerol.", *Exp. Eye Res.*, 2008, pp. 106-114, vol. 87(2).

Pacher et al., "Pleiotropic effects of the $CB_2$ cannabinoid receptor activation on human monocyte migration: implications for atherosclerosis and inflammatory diseases.", *Amer J Physiol*, 2008, pp. H1133-H1134, vol. 294.

Pantoliano et al., "High Density Miniaturized Thermal Shift Assays as a General Strategy for Drug Discovery*.", *Journal of Biomolecular Screening*, 2001, pp. 429-440, vol. 6(6).

Pertwee, R.G.,"The diverse CB1 and CB2 receptor pharmacology of three plant cannabinoids: $D^9$-tetrahydrocannabinol, cannabidiol and $D^9$-tetrahydrocannabivarin.", *Brit. J. Pharmacol.*, 2008, pp. 199-215, vol. 153.

Piomelli D., "The Molecular Logic of Endocannabinoid Signalling.", *Nat. Rev. Neurosci.*, 2003, pp. 873-884, vol. 4.

Sugiura et al., "2-Arachidonoylglycerol: A Possible Endogenous Cannabinoid Receptor Ligand in Brain.", *Biochem. Biophys. Res. Commun.*, 1995, pp. 89-97, vol. 215.

Walker et al., "Pain modulation by release of the endogenous cannabinoid anandamide.", *Proc. Natl. Acad. Sci.*, USA, 1999, pp. 12198-121203, vol. 96.

Database Registry, Chemical Abstracts Service, Columbus, Ohio, US; Nov. 3, 2010; WuXi AppTec Co., Ltd.; XP002666746.

International Search Report relating to International application No. PCT/US2011/057085, which corresponds to U.S. Appl. No. 13/277,702. Date of Mailing of International Search Report: Jan. 27, 2012.

Written Opinion of the International Searching Authority relating to International application No. PCT/US2011/057085, which corresponds to U.S. Appl. No. 13/277,702. Date of Mailing of Written Opinion: Jan. 27, 2012.

Chaplan et al., "Quantitative assessment of tactile allodynia in the rat paw.", J. Neurosci Methods, 1994, vol. 53(1), pp. 55-63.

Dixon, W. J., "Efficient analysis of experimental observations.", Annu. Rev. Pharmacol. Toxicol., 1980, vol. 20, pp. 441-462.

Schlosser et al., "In Search in Simplicity and Flexibility: A Rational Access to Twelve Fluoroindolecarboxylic Acids.", Eur. J. Org. Chem. 2006, pp. 2956.

International Search Report and Written Opinion, PCT/US2010/032045, dated Jun. 11, 2010.

International Search Report and Written Opinion, PCT/US2010/032049, dated Jun. 15, 2010.

International Search Report and Written Opinion, PCT/US2010/032068, dated Jun. 14, 2010.

International Search Report and Written Opinion, PCT/US2010/032082, dated Jun. 15, 2010.

International Search Report and Written Opinion, PCT/US2010/032086, dated Jun. 14, 2010.

International Search Report and Written Opinion, PCT/US2010/032089, dated Jun. 14, 2010.

International Search Report and Written Opinion, PCT/US2010/032092, dated Jun. 15, 2010.

International Search Report and Written Opinion, PCT/US2010/032095, dated Jun. 14, 2010.

International Search Report and Written Opinion, PCT/US2010/032098, dated Jun. 18, 2010.

International Search Report and Written Opinion, PCT/US2010/032100, dated Jun. 15, 2010.

International Search Report and Written Opinion, PCT/US2011/049885, dated Oct. 6, 2011.

International Search Report and Written Opinion, PCT/US2011/053442, dated Dec. 23, 2011.

International Search Report and Written Opinion, PCT/US2011/057090, dated Jan. 27, 2012.

International Search Report and Written Opinion, PCT/US2011/057085, dated Jan. 27, 2012.

PIPERIDIN-4-YL-AZETIDINE DIAMIDES AS MONOACYLGLYCEROL LIPASE INHIBITORS

CROSS-REFERENCE TO RELATED APPLICATIONS

This application claims priority to United States provisional patent application number 61/405,876, filed Oct. 22, 2010, which is hereby incorporated by reference in its entirety.

STATEMENT REGARDING FEDERALLY SPONSORED RESEARCH OR DEVELOPMENT

The research and development of the invention described below was not federally sponsored.

BACKGROUND OF THE INVENTION

*Cannabis sativa* has been used for the treatment of pain for many years. $\Delta^9$-tetrahydrocannabinol is a major active ingredient from *Cannabis sativa* and an agonist of cannabinoid receptors (Pertwee, *Brit J Pharmacol,* 2008, 153, 199-215). Two cannabinoid G protein-coupled receptors have been cloned, cannabinoid receptor type 1 ($CB_1$ Matsuda et al., *Nature,* 1990, 346, 561-4) and cannabinoid receptor type 2 ($CB_2$ Munro et al., *Nature,* 1993, 365, 61-5). $CB_1$ is expressed centrally in brain areas, such as the hypothalamus and nucleus accumbens as well as peripherally in the liver, gastrointestinal tract, pancreas, adipose tissue, and skeletal muscle (Di Marzo et al., *Curr Opin Lipidol,* 2007, 18, 129-140). $CB_2$ is predominantly expressed in immune cells, such as monocytes (Pacher et al., *Amer J Physiol,* 2008, 294, H1133-H1134), and under certain conditions, also in the brain (Benito et al., *Brit J Pharmacol,* 2008, 153, 277-285) and in skeletal (Cavuoto et al., *Biochem Biophys Res Commun,* 2007, 364, 105-110) and cardiac (Hajrasouliha et al., *Eur J Pharmacol,* 2008, 579, 246-252) muscle. An abundance of pharmacological, anatomical and electrophysiological data, using synthetic agonists, indicate that increased cannabinoid signaling through $CB_1/CB_2$ promotes analgesia in tests of acute nociception and suppresses hyperalgesia in models of chronic neuropathic and inflammatory pain (Cravatt et al., *J Neurobiol,* 2004, 61, 149-60; Guindon et al., *Brit J Pharmacol,* 2008, 153, 319-334).

Efficacy of synthetic cannabinoid receptor agonists is well documented. Moreover, studies using cannabinoid receptor antagonists and knockout mice have also implicated the endocannabinoid system as an important modulator of nociception. Anandamide (AEA) (Devane et al., *Science,* 1992, 258, 1946-9) and 2-arachidinoylglycerol (2-AG) (Mechoulam et al., *Biochem Pharmacol,* 1995, 50, 83-90; Sugiura et al., *Biochem Biophys Res Commun,* 1995, 215, 89-97) are two major endocannabinoids. AEA is hydrolyzed by fatty acid amide hydrolase (FAAH) and 2-AG is hydrolyzed by monoacylglycerol lipase (MGL) (Piomelli, *Nat Rev Neurosci,* 2003, 4, 873-884). Genetic ablation of FAAH elevates endogenous AEA and results in a $CB_1$-dependent analgesia in models of acute and inflammatory pain (Lichtman et al., *Pain,* 2004, 109, 319-27), suggesting that the endocannabinoid system functions naturally to inhibit pain (Cravatt et al., *J Neurobiol,* 2004, 61, 149-60). Unlike the constitutive increase in endocannabinoid levels using FAAH knockout mice, use of specific FAAH inhibitors transiently elevates AEA levels and results in antinociception in vivo (Kathuria et al., *Nat Med,* 2003, 9, 76-81). Further evidence for an endocannabinoid-mediated antinociceptive tone is demonstrated by the formation of AEA in the periaqueductal grey following noxious stimulation in the periphery (Walker et al., *Proc Natl Acad Sci USA,* 1999, 96, 12198-203) and, conversely, by the induction of hyperalgesia following antisense RNA-mediated inhibition of $CB_1$ in the spinal cord (Dogrul et al., *Pain,* 2002, 100, 203-9).

With respect to 2-AG, intravenous delivery of 2-AG produces analgesia in the tail flick (Mechoulam et al., *Biochem Pharmacol,* 1995, 50, 83-90) and hot plate (Lichtman et al., *J Pharmacol Exp Ther,* 2002, 302, 73-9) assays. In contrast, it was demonstrated that 2-AG given alone is not analgesic in the hot plate assay, but when combined with other 2-monoacylglycerols (i.e., 2-linoleoyl glycerol and 2-palmitoyl glycerol), significant analgesia is attained, a phenomenon termed the "entourage effect" (Ben-Shabat et al., *Eur J Pharmacol,* 1998, 353, 23-31). These "entourage" 2-monoacylglycerols are endogenous lipids that are co-released with 2-AG and potentiate endocannabinoid signaling, in part, by inhibiting 2-AG breakdown, most likely by competition for the active site on MGL. This suggests that synthetic MGL inhibitors will have a similar effect. Indeed, URB602, a relatively weak synthetic MGL inhibitor, showed an antinociceptive effect in a murine model of acute inflammation (Comelli et al., *Brit J Pharmacol,* 2007, 152, 787-794).

Although the use of synthetic cannabinoid agonists has conclusively demonstrated that increased cannabinoid signaling produces analgesic and anti-inflammatory effects, it has been difficult to separate these beneficial effects from the unwanted side effects of these compounds. An alternative approach is to enhance the signaling of the endocannabinoid system by elevating the level of 2-AG, the endocannabinoid of highest abundance in the central nervous system (CNS) and gastrointestinal tract, which may be achieved by inhibition of MGL. Therefore, MGL inhibitors are potentially useful for the treatment of pain, inflammation, and CNS disorders (Di Marzo et al., *Curr Pharm Des,* 2000, 6, 1361-80; Jhaveri et al., *Brit J Pharmacol,* 2007, 152, 624-632; McCarberg Bill et al., *Amer J Ther,* 2007, 14, 475-83), as well as glaucoma and disease states arising from elevated intraocular pressure (Njie, Ya Fatou; He, Fang; Qiao, Zhuanhong; Song, Zhao-Hui, *Exp. Eye Res.,* 2008, 87(2):106-14).

SUMMARY OF THE INVENTION

The present invention is directed to a compound of Formula (I)

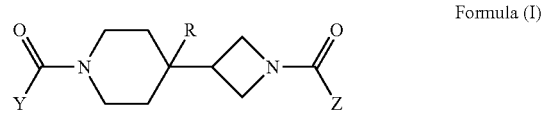

Formula (I)

wherein

Y and Z are independently selected from Group a) or Group b) such that one of Y and Z is Group a) and the other is Group b);

Group a) is i) $C_{6-10}$ aryl is unsubstituted or substituted with a substituent selected from the group consisting of fluoro, chloro, $C_{1-4}$alkyl, $C_{1-4}$alkoxy, cyano, and trifluoromethyl; or ii) an unsubstituted heteroaryl selected from the group consisting of thiazolyl, isothiazolyl, and 1H-pyrrolyl;

Group b) is i) $C_{6-10}$ aryl;

ii) a heteroaryl selected from the group consisting of benzoxazolyl, benzothiazolyl, benzimidazolyl, benzothienyl, indazolyl, and indolyl;

iii) phenylmethyl-phenyl wherein the phenyl group of phenylmethyl is unsubstituted or substituted with trifluoromethyl or fluoro; or iv) 1,3-dihydro-3H-benzimidazol-2-on-yl;

wherein Group b) other than phenylmethyl-phenyl is unsubstituted or substituted with one or two substitutents each of which is independently selected from the group consisting of bromo, chloro, fluoro, iodo, $C_{1-4}$alkyl, $C_{1-4}$alkoxy, and $R_b$; provided that no more than one substituent is $R_b$; and $R_b$ is selected from the group consisting of trifluoromethyl, 2,2,2-trifluoroethyl, 3,3,3-trifluoropropyl, 4,4-difluorocyclohexyl, thienyl, pyridinyl, and phenyl; wherein said thienyl, pyridinyl, and phenyl of $R_b$ are unsubstituted or substituted with one or two substitutents each of which is independently selected from the group consisting of trifluoromethyl, methyl, chloro, cyano, and fluoro;

R is hydrogen or hydroxy;

and enantiomers, diastereomers, solvates and pharmaceutically acceptable salts thereof.

The present invention also provides, inter alia, a pharmaceutical composition comprising, consisting of and/or consisting essentially of a pharmaceutically acceptable carrier, a pharmaceutically acceptable excipient, and/or a pharmaceutically acceptable diluent, and a compound of Formula (I) or a pharmaceutically acceptable salt form thereof.

Also provided are processes for making a pharmaceutical composition comprising, consisting of, and/or consisting essentially of admixing a compound of Formula (I) or a pharmaceutically acceptable salt form thereof, and a pharmaceutically acceptable carrier, a pharmaceutically acceptable excipient, and/or a pharmaceutically acceptable diluent.

The present invention further provides, inter alia, methods for treating or ameliorating a MGL-modulated disorder in a subject, including a human or other mammal in which the disease, syndrome, or condition is affected by the modulation of the MGL enzyme, such as pain and the diseases that lead to such pain, inflammation and CNS disorders, using a compound of Formula (I) or a pharmaceutically acceptable salt form thereof.

The present invention also provides, inter alia, methods for producing the instant compounds and pharmaceutical compositions and medicaments thereof.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as, $(C_{1-6}alkyl)_2$-amino-, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "benzo-fused cycloalkyl" refers to a 5- to 8-membered monocyclic cycloalkyl ring fused to a benzene ring. The carbon atom ring members that form the cycloalkyl ring may be fully saturated or partially saturated.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "benzo-fused heterocyclyl" refers to a 5 to 7 membered monocyclic heterocycle ring fused to a benzene ring. The heterocycle ring contains carbon atoms and from 1 to 4 heteroatoms independently selected from N, O, and S. The carbon atom ring members that form the heterocycle ring may be fully saturated or partially saturated. Unless otherwise noted, benzo-fused heterocycle ring is attached to its pendant group at a carbon atom of the benzene ring.

The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

The term "formyl" refers to the group —C(═O)H.

The term "oxo" refers to the group (═O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as subcombinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

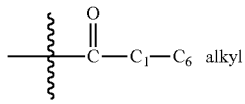

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of 2 enantiomers. Compounds containing 2 stereocenters both drawn without stereo bond designations are a mixture of 4 diastereomers. Compounds with 2 stereocenters both labeled "RS" and drawn with stereo bond designations are a 2-component mixture with relative stereochemistry as drawn. Compounds with 2 stereocenters both labeled "*RS" and drawn with stereo bond designations are a 2-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of Formula (I) can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "MGL inhibitor" is intended to encompass a compound that interacts with MGL to substantially reduce or eliminate its catalytic activity, thereby increasing the concentrations of its substrate(s). The term "MGL-modulated" is used to refer to the condition of being affected by the modulation of the MGL enzyme including the condition of being affected by the inhibition of the MGL enzyme such as pain, and the diseases that lead to such pain, inflammation and CNS disorders.

As used herein, unless otherwise noted, the term "affect" or "affected" (when referring to a disease, syndrome, condition or disorder that is affected by inhibition of MGL) includes a reduction in the frequency and/or severity of one or more symptoms or manifestations of said disease, syndrome, condition or disorder; and/or include the prevention of the development of one or more symptoms or manifestations of said disease, syndrome, condition or disorder or the development of the disease, condition, syndrome or disorder.

The compounds of Formula (I) are useful in methods for treating, ameliorating and/or preventing a disease, a syndrome, a condition or a disorder that is affected by the inhibition of MGL. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt thereof. In particular, the compounds of Formula (I), or an enantiomer, diastereomer, solvate or pharmaceutically acceptable salt thereof are useful for treating, ameliorating and/or preventing pain; diseases, syndromes, conditions, or disorders causing such pain; inflammation and/or CNS disorders. More particularly, the compounds of Formula (I), or an enantiomer, diastereomer, solvate or pharmaceutically acceptable salt thereof are useful for treating, ameliorating and/or preventing inflammatory pain, inflammatory hypersensitivity conditions and/or neuropathic pain, comprising administering to a subject in need thereof a therapeutically effective amount of a compound of Formula (I), or an enantiomer, diastereomer, solvate or pharmaceutically acceptable salt thereof as herein defined.

Examples of inflammatory pain include pain due to a disease, condition, syndrome, disorder, or a pain state including inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain due to physical trauma, headache, sinus headache, tension headache, or arachnoiditis.

One type of inflammatory pain is inflammatory hyperalgesia/hypersensitivity. Examples of inflammatory hyperalgesia include a disease, syndrome, condition, disorder, or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity and/or dermal allergy, itch, eczema, pharyngitis, enteritis, irritable bowel syndrome, inflammatory bowel diseases including Crohn's Disease, ulcerative colitis, benign prostatic hypertrophy, and nasal hypersensitivity.

In an embodiment, the present invention is directed to a method for treating, ameliorating and/or preventing inflammatory visceral hyperalgesia in which a enhanced visceral irritability exists, comprising, consisting of, and/or consisting essentially of the step of administering to a subject in need of such treatment a therapeutically effective amount of a compound, salt or solvate of Formula (I). In a further embodiment, the present invention is directed to a method for treating inflammatory somatic hyperalgesia in which a hypersensitivity to thermal, mechanical and/or chemical stimuli exists, comprising administering to a mammal in need of such treatment a therapeutically effective amount of a compound of Formula (I) or an enantiomer, diastereomer, solvate or pharmaceutically acceptable salt thereof.

A further embodiment of the present invention is directed to a method for treating, ameliorating and/or preventing neuropathic pain. Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngeal neuralgia, migrainous neuralgia, idiopathic neuralgia, intercostals neuralgia, mammary neuralgia, Morton's neuralgia, nasociliary neuralgia, occipital neuralgia, postherpetic neuralgia, causalgia, red neuralgia, Sluder's neuralgia, splenopalatine neuralgia, supraorbital neuralgia, trigeminal neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

In a further embodiment, the present invention is directed to a method for treating, ameliorating and/or preventing neuropathic cold allodynia in which a hypersensitivity to a cooling stimuli exists, comprising, consisting of, and/or consisting essentially of the step of administering to a subject in need of such treatment a therapeutically effective amount of a compound of Formula (I) or an enantiomer, diastereomer, solvate or pharmaceutically acceptable salt thereof.

In a further embodiment, the present invention is directed to a method for treating, ameliorating and/or preventing CNS disorders. Examples of CNS disorders include anxieties such as, social anxiety, post-traumatic stress disorder, phobias, social phobia, special phobias, panic disorder, obsessive-compulsive disorder, acute stress disorder, separation anxiety disorder, and generalized anxiety disorder, as well as depression such as, major depression, bipolar disorder, seasonal affective disorder, post natal depression, manic depression, and bipolar depression.

Embodiments of the present invention include a compound of Formula (I)

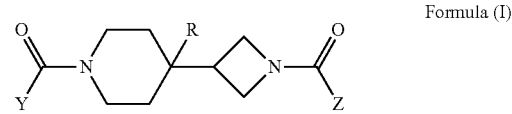

Formula (I)

wherein

Y and Z are independently selected from Group a) or Group b) such that one of Y and Z is Group a) and the other is Group b); and a) Group a) is unsubstituted phenyl or an unsubstituted heteroaryl selected from the group consisting of thiazolyl, isothiazolyl, and 1H-pyrrolyl;

b) Group a) is unsubstituted phenyl or an unsubstituted heteroaryl selected from the group consisting of thiazol-2-yl, thiazol-4-yl, thiazol-5-yl, isothiazolyl, 1H-pyrrol-2-yl, and 1H-pyrrol-3-yl;

c) Group b) is
  i) phenyl;
  ii) a heteroaryl selected from the group consisting of benzoxazolyl, benzimidazolyl, benzothienyl, and indolyl;
  iii) phenylmethyl-phenyl wherein the phenyl group of phenylmethyl is unsubstituted or substituted with trifluoromethyl or fluoro; or
  iv) 1,3-dihydro-3H-benzimidazol-2-on-yl;
    wherein Group b) other than phenylmethyl-phenyl is unsubstituted or substituted with one or two substitutents each of which is independently selected from the group consisting of chloro, fluoro, methyl, and $R_b$; provided that no more than one substituent is $R_b$; and
    $R_b$ is selected from the group consisting of trifluoromethyl, 2,2,2-trifluoroethyl, 3,3,3-trifluoropropyl, 4,4-difluorocyclohexyl, thienyl, pyridinyl, and phenyl; wherein said thienyl, pyridinyl, and phenyl of $R_b$ are unsubstituted or substituted with one or two substituents each of which is independently selected from the group consisting of trifluoromethyl, methyl, chloro, and fluoro;

d) Group b) is
 i) phenyl;
 ii) a heteroaryl selected from the group consisting of benzoxazolyl, benzimidazolyl, benzothienyl, and indolyl;
 iii) phenylmethyl-phenyl wherein the phenyl group of phenylmethyl is unsubstituted or substituted with trifluoromethyl; or
 iv) 1,3-dihydro-3H-benzimidazol-2-on-yl;
  wherein Group b) other than phenylmethyl-phenyl is unsubstituted or substituted with one or two substitutents independently selected from the group consisting of chloro, fluoro, methyl, and $R_b$; provided that no more than one substituent is $R_b$; and
  $R_b$ is selected from the group consisting of trifluoromethyl, thienyl, pyridinyl, and phenyl; wherein said thienyl, pyridinyl, and phenyl of $R_b$ are optionally independently substituted with one to two trifluoromethyl, methyl, chloro, or fluoro substituents;
e) R is hydrogen;
 and any combination of embodiments a) through e) above, provided that it is understood that combinations in which different embodiments of the same substituent would be combined are excluded;
and enantiomers, diastereomers, solvates and pharmaceutically acceptable salts thereof.

An embodiment of the present invention includes a compound of Formula (I)

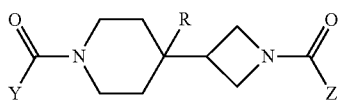

Formula (I)

wherein
Y and Z are independently selected from Group a) or Group b) such that one of Y and Z is Group a) and the other is Group b);
Group a) is an unsubstituted phenyl or an unsubstituted heteroaryl selected from the group consisting of thiazolyl, isothiazolyl, and 1H-pyrrolyl;
Group b) is
 i) phenyl;
 ii) a heteroaryl selected from the group consisting of benzoxazolyl, benzimidazolyl, benzothienyl, and indolyl;
 iii) phenylmethyl-phenyl wherein the phenyl group of phenylmethyl is unsubstituted or substituted with trifluoromethyl or fluoro; or
 iv) 1,3-dihydro-3H-benzimidazol-2-on-yl;
  wherein Group b) other than phenylmethyl-phenyl is unsubstituted or substituted with one or two substitutents independently selected from the group consisting of chloro, fluoro, methyl, and $R_b$; provided that no more than one substituent is $R_b$; and
  $R_b$ is selected from the group consisting of trifluoromethyl, 2,2,2-trifluoroethyl, 3,3,3-trifluoropropyl, 4,4-difluorocyclohexyl, thienyl, pyridinyl, and phenyl; wherein said thienyl, pyridinyl, and phenyl of $R_b$ are unsubstituted or substituted with one or two substituents independently selected from the group consisting of trifluoromethyl, methyl, chloro, and fluoro;
R is hydrogen;
and enantiomers, diastereomers, solvates and pharmaceutically acceptable salts thereof.

An embodiment of the present invention includes a compound of Formula (I)

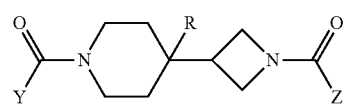

Formula (I)

wherein
Y and Z are independently selected from Group a) or Group b) such that one of Y and Z is Group a) and the other is Group b);
Group a) is an unsubstituted phenyl or an unsubstituted heteroaryl selected from the group consisting of thiazolyl, isothiazolyl, and 1H-pyrrolyl;
Group b) is
 i) phenyl;
 ii) a heteroaryl selected from the group consisting of benzoxazolyl, benzimidazolyl, benzothienyl, and indolyl;
 iii) phenylmethyl-phenyl wherein the phenyl group of phenylmethyl is unsubstituted or substituted with trifluoromethyl; or
 iv) 1,3-dihydro-3H-benzimidazol-2-on-yl;
  wherein Group b) other than phenylmethyl-phenyl is unsubstituted or substituted with one or two substitutents independently selected from the group consisting of chloro, fluoro, methyl, and $R_b$; provided that no more than one substituent is $R_b$; and
  $R_b$ is selected from the group consisting of trifluoromethyl, thienyl, pyridinyl, and phenyl; wherein said thienyl, pyridinyl, and phenyl of $R_b$ are unsubstituted or substituted with one or two substitutents independently selected from the group consisting of trifluoromethyl, methyl, chloro, and fluoro;
R is hydrogen or hydroxy;
and enantiomers, diastereomers, solvates and pharmaceutically acceptable salts thereof.

An embodiment of the present invention includes a compound of Formula (I)

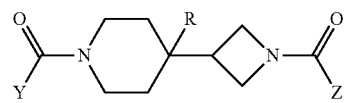

Formula (I)

wherein
Y and Z are independently selected from Group a) or Group b) such that one of Y and Z is Group a) and the other is Group b);
Group a) is unsubstituted phenyl or an unsubstituted heteroaryl selected from the group consisting of thiazol-2-yl, thiazol-4-yl, thiazol-5-yl, isothiazolyl, 1H-pyrrol-2-yl, and 1H-pyrrol-3-yl;
Group b) is
 i) phenyl;
 ii) a heteroaryl selected from the group consisting of benzoxazolyl, benzimidazolyl, benzothienyl, and indolyl;
 iii) phenylmethyl-phenyl wherein the phenyl group of phenylmethyl is unsubstituted or substituted with trifluoromethyl; or
 iv) 1,3-dihydro-3H-benzimidazol-2-on-yl;
  wherein Group b) other than phenylmethyl-phenyl is unsubstituted or substituted with one or two substitutents independently selected from the group consisting of chloro, fluoro, methyl, and $R_b$; provided that no more than one substituent is $R_b$; and $R_b$ is selected from the group consisting of trifluoromethyl, thienyl, pyridinyl, and phenyl; wherein said thienyl, pyridinyl, and phenyl of $R_b$ are unsubstituted or substituted with one or two substituents independently selected from the group consisting of trifluoromethyl, methyl, chloro, and fluoro;

R is hydrogen or hydroxy;

and enantiomers, diastereomers, solvates and pharmaceutically acceptable salts thereof.

An embodiment of the present invention includes a compound of Formula (I)

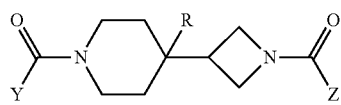

Formula (I)

selected from the group consisting of the compound wherein Y is thiazol-4-yl, Z is biphenyl-4-yl, and R is H;
the compound wherein Y is thiazol-2-yl, Z is biphenyl-4-yl, and R is H;
the compound wherein Y is isothiazol-5-yl, Z is biphenyl-4-yl, and R is H;
the compound wherein Y is 1H-pyrrol-3-yl, Z is biphenyl-4-yl, and R is H;
the compound wherein Y is thiazol-5-yl, Z is biphenyl-4-yl, and R is H;
the compound wherein Y is phenyl, Z is 5-trifluoromethyl-benzothien-2-yl, and R is OH;
the compound wherein Y is thiazol-4-yl, Z is 3-chloro-6-fluoro-benzothien-2-yl, and R is H;
the compound wherein Y is thiazol-2-yl, Z is 3-chloro-6-fluoro-benzothien-2-yl, and R is H;
the compound wherein Y is thiazol-4-yl, Z is 2-fluoro-4-phenyl-phenyl, and R is H;
the compound wherein Y is thiazol-4-yl, Z is 4-(3-trifluoromethylphenyl)-phenyl, and R is H;
the compound wherein Y is thiazol-4-yl, Z is 3-(3-fluorophenyl)-phenyl, and R is H;
the compound wherein Y is thiazol-4-yl, Z is 4-(5-trifluoromethylthien-2-yl)-phenyl, and R is H;
the compound wherein Y is thiazol-4-yl, Z is 4-(3-trifluoromethylphenylmethyl)-phenyl, and R is H;
the compound wherein Y is thiazol-4-yl, Z is 3-methyl-6-trifluoromethyl-benzothien-2-yl, and R is H;
the compound wherein Y is thiazol-2-yl, Z is 2-fluoro-4-phenyl-phenyl, and R is H;
the compound wherein Y is thiazol-2-yl, Z is 4-(3-trifluoromethylphenyl)-phenyl, and R is H;
the compound wherein Y is thiazol-2-yl, Z is 3-(3-fluorophenyl)-phenyl, and R is H;
the compound wherein Y is thiazol-2-yl, Z is 4-(5-trifluoromethylthien-2-yl)-phenyl, and R is H;
the compound wherein Y is thiazol-2-yl, Z is 4-(3-trifluoromethylphenylmethyl)-phenyl, and R is H;
the compound wherein Y is thiazol-2-yl, Z is 3-methyl-6-trifluoromethyl-benzothien-2-yl, and R is H;
the compound wherein Y is 1H-pyrrol-2-yl, Z is 2-fluoro-4-phenyl-phenyl, and R is H;
the compound wherein Y is 1H-pyrrol-2-yl, Z is 4-(3-trifluoromethylphenyl)-phenyl, and R is H;
the compound wherein Y is 1H-pyrrol-2-yl, Z is 3-(3-fluorophenyl)-phenyl, and R is H;
the compound wherein Y is 1H-pyrrol-2-yl, Z is 4-(5-trifluoromethylthien-2-yl)-phenyl, and R is H;
the compound wherein Y is 1H-pyrrol-2-yl, Z is 4-(3-trifluoromethylphenylmethyl)-phenyl, and R is H;
the compound wherein Y is 1H-pyrrol-2-yl, Z is 3-methyl-6-trifluoromethyl-benzothien-2-yl, and R is H;
the compound wherein Y is thiazol-2-yl, Z is 4-(4-trifluoromethylphenylmethyl)-phenyl, and R is H;
the compound wherein Y is thiazol-2-yl, Z is 2-phenyl-benzoxazol-6-yl, and R is H;
the compound wherein Y is thiazol-2-yl, Z is 3-chloro-6-trifluoromethyl-benzothien-2-yl, and R is H;
the compound wherein Y is thiazol-2-yl, Z is 1-(4-fluorophenyl)-1H-indol-5-yl, and R is H;
the compound wherein Y is thiazol-2-yl, Z is 1-(4-trifluoromethylphenyl)-1H-indol-5-yl, and R is H;
the compound wherein Y is thiazol-2-yl, Z is 1-(3,4-difluorophenyl)-1H-indol-5-yl, and R is H;
the compound wherein Y is thiazol-4-yl, Z is 4-(4-trifluoromethylphenylmethyl)-phenyl, and R is H;
the compound wherein Y is thiazol-4-yl, Z is 2-phenyl-benzoxazol-6-yl, and R is H;
the compound wherein Y is thiazol-4-yl, Z is 3-chloro-6-trifluoromethyl-benzothien-2-yl, and R is H;
the compound wherein Y is thiazol-4-yl, Z is 1-(4-fluorophenyl)-1H-indol-5-yl, and R is H;
the compound wherein Y is thiazol-4-yl, Z is 1-(4-trifluoromethylphenyl)-1H-indol-5-yl, and R is H;
the compound wherein Y is thiazol-4-yl, Z is 1-(3,4-difluorophenyl)-1H-indol-5-yl, and R is H;
the compound wherein Y is 1H-pyrrol-2-yl, Z is 4-(4-trifluoromethylphenylmethyl)-phenyl, and R is H;
the compound wherein Y is 1H-pyrrol-2-yl, Z is 2-phenyl-benzoxazol-6-yl, and R is H;
the compound wherein Y is 1H-pyrrol-2-yl, Z is 3-chloro-6-trifluoromethyl-benzothien-2-yl, and R is H;
the compound wherein Y is 1H-pyrrol-2-yl, Z is 1-(4-fluorophenyl)-1H-indol-5-yl, and R is H;
the compound wherein Y is 1H-pyrrol-2-yl, Z is 1-(4-trifluoromethylphenyl)-1H-indol-5-yl, and R is H;
the compound wherein Y is 1H-pyrrol-2-yl, Z is 1-(3,4-difluorophenyl)-1H-indol-5-yl, and R is H;
the compound wherein Y is 2-fluoro-4-phenyl-phenyl, Z is thiazol-2-yl, and R is H;
the compound wherein Y is 2-fluoro-4-phenyl-phenyl, Z is thiazol-4-yl, and R is H;
the compound wherein Y is 1H-pyrrol-2-yl, Z is 2-fluoro-4-phenyl-phenyl, and R is H;
the compound wherein Y is 4-(3-trifluoromethylphenyl)-phenyl, Z is thiazol-2-yl, and R is H;
the compound wherein Y is 4-(3-trifluoromethylphenyl)-phenyl, Z is thiazol-4-yl, and R is H;
the compound wherein Y is 4-(3-trifluoromethylphenyl)-phenyl, Z is 1H-pyrrol-2-yl, and R is H;
the compound wherein Y is 3-(3-fluorophenyl)-phenyl, Z is thiazol-2-yl, and R is H;
the compound wherein Y is 3-(3-fluorophenyl)-phenyl, Z is thiazol-4-yl, and R is H;
the compound wherein Y is 3-(3-fluorophenyl)-phenyl, Z is 1H-pyrrol-2-yl, and R is H;
the compound wherein Y is 4-(5-trifluoromethyl-thien-2-yl)-phenyl, Z is thiazol-2-yl, and R is H;
the compound wherein Y is 4-(5-trifluoromethyl-thien-2-yl)-phenyl, Z is thiazol-4-yl, and R is H;

the compound wherein Y is 4-(5-trifluoromethyl-thien-2-yl)-phenyl, Z is 1H-pyrrol-2-yl, and R is H;
the compound wherein Y is 4-(3-trifluoromethylphenylmethyl)-phenyl, Z is thiazol-2-yl, and R is H;
the compound wherein Y is 4-(3-trifluoromethylphenylmethyl)-phenyl, Z is thiazol-4-yl, and R is H;
the compound wherein Y is 4-(3-trifluoromethylphenylmethyl)-phenyl, Z is 1H-pyrrol-2-yl, and R is H;
the compound wherein Y is 3-methyl-6-trifluoromethyl-benzothien-2-yl, Z is thiazol-2-yl, and R is H;
the compound wherein Y is 3-methyl-6-trifluoromethyl-benzothien-2-yl, Z is thiazol-4-yl, and R is H;
the compound wherein Y is 3-methyl-6-trifluoromethyl-benzothien-2-yl, Z is 1H-pyrrol-2-yl, and R is H;
the compound wherein Y is 4-(4-trifluoromethylphenylmethyl)-phenyl, Z is thiazol-2-yl, and R is H;
the compound wherein Y is 4-(4-trifluoromethylphenylmethyl)-phenyl, Z is thiazol-4-yl, and R is H;
the compound wherein Y is 4-(4-trifluoromethylphenylmethyl)-phenyl, Z is 1H-pyrrol-2-yl, and R is H;
the compound wherein Y is 2-phenyl-benzoxazol-6-yl, Z is thiazol-2-yl, and R is H;
the compound wherein Y is 2-phenyl-benzoxazol-6-yl, Z is thiazol-4-yl, and R is H;
the compound wherein Y is 2-phenyl-benzoxazol-6-yl, Z is 1H-pyrrol-2-yl, and R is H;
the compound wherein Y is 3-chloro-6-trifluoromethyl-benzothien-2-yl, Z is thiazol-2-yl, and R is H;
the compound wherein Y is 3-chloro-6-trifluoromethyl-benzothien-2-yl, Z is thiazol-4-yl, and R is H;
the compound wherein Y is 3-chloro-6-trifluoromethyl-benzothien-2-yl, Z is 1H-pyrrol-2-yl, and R is H;
the compound wherein Y is 1-(4-fluorophenyl)-1H-indol-5-yl, Z is thiazol-2-yl, and R is H;
the compound wherein Y is 1-(4-fluorophenyl)-1H-indol-5-yl, Z is thiazol-4-yl, and R is H;
the compound wherein Y is 1-(4-fluorophenyl)-1H-indol-5-yl, Z is 1H-pyrrol-2-yl, and R is H;
the compound wherein Y is 1-(4-trifluoromethylphenyl)-1H-indol-5-yl, Z is thiazol-2-yl, and R is H;
the compound wherein Y is 1-(4-trifluoromethylphenyl)-1H-indol-5-yl, Z is thiazol-4-yl, and R is H;
the compound wherein Y is 1-(4-trifluoromethylphenyl)-1H-indol-5-yl, Z is 1H-pyrrol-2-yl, and R is H;
the compound wherein Y is 1-(3,4-difluorophenyl)-1H-indol-5-yl, Z is thiazol-2-yl, and R is H;
the compound wherein Y is 1-(3,4-difluorophenyl)-1H-indol-5-yl, Z is thiazol-4-yl, and R is H;
the compound wherein Y is 1-(3,4-difluorophenyl)-1H-indol-5-yl, Z is 1H-pyrrol-2-yl, and R is H;
the compound wherein Y is thiazol-2-yl, Z is 1-(4-fluorophenyl)-1H-benzimidazol-5-yl, and R is H;
the compound wherein Y is thiazol-2-yl, Z is 1-(3,4-difluorophenyl)-1H-benzimidazol-5-yl, and R is H;
the compound wherein Y is thiazol-2-yl, Z is 1-(4-trifluoromethylphenyl)-1H-benzimidazol-5-yl, and R is H;
the compound wherein Y is thiazol-2-yl, Z is 1-(2,2,2-trifluoroethyl)-1H-benzimidazol-5-yl, and R is H;
the compound wherein Y is thiazol-2-yl, Z is 1-(3,3,3-trifluoropropyl)-1H-benzimidazol-5-yl, and R is H;
the compound wherein Y is thiazol-2-yl, Z is 1-phenyl-2-methyl-1H-benzimidazol-5-yl, and R is H;
the compound wherein Y is thiazol-2-yl, Z is 1-(4-fluorophenyl)-2-methyl-1H-benzimidazol-5-yl, and R is H;
the compound wherein Y is thiazol-2-yl, Z is 1-(3,4-difluorophenyl)-2-methyl-1H-benzimidazol-5-yl, and R is H;
the compound wherein Y is thiazol-2-yl, Z is 1-(4-trifluoromethylphenyl)-2-methyl-1H-benzimidazol-5-yl, and R is H;
the compound wherein Y is thiazol-2-yl, Z is 1-(2,2,2-trifluoroethyl)-2-methyl-1H-benzimidazol-5-yl, and R is H;
the compound wherein Y is thiazol-2-yl, Z is 1-(3,3,3-trifluoropropyl)-2-methyl-1H-benzimidazol-5-yl, and R is H;
the compound wherein Y is thiazol-2-yl, Z is 1-(4,4-difluorocyclohexyl)-2-methyl-1H-benzimidazol-5-yl, and R is H;
the compound wherein Y is thiazol-2-yl, Z is 1-(5-chloropyridin-2-yl)-1H-indol-5-yl, and R is H;
the compound wherein Y is thiazol-2-yl, Z is 6-trifluoromethyl-benzothien-2-yl, and R is OH;
the compound wherein Y is thiazol-2-yl, Z is 1-(2-methylpyridin-4-yl)-1H-indol-5-yl, and R is H;
the compound wherein Y is thiazol-2-yl, Z is 1-phenyl-1,3-dihydro-3H-benzimidazol-2-on-5-yl, and R is H;
the compound wherein Y is thiazol-2-yl, Z is 1-(4-fluorophenyl)-1,3-dihydro-3H-benzimidazol-2-on-5-yl, and R is H;
the compound wherein Y is thiazol-2-yl, Z is 1-(3,4-difluorophenyl)-1,3-dihydro-3H-benzimidazol-2-on-5-yl, and R is H;
the compound wherein Y is thiazol-2-yl, Z is 1-(4-trifluoromethylphenyl)-1,3-dihydro-3H-benzimidazol-2-on-5-yl, and R is H;
the compound wherein Y is thiazol-2-yl, Z is 1-(3,3,3-trifluoropropyl)-1,3-dihydro-3H-benzimidazol-2-on-5-yl, and R is H;
the compound wherein Y is thiazol-2-yl, Z is 1-(4,4-difluorocyclohexyl)-1,3-dihydro-3H-benzimidazol-2-on-5-yl, and R is H;
and pharmaceutically acceptable salt forms thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salt forms thereof. Suitable pharmaceutically acceptable salts of compounds of Formula (I) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxoglutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholin, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\%(+) - \text{enantiomer} = \frac{(\text{mass}(+) - \text{enantiomer})}{(\text{mass}(+) - \text{enantiomer}) + (\text{mass}(-) - \text{enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-) - \text{enantiomer} = \frac{(\text{mass}(-) - \text{enantiomer})}{(\text{mass}(+) - \text{enantiomer}) + (\text{mass}(-) - \text{enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I).

Advantageously, a compound of Formula (I) may be administered in a single daily dose, or the total daily dosage may be administered in divided doses of two, three and four times daily.

Optimal dosages of a compound of Formula (I) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

As MGL Inhibitors, the compounds of Formula (I) are useful in methods for treating and preventing a disease, a syndrome, a condition or a disorder in a subject, including an animal, a mammal and a human in which the disease, the syndrome, the condition or the disorder is affected by the modulation, including inhibition, of the MGL enzyme. Such methods comprise, consist of and/or consist essentially of administering to a subject, including an animal, a mammal, and a human in need of such treatment or prevention a therapeutically effective amount of a compound, salt or solvate of Formula (I).

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes. The various starting materials used in the schemes and examples are commercially available or may be prepared by methods well within the skill of persons versed in the art. The variables are as defined herein.

Abbreviations used in the instant specification, particularly the schemes and examples, are as follows:

| | |
|---|---|
| AcCl | acetyl chloride |
| AcOH | glacial acetic acid |
| aq. | aqueous |
| Bn or Bzl | benzyl |
| Boc | tert-butyloxycarbonyl |
| conc. | concentrated |
| DBE | 1,2-dibromoethane |
| DCC | N,N'-dicyclohexyl-carbodiimide |
| DCE | 1,2-dichloroethane |
| DCM | dichloromethane |
| DIPEA | diisopropylethylamine |
| DMAP | 4-(N,N-dimethylamino)pyridine |
| DMA | N,N-dimethylacetamide |
| DMF | N,N-dimethylformamide |
| DMSO | dimethylsulfoxide |
| DPPA | diphenylphosphoryl azide |
| EDC | N-(3-dimethylaminopropyl)-N'-ethylcarbodiimide hydrochloride |
| ESI | electrospray ionization |
| EtOAc | ethyl acetate |
| EtOH | ethanol |
| h | hour(s) |
| HATU | O-(1H-7-azabenzotriazol-1-yl)-1,1,3,3-tetramethyluronium hexafluorophosphate |
| HBTU | O-(1H-benzotriazol-1-yl)-1,1,3,3-tetramethyluronium hexafluorophosphate |
| HEK | human embryonic kidney |
| HEPES | (4-(2-hydroxyethyl)-1-piperazineethane sulfonic acid |
| HMPA | hexamethylphosphoramide |
| HPLC | high performance liquid chromatography |
| mCPBA | meta-chloroperoxybenzoic acid |
| MeCN | acetonitrile |
| MeOH | methanol |
| MeOTf | methyl triflate |
| MHz | megahertz |
| min | minutes |
| MS | mass spectrometry |
| NMR | nuclear magnetic resonance |
| PIPES | piperazine-N,N'-bis(2-ethanesulfonic acid) |
| PyBrOP | bromo-tris-pyrrolidinophosphonium hexafluorophosphate |
| RP | reverse-phase |
| $R_t$ | retention time |
| TEA or $Et_3N$ | triethylamine |
| TFA | trifluoroacetic acid |
| THF | tetrahydrofuran |
| TLC | thin layer chromatography |
| TMS | tetramethylsilane |

Scheme A illustrates a route for the synthesis of intermediates that are useful for the preparation of compounds of Formula (I) wherein R is hydrogen.

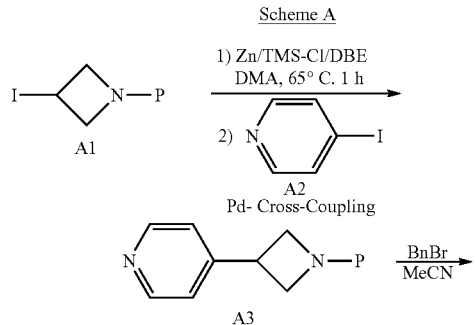

A compound of formula A1 (wherein P is a conventional amino protecting group) is either commercially available or may be prepared by known methods described in the scientific literature. A compound of formula A1 may be treated with zinc metal in the presence of TMS-Cl, in an aprotic solvent, followed by addition of a compound of formula A2, in the presence of palladium catalyst to afford a compound of formula A3. Treatment with benzyl bromide affords the pyridinium bromide of formula A4. A compound of formula A4 may be reduced to a compound of formula A5 in the presence of a hydride source such as, sodium borohydride, in an organic alcoholic solvent such as, ethanol. Removal of the benzyl group and reduction of the double bond may be achieved by palladium catalyzed hydrogenation to afford the desired intermediate of formula A6.

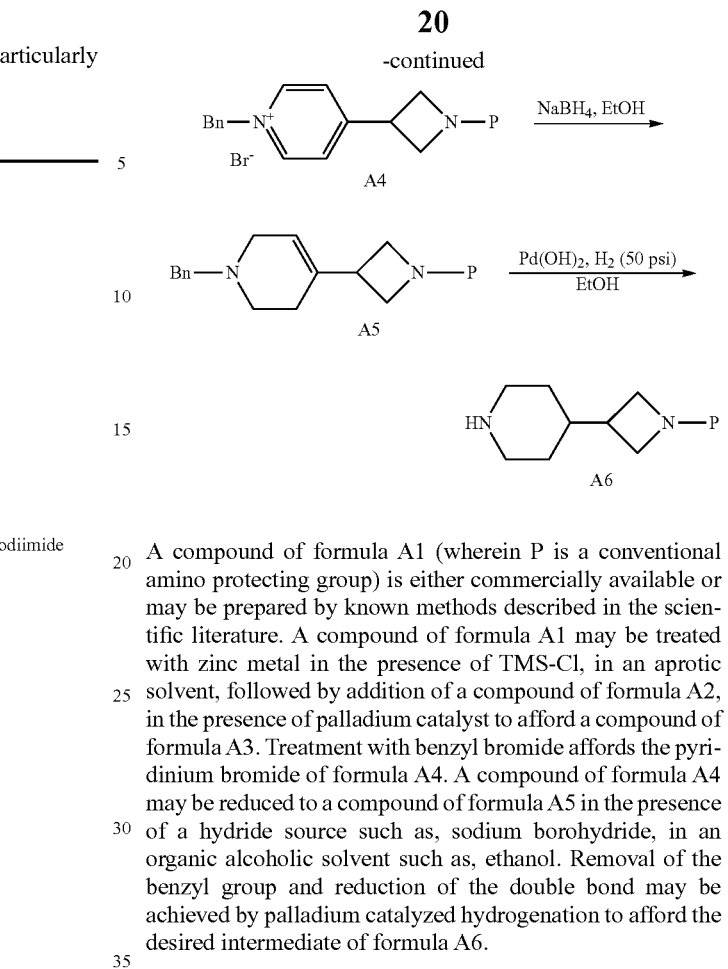

Scheme B illustrates a route for the preparation of compounds of Formula (I)-B wherein Y and Z are as defined herein and R of Formula (I) is hydrogen.

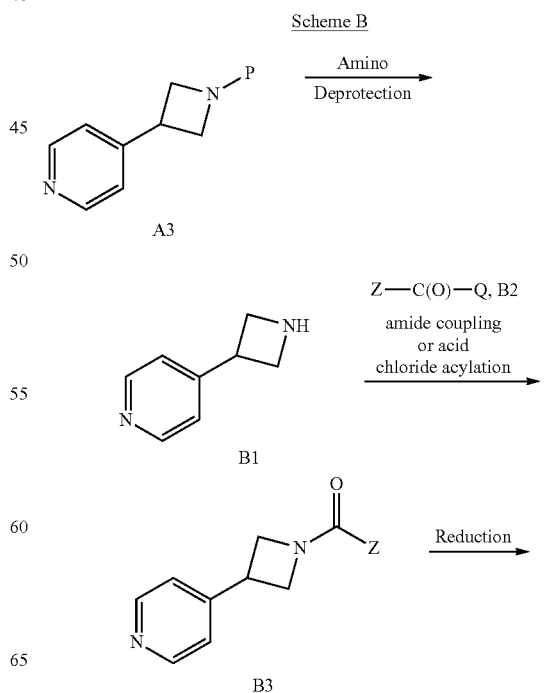

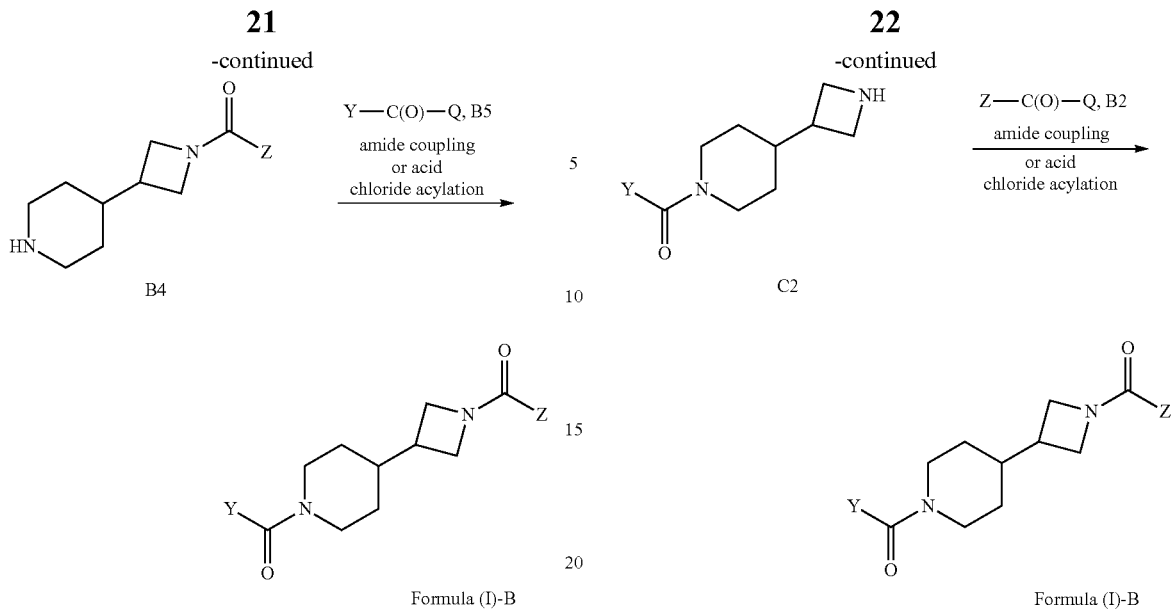

The amino protecting group (P) of a compound of formula A3 may be removed by conventional synthetic methods to afford a secondary amine of formula B1. The amino group may be coupled with a carboxylic acid of formula B2 (wherein Q is hydroxy) in the presence of an appropriate coupling agent such as HATU, DCC, EDC, HBTU, PyBrOP, and the like, optionally in the presence of a base such as DIPEA, to afford an amide of formula B3. Similarly, an acid chloride of formula B2 (wherein Q is chloro) may be used to effect the acylation of a compound of formula B1. In such case a non-nucleophilic base such as pyridine may be added to afford an amide of formula B3. Reduction of the pyridine ring of a compound of formula B3 may be achieved by palladium catalyzed hydrogenation to afford a compound of formula B4. A second acylation with an appropriately Y-substituted carboxylic acid or acid chloride of formula B5 affords a compound of Formula (I)-B wherein R of Formula (I) is hydrogen.

Scheme C illustrates an alternate route for the preparation of compounds of Formula (I)-B wherein Y and Z are as defined herein and R of Formula (I) is hydrogen.

The compound of formula A6 may be acylated according to the synthetic methods described under Scheme B to afford the acylated compound of formula C1. Conventional amino deprotection affords the amine of formula C2, which may undergo a second acylation as previously described to afford a compound of Formula (I)-B.

Scheme D illustrates a route for the preparation of compounds of Formula (I)-D wherein Y and Z are as defined herein and R of Formula (I) is hydroxy.

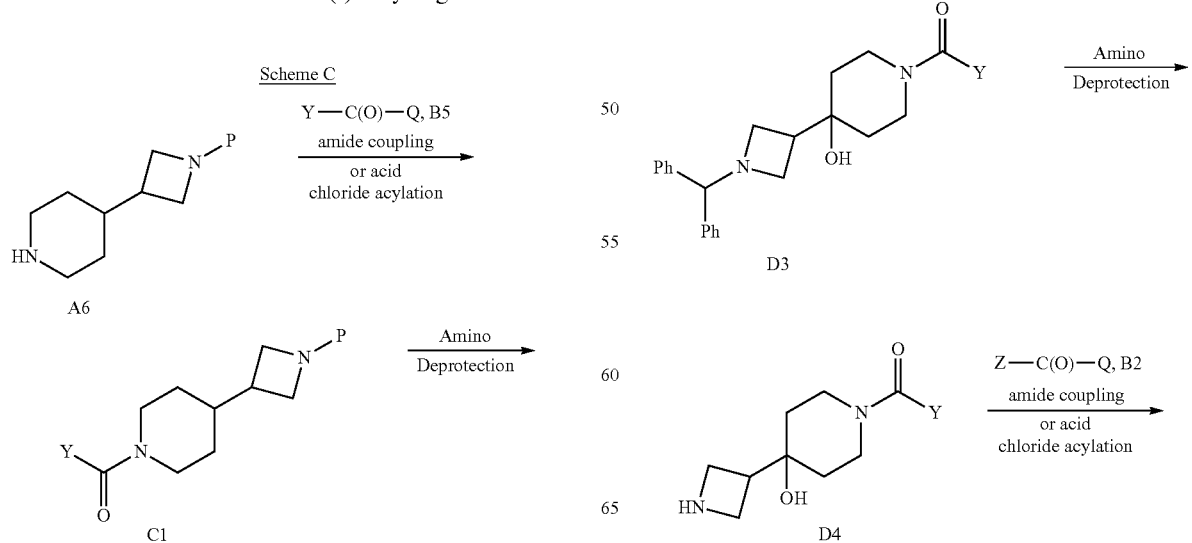

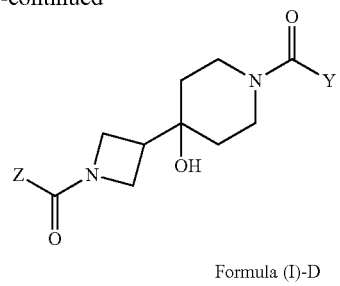

Formula (I)-D

Compounds of formulae D1 and D2 are either commercially available or may be prepared by known methods described in the scientific literature. A compound of formula D1 may be treated with samarium iodide in the presence of HMPA, in an aprotic solvent, followed by the addition of a ketone of formula D2 to afford the condensed product of formula D3. Removal of the benzhydryl group may be effected by palladium catalyzed hydrogenation to afford the free amine of formula D4. The amine of formula D4 may be acylated with a Z-substituted compound of formula B2 by the methods previously described herein to afford a compound of Formula (I)-D.

Scheme E illustrates an alternate route for the preparation of compounds of Formula (I)-D wherein Y and Z are as defined herein and R of Formula (I) is hydroxy.

Scheme E

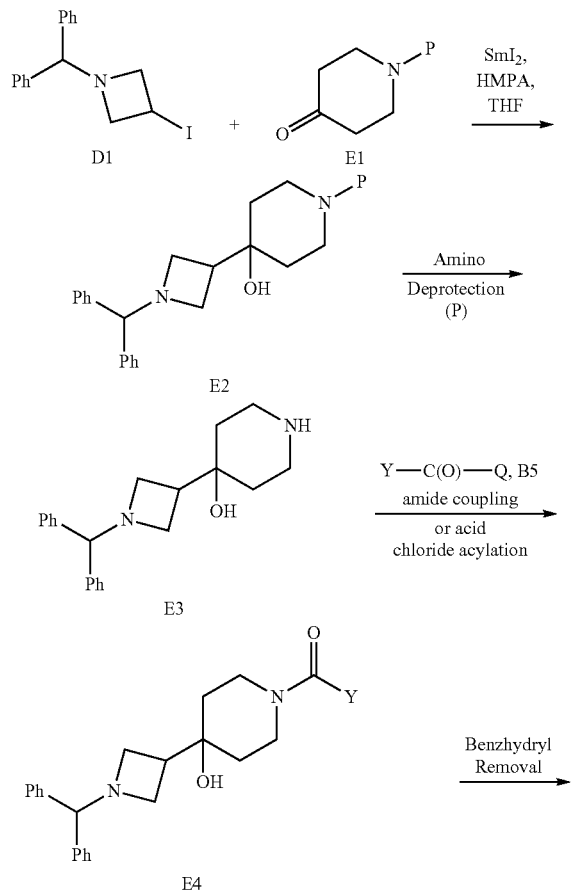

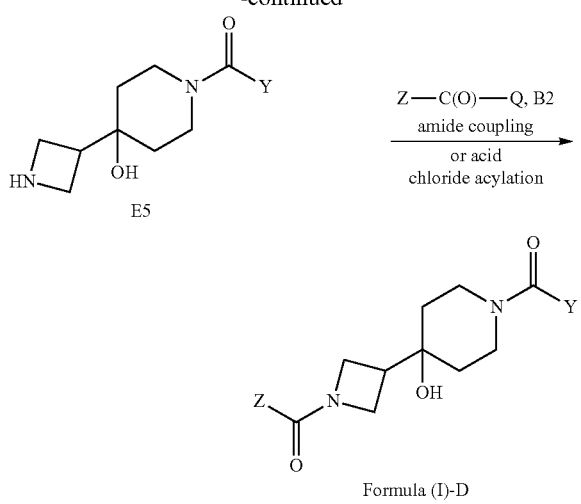

Formula (I)-D

A compound of formula D1 may be condensed with a compound of formula E1 in the presence of samarium iodide and HMPA to afford a compound of formula E2. Removal of the amino protecting group (P) using conventional synthetic methods affords a compound of formula E3. Acylation with a compound of formula B5 affords a compound of formula E4, which, upon benzhydryl removal, affords a free amine of formula E5. A second acylation with an appropriately substituted Z-substituted carboxylic acid or acid chloride of formula B2 affords a compound of Formula (I)-D.

Example 1

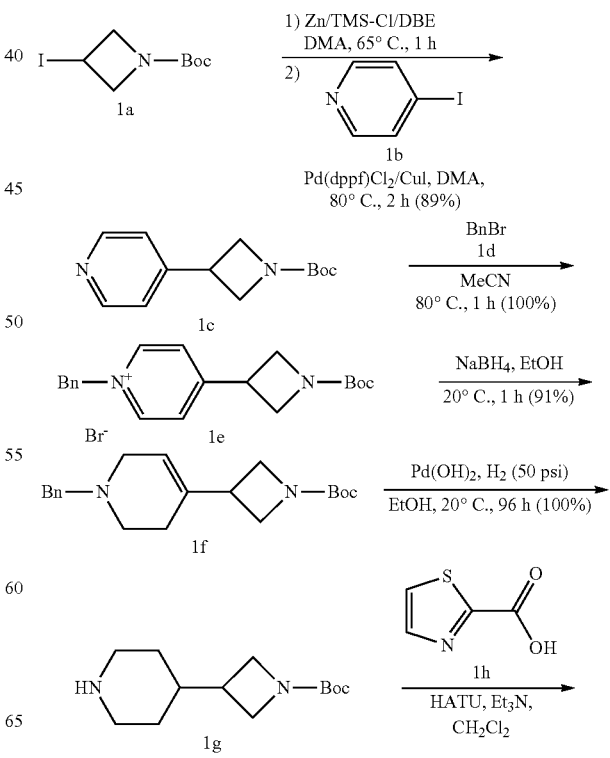

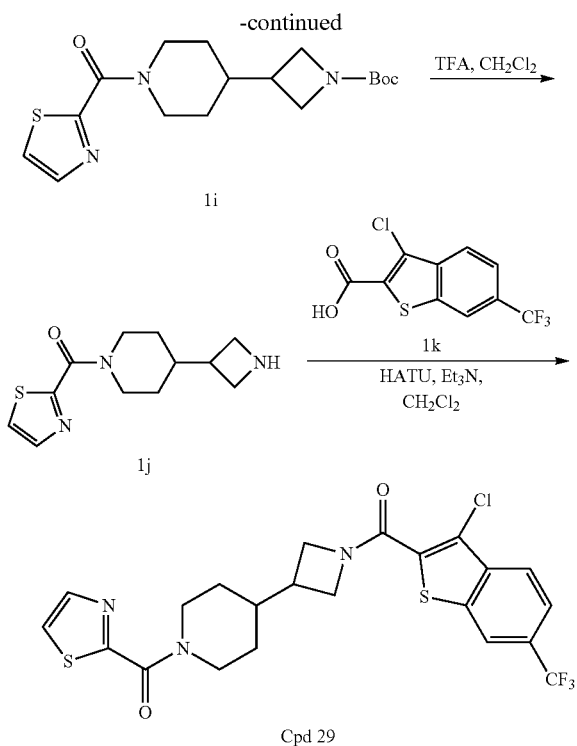

A. tert-Butyl 3-(pyridin-4-yl)azetidine-1-carboxylate, 1c. A 1-liter 3-neck round bottom flask equipped with a thermocouple, magnetic stirrer, condenser, heating mantle, and $N_2$ inlet adapter was charged with anhydrous dimethylacetamide (DMA, 100 mL) and zinc (42.94 g, 650.2 mmol). The mixture was stirred at 20° C. while a mixture of 1,2-dibromoethane (DBE, 5.38 mL, 62.34 mmol) and trimethylsilyl chloride (TMS-Cl, 7.54 mL, 59.28 mmol) was added at a rate to maintain the temperature below 65° C. over 30 min. The resulting slurry was aged for 15 min. A solution of tert-butyl 3-iodoazetidine-1-carboxylate 1a (122.78 g, 420.69 mmol) in DMA (201 mL) was added dropwise over 1 h at a rate to maintain the temperature below 65° C. and the milky suspension was stirred for 30 min while slowly cooling to 20° C.

Another 3-liter 4-neck round bottom flask equipped a thermocouple, mechanical stirrer, condenser, heating mantle, and $N_2$ inlet adapter was charged with [1,1'-bis(diphenylphosphino)ferrocene]dichloropalladium(II) dichloromethane complex (4.73 g, 5.74 mmol), cuprous iodide (2.19 g, 11.47 mmol), and 4-iodopyridine 1b (80.0 g, 382.44 mmol) in DMA (255 mL) under $N_2$. The resulting mixture was degassed with alternate vacuum/$N_2$ purges. The above prepared zinc iodide reagent of compound 1a in DMA was added as a suspension. The mixture was degassed with vacuum/$N_2$ twice and then heated to 80° C. (Note: The reaction was exothermic). The progress of the reaction was monitored by HPLC and LC-MS and was complete after 2 h. The reaction mixture was cooled to 40° C.; EtOAc (1.6 L) was added and the mixture was stirred for 10 min. The insoluble material (excess Zn and Cu complexes/salts) was removed by passing through a diatomaceous earth pad, which was washed with EtOAc (200 mL×2). The combined filtrate was stirred with 1 N aqueous $NH_4Cl$ (0.8 L) at 20° C. for 30 min and the aqueous layer (pH=5-6) was adjusted to pH=9-10 using 3 N aqueous NaOH solution (~480 mL) while a significant amount of brown precipitate was formed. The precipitate was removed by paper filtration and was washed with deionized water (100 mL). The separated aqueous phase was extracted with EtOAc (1 L), and the combined organic phases were treated with saturated aqueous $NH_4Cl$ (0.8 L×2) and stirred for 15 min (repeated again), washed with 5% aqueous $NaHSO_3$ (500 mL) and brine (1 L), and dried over $MgSO_4$. The organic solvent was concentrated at 66° C. under house vacuum (~120 mmHg) and then high-vacuum (12 mmHg) to afford 80.1 g (89% isolated yield) of crude compound 1c as an oil (88% purity at 254 nm and 86% purity at 230 nm; HPLC area %. Retention time=2.39 min), which was used in the next step without further purification.

B. 1-Benzyl-4-(1-(tert-butoxycarbonyl)azetidin-3-yl)pyridin-1-ium bromide, 1e. A 2-liter 4-neck round bottom flask equipped a thermocouple, mechanical stirrer, condenser, and $N_2$ inlet adapter was charged with crude compound 1c (78.22 g, 290.5 mmol) and acetonitrile (503 mL). The mixture was stirred at 20° C. and benzyl bromide 1d (36.41 mL, 299.2 mmol) was added. The mixture was warmed to 80° C. and stirred for 1 h. The reaction was cooled to 20° C. and the solvent was concentrated at 60° C. under house-/high-vacuum. The resulting material was chased with MeOH (100 mL) once to afford 128.9 g (109% isolated yield; 80-84% purity; HPLC area %. HPLC retention time=3.61 min) of crude 1e as a syrup, which was used in next step without further purification.

C. tert-Butyl 3-(1-benzyl-1,2,3,6-tetrahydropyridin-4-yl)azetidine-1-carboxylate, 1f. A 3-liter 4-neck round bottom flask equipped a thermocouple, mechanical stirrer, condenser, and $N_2$ inlet adapter was charged with crude compound 1e (117.73 g, 232.4 mmol) and EtOH (1.04 L). The solution was cooled to 0° C. with stirring; sodium tetrahydroborate (17.8 g, 464.7 mmol) was added and the mixture was stirred at 0° C. for 10 min, then gradually warmed to 20° C. and stirred for 1 h. The mixture was cooled to 0° C. and quenched with half-saturated $NaHCO_3$ (100 mL, prepared by adding 50 mL of deionized water to 50 mL of saturated $NaHCO_3$). The organic solvent was concentrated at 60° C. under house vacuum to a wet solid, which was dissolved in EtOAc (1.5 L) and stirred for 10 min with half saturated $NaHCO_3$ (1 L). After phase separation, the milky aqueous layer (pH=6-7) was adjusted to pH=10-11 using 3 N aqueous NaOH solution and extracted with EtOAc (500 mL). The combined organic phases were washed with brine (500 mL) and then concentrated at 60° C. under house-/high-vacuum to afford 98.7 g of crude 1f as a syrup, which was purified using flash column chromatography (silica gel, EtOAc/heptane/MeOH 20/80/0 –50/50/3) to afford 67.11 g (91% isolated yield, 95% purity at 210 nm; HPLC area %) of compound 1f as a yellow syrup.

D. tert-Butyl 3-(piperidin-4-yl)azetidine-1-carboxylate, 1g. A 500-mL Parr pressure bottle was charged with compound 1f (18.4 g, 54.3 mmol), EtOH (152 mL), and $Pd(OH)_2$ (1.91 g). The mixture was purged twice with $N_2$ and then shaken under a 50 psi $H_2$ atmosphere at 20° C. After 40 h, the $H_2$ was removed and additional $Pd(OH)_2$ (1.9 g) was added to the mixture of 1f, dihydro-1f, and 1g, which was purged twice with $N_2$ and shaken under a 50 psi $H_2$ atmosphere at 20° C. for an additional 56 h. The catalyst was removed by filtration though a diatomaceous earth pad, which was washed with MeOH (50 mL×3). Concentration of the filtrate at 50° C. under high-vacuum (~10 mmHg) afforded 13.4 g (103% isolated yield, 97% pure at 210 nm, HPLC area %) of pure compound 1g as a slight yellowish, thick oil, which contained a trace amount of EtOH residue by $^1$H-NMR analysis.

E. tert-Butyl 3-(1-(thiazole-2-carbonyl)piperidin-4-yl)azetidine-1-carboxylate, 1i. To a stirring solution of compound 1g (14.3 mmol, 3.44 g) and thiazole-2-carboxylic acid 1h (15.7 mmol, 2.03 g) in 50 mL of CH$_2$Cl$_2$ was added Et$_3$N (42.9 mmol, 5.98 mL). After 20 min at 20° C., HATU (17.2 mmol, 6.53 g) was added and the mixture was stirred at 20° C. for 5 h. Water was added to the mixture and the organic layer was separated, dried over MgSO$_4$, and concentrated. The residue was purified using flash column chromatography (silica gel, 30-70% EtOAc/heptane) to give 3.8 g (75% yield) of compound 1i. MS m/z 374.2 (M+Na$^+$), 296.1 (M+H—C$_4$H$_8$), 252.1 (M+H—C$_5$H$_8$O$_2$).

F. (4-(Azetidin-3-yl)piperidin-1-yl)(thiazol-2-yl)methanone, 1j. A portion of TFA (20 mL) was added to a solution of compound 1i (10.8 mmol, 3.8 g) in 100 mL of CH$_2$Cl$_2$. The solution was stirred at 20° C. for 5 h. The solvent was removed under vacuum and the residue was partitioned between CH$_2$Cl$_2$ and 1N aqueous NaOH. The organic layer was dried over MgSO$_4$ and concentrated to give 2.6 g (85% yield) of compound 1j, which was used in the next reaction without purification. MS m/z 252.1 (M+H$^+$).

G. 4-(1-{[3-Chloro-6-(trifluoromethyl)-1-benzothiophen-2-yl]carbonyl}azetidin-3-yl)-1-(1,3-thiazol-2-ylcarbonyl)piperidine, Cpd 29. To a stirring solution of compound 1j (1.59 mmol, 0.40 g) and 3-chloro-6-(trifluoromethyl)benzo[b]thiophene-2-carboxylic acid 1k (1.75 mmol, 0.49 g) in 10 mL of CH$_2$Cl$_2$ was added Et$_3$N (6.37 mmol, 0.89 mL). After 20 min at 20° C., HATU (1.91 mmol, 0.73 g) was added and the mixture was stirred at 20° C. for 20 h. The solvent was removed and the crude residue was purified by preparative reverse-phase chromatography to give 210 mg (26% yield) of Cpd 29. $^1$H NMR (CD$_3$OD, 400 MHz): δ=8.40 (s, 1H), 8.08 (d, J=8.6 Hz, 1H), 7.93 (br. s., 1H), 7.75-7.85 (m, 2H), 5.31 (t, J=10.8 Hz, 1H), 4.63 (t, J=11.0 Hz, 1H), 4.37 (t, J=8.2 Hz, 1H), 4.28 (t, J=9.3 Hz, 1H), 4.10 (br. s., 1H), 4.00 (br. s., 1H), 3.15-3.29 (m, 1H), 2.82-3.00 (m, 1H), 2.47-2.63 (m, 1H), 1.67-2.02 (m, 3H), 1.05-1.34 (m, 2H). MS m/z 514.0 (M+H$^+$).

Following the procedure described above for Example 1 and substituting the appropriate reagents, starting materials and purification methods known to those skilled in the art, the following compounds of the present invention were prepared:

| Cpd | Name and data |
|---|---|
| 35 | 4-(1-{[3-Chloro-6-(trifluoromethyl)-1-benzothiophen-2-yl]carbonyl}azetidin-3-yl)-1-(1,3-thiazol-4-ylcarbonyl)piperidine. $^1$H NMR (CD$_3$OD, 400 MHz): δ = 9.04 (br. s., 1H), 8.39 (s, 1H), 8.08 (d, J = 8.6 Hz, 1H), 8.01 (s, 1H), 7.81 (d, J = 8.6 Hz, 1H), 4.56-4.73 (m, 1H), 3.87-4.44 (m, 5H), 3.05-3.24 (m, 1H), 2.76-2.97 (m, 1H), 2.47-2.64 (m, 1H), 1.57-1.94 (m, 3H), 1.06-1.30 (m, 2H). MS m/z 514.0 (M + H$^+$). |
| 41 | 4-(1-{[3-Chloro-6-(trifluoromethyl)-1-benzothiophen-2-yl]carbonyl}azetidin-3-yl)-1-(1H-pyrrol-2-ylcarbonyl)piperidine. $^1$H NMR (CD$_3$OD, 400 MHz): δ = 8.41 (s, 1H), 8.10 (d, J = 8.6 Hz, 1H), 7.83 (d, J = 8.1 Hz, 1H), 6.90 (dd, J = 2.4, 1.2 Hz, 1H), 6.54 (dd, J = 3.7, 1.2 Hz, 1H), 6.13-6.21 (m, 1H), 4.57 (t, J = 13.2 Hz, 2H), 4.33-4.42 (m, 1H), 4.29 (t, J = 9.4 Hz, 1H), 4.10 (dd, J = 9.4, 6.2 Hz, 1H), 3.94-4.04 (m, 1H), 3.05 (br. s., 2H), 2.49-2.63 (m, 1H), 1.70-1.98 (m, 3H), 1.06-1.25 (m, 2H). MS m/z 496.2 (M + H$^+$). |
| 69 | 1-{[3-Chloro-6-(trifluoromethyl)-1-benzothiophen-2-yl]carbonyl}-4-[1-(1,3-thiazol-2-ylcarbonyl)azetidin-3-yl]piperidine. MS m/z 514.0 (M + H$^+$). |
| 70 | 1-{[3-Chloro-6-(trifluoromethyl)-1-benzothiophen-2-yl]carbonyl}-4-[1-(1,3-thiazol-4-ylcarbonyl)azetidin-3-yl]piperidine. MS m/z 514.0 (M + H$^+$). |
| 71 | 1-{[3-Chloro-6-(trifluoromethyl)-1-benzothiophen-2-yl]carbonyl}-4-[1-(1H-pyrrol-2-ylcarbonyl)azetidin-3-yl]piperidine. MS m/z 496.0 (M + H$^+$). |

Example 2

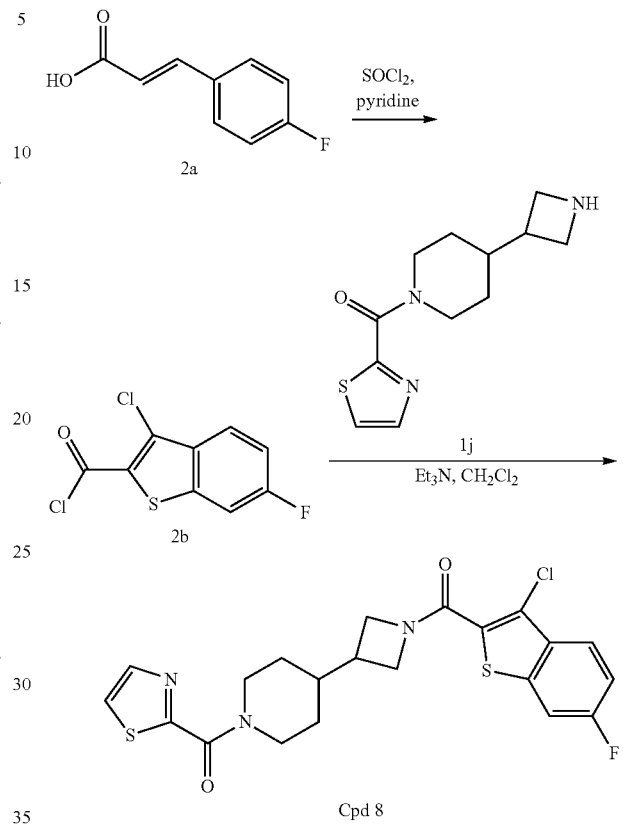

Cpd 8

A. 3-Chloro-6-fluorobenzo[b]thiophene-2-carbonyl chloride, 2b. Thionyl chloride (73.7 mmol, 5.36 mL) was added to a mixture of 4-fluorocinnamic acid 2a (21.1 mmol, 3.5 g) and pyridine (2.53 mmol, 0.2 mL). The mixture was heated at 135° C. for 30 min and then cooled to room temperature. The crude mixture was triturated with hot hexanes to remove the solid pyridinium hydrochloride by-product. Compound 2b was isolated from the combined hexanes solutions.

B. 4-{1-[(3-Chloro-6-fluoro-1-benzothiophen-2-yl)carbonyl]azetidin-3-yl}-1-(1,3-thiazol-2-ylcarbonyl)piperidine, Cpd 8. A solution of compound 2b (0.45 mmol, 112 mg) in 4 mL of CH$_2$Cl$_2$ was added to a solution of compound 1j mono-TFA salt (0.41 mmol, 150 mg) in Et$_3$N (2.46 mmol, 0.34 mL) at 0° C. The reaction mixture was stirred at 0° C. for 3 h. The crude product was purified by preparative reverse-phase chromatography to afford 18 mg (9% yield) of Cpd 8. $^1$H NMR (CD$_3$OD, 400 MHz): δ=7.88-7.97 (m, 2H), 7.81 (d, J=2.9 Hz, 1H), 7.76 (dd, J=8.8, 2.2 Hz, 1H), 7.36 (td, J=9.0, 2.3 Hz, 1H), 5.22-5.37 (m, 1H), 4.55-4.70 (m, 1H), 4.32-4.44 (m, 1H), 4.23-4.32 (m, 1H), 4.11 (br. s., 1H), 3.91-4.05 (m, 1H), 3.15-3.28 (m, 1H), 2.84-3.00 (m, 1H), 2.48-2.62 (m, 1H), 1.70-2.02 (m, 3H), 1.10-1.29 (m, 2H). MS m/z 464.1 (M+H$^+$).

Following the procedure described above for Example 2 and substituting the appropriate reagents, starting materials and purification methods known to those skilled in the art, the following compound of the present invention was prepared:

| Cpd | Name and data |
|---|---|
| 7 | 4-{1-[(3-Chloro-6-fluoro-1-benzothiophen-2-yl)carbonyl]azetidin-3-yl}-1-(1,3-thiazol-4-ylcarbonyl)piperidine. MS m/z 464.1 (M + H+). |

Example 3

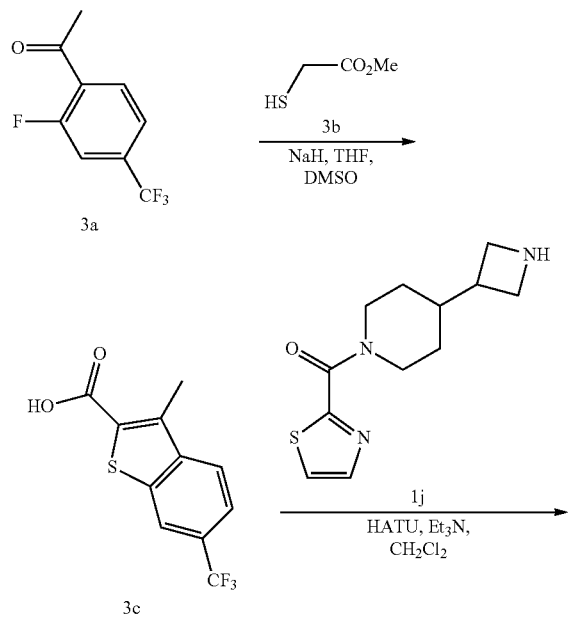

A. 3-Methyl-6-(trifluoromethyl)benzo[b]thiophene-2-carboxylate, 3c. Methyl thioglycolate 3b (30.3 mmol, 2.76 mL) was added dropwise to a suspension of NaH (60% oil dispersion, 75.8 mmol, 3.03 g) in 10 mL of THF and 50 mL of DMSO at 20° C. The mixture was stirred for 15 min and a solution of 1-(2-fluoro-4-(trifluoromethyl)phenyl)ethanone 3a (24.3 mmol, 5.0 g) in 10 mL of DMSO was added. The reaction mixture was stirred at 20° C. for 4 h and water was added. The mixture was extracted with EtOAc. The organic layer was dried over MgSO₄ and concentrated to give compound 3c as a white solid.

B. 4-(1-{[3-Methyl-6-(trifluoromethyl)-1-benzothiophen-2-yl]carbonyl}azetidin-3-yl)-1-(1,3-thiazol-2-ylcarbonyl) piperidine, Cpd 20. To a stirring solution of compound 1j mono-TFA salt (0.27 mmol, 100 mg) and compound 3c (0.30 mmol, 78 mg) in 4 mL of CH₂Cl₂ was added Et₃N (1.09 mmol, 0.15 mL). After 20 min at 20° C., HATU (0.33 mmol, 125 mg) was added and the mixture was stirred at 20° C. for 20 h. The solvent was removed and the crude residue was purified by preparative reverse-phase chromatography to give 34 mg (25% yield) of Cpd 20.

$^1$H NMR (CD$_3$OD, 400 MHz): δ=8.29 (s, 1H), 8.04 (d, J=8.6 Hz, 1H), 7.93 (br. s., 1H), 7.81 (d, J=3.2 Hz, 1H), 7.71 (d, J=8.3 Hz, 1H), 5.31 (br. s., 1H), 4.56-4.69 (m, 1H), 4.32-4.42 (m, 1H), 4.26 (t, J=9.2 Hz, 1H), 4.09 (br. s., 1H), 3.98 (br. s., 1H), 3.23 (br. s., 1H), 2.92 (br. s., 1H), 2.61 (s, 3H), 2.47-2.59 (m, 1H), 1.70-2.00 (m, 3H), 1.03-1.35 (m, J=9.3 Hz, 2H). MS m/z 494.1 (M+H+).

Following the procedure described above for Example 3, and substituting the appropriate reagents, starting materials and purification methods known to those skilled in the art, the following compounds of the present invention were prepared:

| Cpd | Name and data |
|---|---|
| 14 | 4-(1-{[3-Methyl-6-(trifluoromethyl)-1-benzothiophen-2-yl]carbonyl}azetidin-3-yl)-1-(1,3-thiazol-4-ylcarbonyl)piperidine. MS m/z 494.1 (M + H+). |
| 26 | 4-(1-{[3-Methyl-6-(trifluoromethyl)-1-benzothiophen-2-yl]carbonyl}azetidin-3-yl)-1-(1H-pyrrol-2-ylcarbonyl)piperidine. MS m/z 476.2 (M + H+). |
| 60 | 1-{[3-Methyl-6-(trifluoromethyl)-1-benzothiophen-2-yl]carbonyl}-4-[1-(1,3-thiazol-2-ylcarbonyl)azetidin-3-yl]piperidine. MS m/z 494.1 (M + H+). |
| 61 | 1-{+3-Methyl-6-(trifluoromethyl)-1-benzothiophen-2-yl]carbonyl}-4-[1-(1,3-thiazol-4-ylcarbonyl)azetidin-3-yl]piperidine. MS m/z 494.1 (M + H+). |
| 62 | 1-{+3-Methyl-6-(trifluoromethyl)-1-benzothiophen-2-yl]carbonyl}-4-[1-(1H-pyrrol-2-ylcarbonyl)azetidin-3-yl]piperidine. MS m/z 476.2 (M + H+). |

Example 4

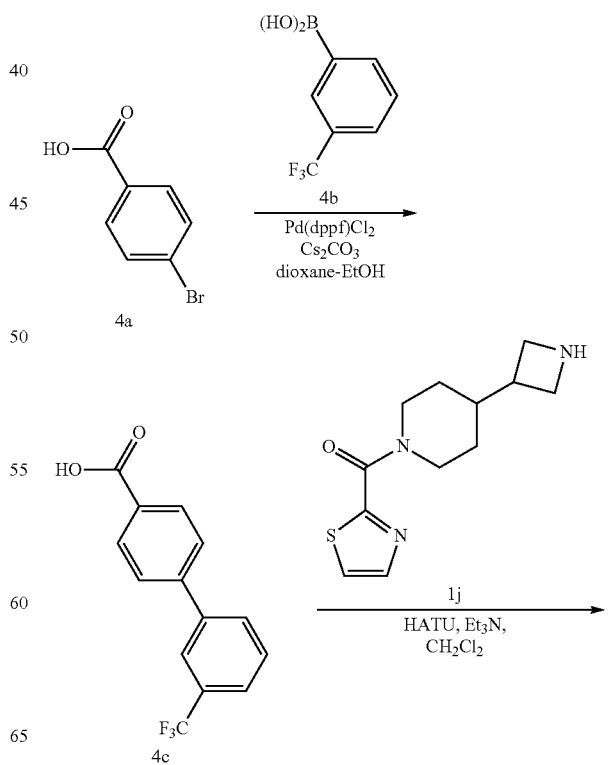

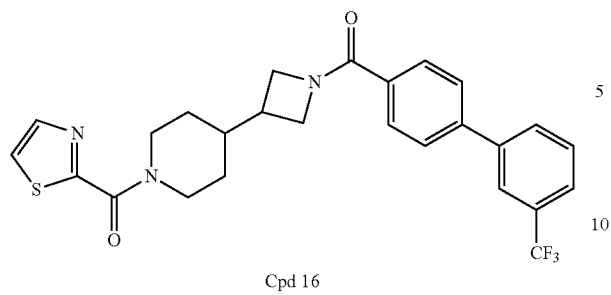

Cpd 16

A. 3'-(Trifluoromethyl)-[1,1'-biphenyl]-4-carboxylic acid, 4c. A portion of Pd(dppf)Cl$_2$ (1.49 mmol, 1.09 g) was added to a suspension of 4-bromobenzoic acid 4a (14.9 mmol, 3.0 g), 3-trifluoromethylboronic acid 4b (17.9 mmol, 3.4 g), and Cs$_2$CO$_3$ (37.3 mmol, 12.2 g) in 30 mL of dioxane and 7.5 mL of EtOH. The mixture was stirred at 80° C. for 2 h. After cooling, the solid was collected by filtration and washed with MeOH. The filtrate was concentrated and partitioned between EtOAc and 1N aqueous HCl. The organic layer was washed with brine, dried over MgSO$_4$, and concentrated. CH$_2$Cl$_2$ was added to the residue and the resulting solid was collected by filtration, washed with CH$_2$Cl$_2$, and dried to give 3.58 g (86% yield) of compound 4c, which was used in the next step without further purification.

B. 1-(1,3-Thiazol-2-ylcarbonyl)-4-(1-{[3'-(trifluoromethyl)biphenyl-4-yl]carbonyl}azetidin-3-yl)piperidine, Cpd 16. To a stirring solution of compound 1j mono-TFA salt (0.27 mmol, 100 mg) and compound 4c (0.30 mmol, 80 mg) in 4 mL of CH$_2$Cl$_2$ was added Et$_3$N (1.09 mmol, 0.15 mL). After 20 min at 20° C., HATU (0.33 mmol, 125 mg) was added and the mixture was stirred at 20° C. for 20 h. The solvent was removed and the crude residue was purified by preparative reverse-phase chromatography to give 57 mg (42% yield) of Cpd 16. $^1$H NMR (CD$_3$OD, 400 MHz): δ=7.93 (br. s., 3H), 7.73-7.83 (m, 5H), 7.63-7.73 (m, 2H), 5.24-5.38 (m, 1H), 4.64 (t, J=10.8 Hz, 1H), 4.46 (t, J=8.2 Hz, 1H), 4.13-4.31 (m, 2H), 3.90-4.01 (m, 1H), 3.15-3.29 (m, 1H), 2.84-2.99 (m, 1H), 2.44-2.60 (m, 1H), 1.73-2.00 (m, 3H), 1.08-1.32 (m, 2H). MS m/z 500.3 (M+H$^+$).

Following the procedure described above for Example 4 and substituting the appropriate reagents, starting materials and purification methods known to those skilled in the art, the following intermediate compounds were prepared:

4-11

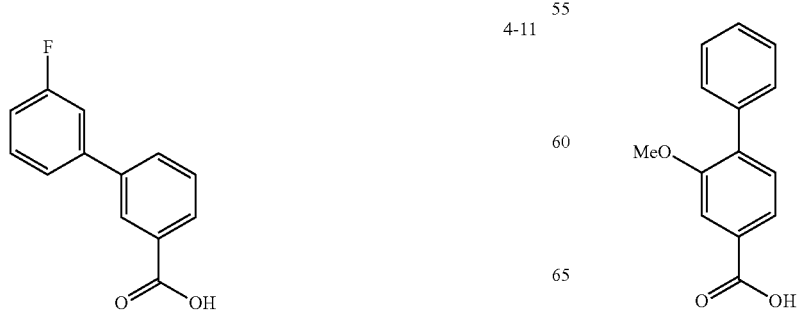

4-12

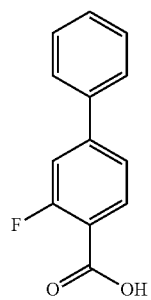

4-13

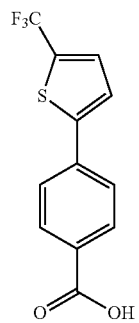

4-14

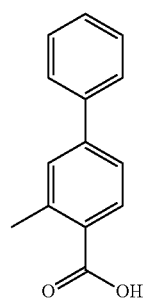

4-15

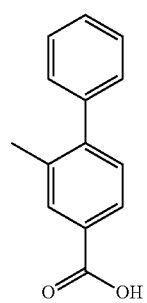

4-16

| | |
|---|---|
| 4-17 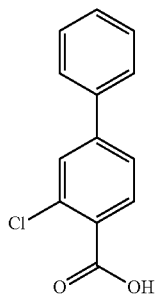 | 4-113 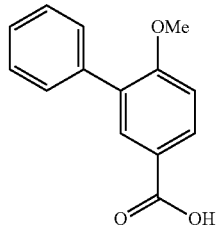 |
| 4-18 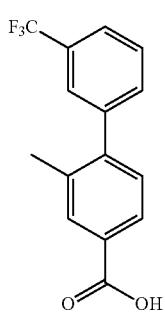 | 4-114 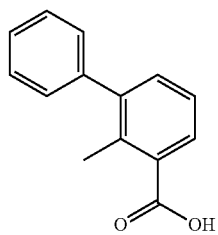 |
| 4-19 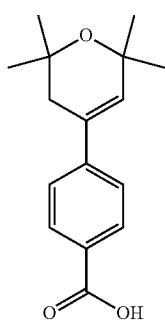 | 4-115 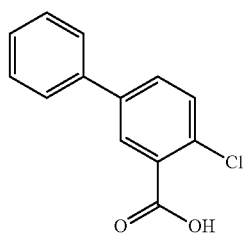 |
| 4-110 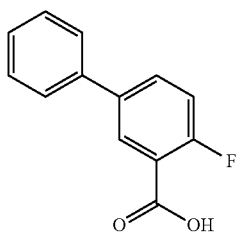 | 4-116 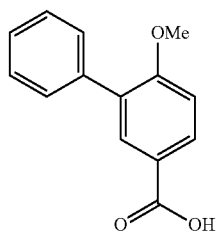 |
| 4-111 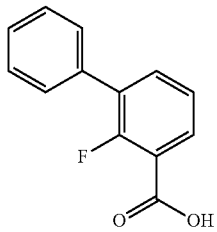 | 4-117 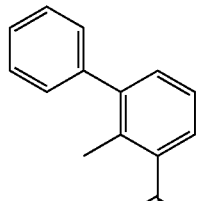 |
| 4-112 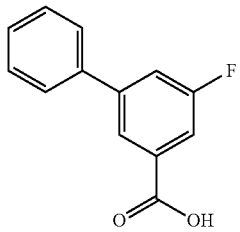 | 4-118 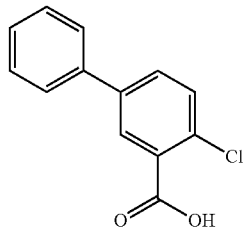 |

-continued

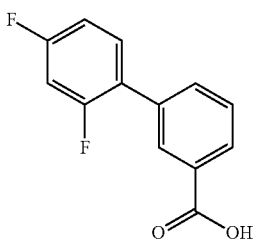
4-119

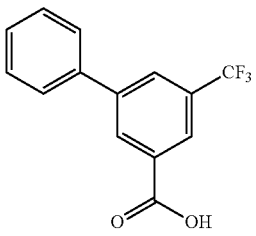
4-120

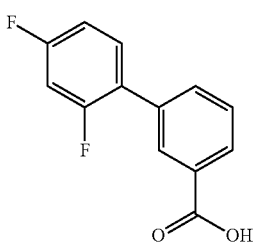
4-121

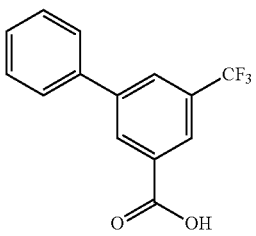
4-122

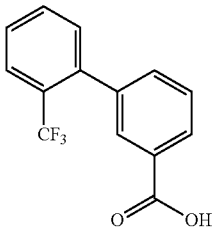
4-123

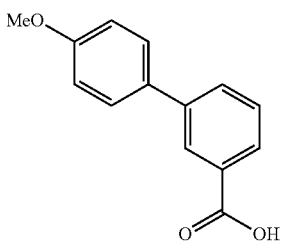
4-124

-continued

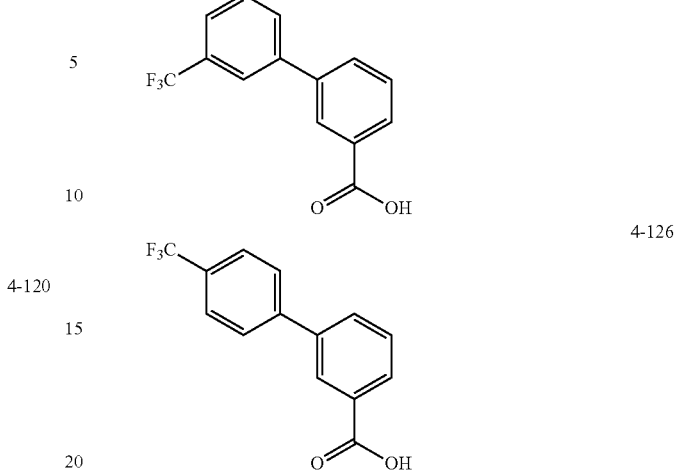

Following the procedure described above for Example 4, and substituting the appropriate reagents, starting materials and purification methods known to those skilled in the art, the following compounds of the present invention were prepared:

| Cpd | Name and data |
|---|---|
| 9 | 4-{1-[(3-Fluorobiphenyl-4-yl)carbonyl]azetidin-3-yl}-1-(1,3-thiazol-4-ylcarbonyl)piperidine. MS m/z 450.1 (M + H$^+$). |
| 10 | 1-(1,3-Thiazol-4-ylcarbonyl)-4-(1-{[3'-(trifluoromethyl)biphenyl-4-yl]carbonyl}azetidin-3-yl)piperidine. MS m/z 500.3 (M + H$^+$). |
| 11 | 4-{1-[(3'-Fluorobiphenyl-3-yl)carbonyl]azetidin-3-yl}-1-(1,3-thiazol-4-ylcarbonyl)piperidine. MS m/z 450.2 (M + H$^+$). |
| 12 | 1-(1,3-Thiazol-4-ylcarbonyl)-4-[1-({4-[5-(trifluoromethyl)thiophen-2-yl]phenyl}carbonyl)azetidin-3-yl]piperidine. MS m/z 506.1 (M + H$^+$). |
| 15 | 4-{1-[(3-Fluorobiphenyl-4-yl)carbonyl]azetidin-3-yl}-1-(1,3-thiazol-2-ylcarbonyl)piperidine. MS m/z 450.1 (M + H$^+$). |
| 17 | 4-{1-[(3'-Fluorobiphenyl-3-yl)carbonyl]azetidin-3-yl}-1-(1,3-thiazol-2-ylcarbonyl)piperidine. MS m/z 450.1 (M + H$^+$). |
| 18 | 1-(1,3-Thiazol-2-ylcarbonyl)-4-[1-({4-[5-(trifluoromethyl)thiophen-2-yl]phenyl}carbonyl)azetidin-3-yl]piperidine. MS m/z 506.1 (M + H$^+$). |
| 21 | 4-{1-[(3-Fluorobiphenyl-4-yl)carbonyl]azetidin-3-yl}-1-(1H-pyrrol-2-ylcarbonyl)piperidine. MS m/z 432.1 (M + H$^+$). |
| 22 | 1-(1H-Pyrrol-2-ylcarbonyl)-4-(1-{[3'-(trifluoromethyl)biphenyl-4-yl]carbonyl}azetidin-3-yl)piperidine. MS m/z 482.2 (M + H$^+$). |
| 23 | 4-{1-[(3'-Fluorobiphenyl-3-yl)carbonyl]azetidin-3-yl}-1-(1H-pyrrol-2-ylcarbonyl)piperidine. MS m/z 432.1 (M + H$^+$). |
| 24 | 1-(1H-Pyrrol-2-ylcarbonyl)-4-[1-({4-[5-(trifluoromethyl)thiophen-2-yl]phenyl}carbonyl)azetidin-3-yl]piperidine. MS m/z 488.3 (M + H$^+$). |
| 45 | 1-[3-Fluorobiphenyl-4-yl)carbonyl]-4-[1-(1,3-thiazol-2-ylcarbonyl)azetidin-3-yl]piperidine. MS m/z 450.1 (M + H$^+$). |
| 46 | 1-[3-Fluorobiphenyl-4-yl)carbonyl]-4-[1-(1,3-thiazol-4-ylcarbonyl)azetidin-3-yl]piperidine. MS m/z 450.1 (M + H$^+$). |
| 47 | 1-[(3-Fluorobiphenyl-4-yl)carbonyl]-4-[1-(1H-pyrrol-2-ylcarbonyl)azetidin-3-yl]piperidine. MS m/z 432.1 (M + H$^+$). |
| 48 | 4-[1-(1,3-Thiazol-2-ylcarbonyl)azetidin-3-yl]-1-{[3'-(trifluoromethyl)biphenyl-4-yl]carbonyl}piperidine. MS m/z 500.3 (M + H$^+$). |
| 49 | 4-[1-(1,3-Thiazol-4-ylcarbonyl)azetidin-3-yl]-1-{[3'-(trifluoromethyl)biphenyl-4-yl]carbonyl}piperidine. MS m/z 500.1 (M + H$^+$). |
| 50 | 4-[1-(1H-Pyrrol-2-ylcarbonyl)azetidin-3-yl]-1-{[3'-(trifluoromethyl)biphenyl-4-yl]carbonyl}piperidine. MS m/z 482.2 (M + H$^+$). |
| 51 | 1-[(3'-Fluorobiphenyl-3-yl)carbonyl]-4-[1-(1,3-thiazol-2-ylcarbonyl)azetidin-3-yl]piperidine. MS m/z 450.1 (M + H$^+$). |

37

-continued

| Cpd | Name and data |
|---|---|
| 52 | 1-[(3'-Fluorobiphenyl-3-yl)carbonyl]-4-[1-(1,3-thiazol-4-ylcarbonyl)azetidin-3-yl]piperidine.<br>MS m/z 450.1 (M + H⁺). |
| 53 | 1-[(3'-Fluorobiphenyl-3-yl)carbonyl]-4-[1-(1H-pyrrol-2-ylcarbonyl)azetidin-3-yl]piperidine.<br>MS m/z 432.1 (M + H⁺). |
| 54 | 4-[1-(1,3-Thiazol-2-ylcarbonyl)azetidin-3 -yl]-1-({4-[5-(trifluoromethyl)thiophen-2-yl]phenyl}carbonyl)piperidine.<br>MS m/z 506.1 (M + H⁺). |
| 55 | 4-[1-(1,3-Thiazol-4-ylcarbonyl)azetidin-3-yl]-1-({4-[5-(trifluoromethyl)thiophen-2-yl]phenyl}carbonyl)piperidine.<br>MS m/z 506.1 (M + H⁺). |
| 56 | 4-[1-(1H-Pyrrol-2-ylcarbonyl)azetidin-3-yl]-1-({4-[5-(trifluoromethyl)thiophen-2-yl]phenyl}carbonyl)piperidine.<br>MS m/z 488.3 (M + H⁺). |

Example 5

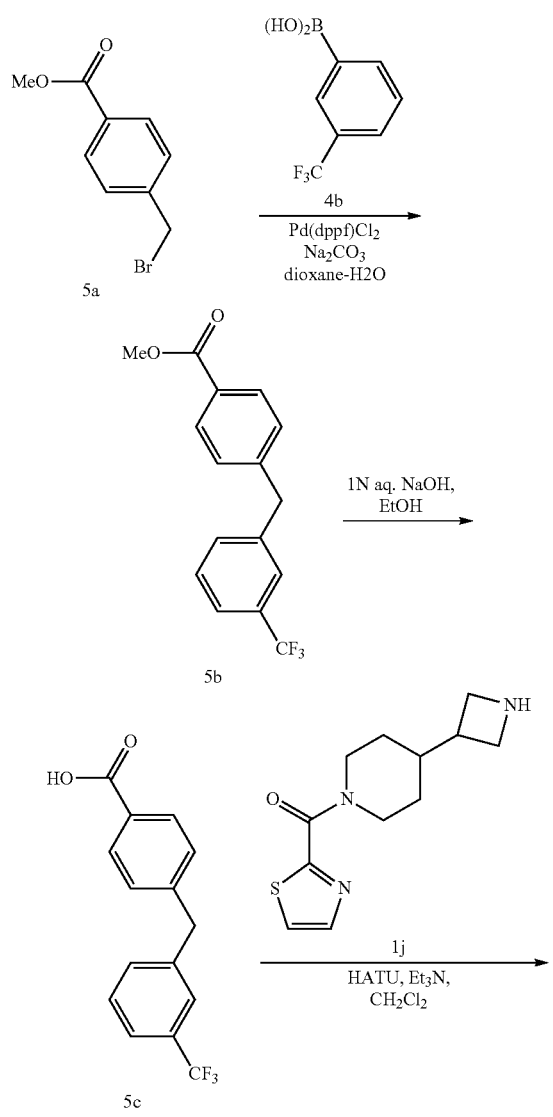

38

-continued

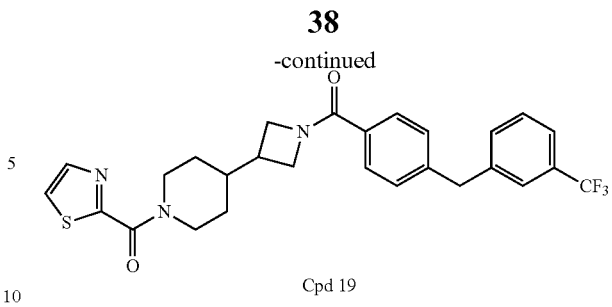

Cpd 19

A. Methyl 4-(3-(trifluoromethyl)benzyl)benzoate, 5b. A portion of Pd(dppf)Cl₂ (0.87 mmol, 0.64 g) was added to a suspension of methyl 4-(bromomethyl)benzoate 5a (8.73 mmol, 2.0 g), 3-trifluoromethylboronic acid 4b (10.5 mmol, 1.99 g), and Na₂CO₃ (17.5 mmol, 1.85 g) in 20 mL of dioxane and 5 mL of water. The mixture was stirred at 80° C. for 3 h. After cooling, the solid was collected by filtration and washed with EtOAc. The filtrate was washed with 1N aqueous HCl and brine, dried over MgSO₄, and concentrated. The crude product was purified by flash column chromatography (silica gel, 0-10% EtOAc:heptane) to give 2.2 g (85% yield) of compound 5b. MS m/z 295.2 (M+H⁺).

B. 4-(3-(Trifluoromethyl)benzyl)benzoic acid, 5c. 1N aqueous NaOH (12.9 mmol, 12.9 mL) was added to a suspension of compound 5b (6.46 mmol, 1.9 g) in 75 mL of EtOH. The mixture was stirred at 20° C. for 20 h. The reaction mixture was concentrated and the residue was acidified with 1N aqueous HCl. The resulting solid was collected by filtration and dried to afford 1.6 g (87%) of compound 5c, which was used in the next reaction without further purification. MS m/z 281.1 (M+H⁺).

C. 1-(1,3-Thiazol-2-ylcarbonyl)-4-[1-({4-[3-(trifluoromethyl)benzyl]phenyl}carbonyl)azetidin-3-yl]piperidine, Cpd 19. To a stirring solution of compound 1j mono-TFA salt (0.27 mmol, 100 mg) and compound 5c (0.30 mmol, 84 mg) in 4 mL of CH₂Cl₂ was added Et₃N (1.09 mmol, 0.15 mL). After 20 min at 20° C., HATU (0.33 mmol, 125 mg) was added and the mixture was stirred at 20° C. for 20 h. The solvent was removed and the crude residue was purified by preparative reverse-phase chromatography to give 46 mg (33% yield) of Cpd 19.

¹H NMR (CD₃OD, 400 MHz): δ=7.92 (br. s., 1H), 7.79 (d, J=3.2 Hz, 1H), 7.57-7.64 (m, J=8.1 Hz, 2H), 7.43-7.53 (m, 4H), 7.28-7.36 (m, J=8.1 Hz, 2H), 5.29 (t, J=10.0 Hz, 1H), 4.61 (t, J=10.9 Hz, 1H), 4.38 (t, J=8.6 Hz, 1H), 4.20 (t, J=9.3 Hz, 1H), 4.10 (s, 2H), 4.07-4.15 (m, 1H), 3.85-3.96 (m, 1H), 3.10-3.27 (m, 1H), 2.78-2.96 (m, 1H), 2.36-2.53 (m, 1H), 1.66-1.93 (m, 3H), 1.03-1.29 (m, 2H). MS m/z 514.2 (M+H⁺).

Following the procedure described above for Example 5 and substituting the appropriate reagents, starting materials and purification methods known to those skilled in the art, the following intermediate compound was prepared:

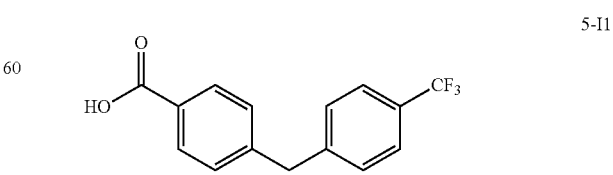

5-I1

Following the procedure described above for Example 5, and substituting the appropriate reagents, starting materials and purification methods known to those skilled in the art, the following compounds of the present invention were prepared:

| Cpd | Name and data |
|---|---|
| 13 | 1-(1,3-Thiazol-4-ylcarbonyl)-4-[1-({4-[3-(trifluoromethyl)benzyl]phenyl}carbonyl)azetidin-3-yl]piperidine.<br>MS m/z 514.2 (M + H$^+$). |
| 25 | 1-(1H-Pyrrol-2-ylcarbonyl)-4-[1-({4-3-(trifluoromethyl)benzyl]phenyl}carbonyl)azetidin-3-yl]piperidine<br>MS m/z 497.2 (M + H$^+$). |
| 27 | 1-(1,3-Thiazol-2-ylcarbonyl)-4-[1-({4-[4-(trifluoromethyl)benzyl]phenyl}carbonyl)azetidin-3-yl]piperidine<br>MS m/z 514.2 (M + H$^+$). |
| 33 | 1-(1,3-Thiazol-4-ylcarbonyl)-4-[1-({4-[4-(trifluoromethyl)benzyl]phenyl}carbonyl)azetidin-3-yl]piperidine<br>MS m/z 514.2 (M + H$^+$). |
| 39 | 1-(1H-Pyrrol-2-ylcarbonyl)-4-[1-({4-[4-(trifluoromethyl)benzyl]phenyl}carbonyl)azetidin-3-yl]piperidine<br>MS m/z 496.2 (M + H$^+$). |
| 57 | 4-[1-(1,3-Thiazol-2-ylcarbonyl)azetidin-3-yl]-1-({4-[3-(trifluoromethyl)benzyl]phenyl}carbonyl)piperidine<br>MS m/z 514.2 (M + H$^+$). |
| 58 | 4-[1-(1,3-Thiazol-4-ylcarbonyl)azetidin-3-yl]-1-({4-[3-(trifluoromethyl)benzyl]phenyl}carbonyl)piperidine<br>MS m/z 514.2 (M + H$^+$). |
| 59 | 4-[1-(1H-Pyrrol-2-ylcarbonyl)azetidin-3-yl]-1-({4-[3-(trifluoromethyl)benzyl]phenyl}carbonyl)piperidine<br>MS m/z 496.2 (M + H$^+$). |
| 63 | 4-[1-(1,3-Thiazol-2-ylcarbonyl)azetidin-3-yl]-1-({4-[4-(trifluoromethyl)benzyl]phenyl}carbonyl)piperidine<br>MS m/z 514.2 (M + H$^+$). |
| 64 | 4-[1-(1,3-Thiazol-4-ylcarbonyl)azetidin-3-yl]-1-({4-[4-(trifluoromethyl)benzyl]phenyl}carbonyl)piperidine<br>MS m/z 514.2 (M + H$^+$). |
| 65 | 4-[1-(1H-Pyrrol-2-ylcarbonyl)azetidin-3-yl]-1-({4-[4-(trifluoromethyl)benzyl]phenyl}carbonyl)piperidine<br>MS m/z 496.2 (M + H$^+$). |

Example 6

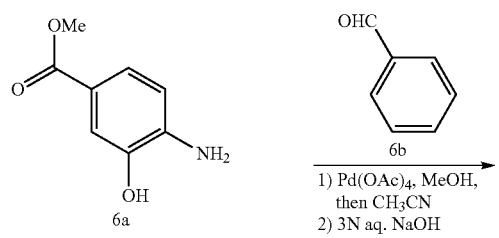

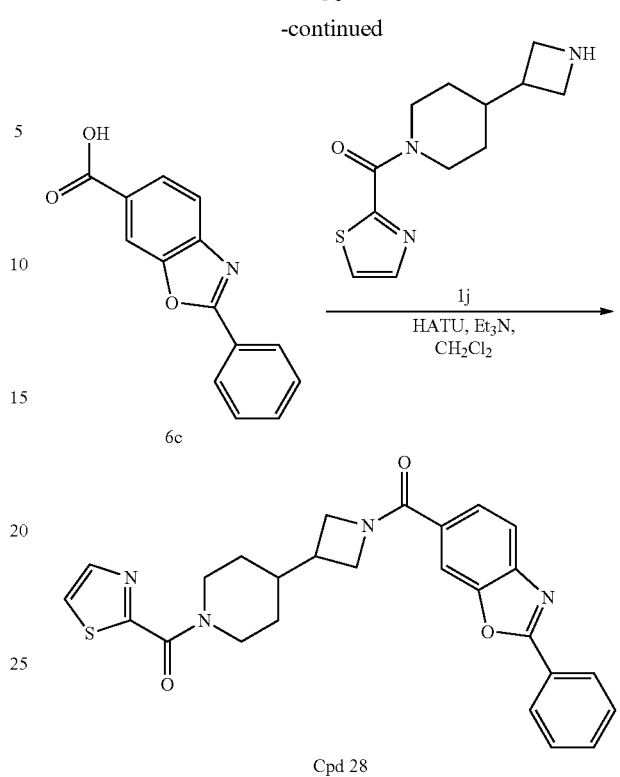

Cpd 28

A. 2-Phenylbenzo[d]oxazole-6-carboxylic acid, 6c. A solution of methyl 4-amino-3-hydroxybenzoate 6a (29.9 mmol, 5.0 g) and benzaldehyde 6b (29.9 mmol, 3.02 mL) in 150 mL of MeOH was stirred at 20° C. for 3 h. The solvent was removed under vacuum and the residue was mixed with 150 mL of acetonitrile. Lead (IV) acetate (29.9 mmol, 13.3 g) was added in one portion and the mixture was refluxed for 20 min. After cooling, the precipitate was removed by filtration and washed with acetonitrile. The filtrate and wash solutions were stirred with 3N aqueous NaOH (120 mmol, 40 mL) at 50° C. for 20 h. After cooling, the reaction mixture was acidified and filtered to give 6.0 g (79%) of compound 6c. MS m/z 240.0 (M+H$^+$).

B. 2-Phenyl-6-({3-[1-(1,3-thiazol-2-ylcarbonyl)piperidin-4-yl]azetidin-1-yl}carbonyl)-1,3-benzoxazole, Cpd 28. To a stirring solution of compound 1j (0.40 mmol, 100 mg) and compound 6c (0.44 mmol, 100 mg) in 4 mL of CH$_2$Cl$_2$ was added Et$_3$N (1.59 mmol, 0.22 mL). After 20 min at 20° C., HATU (0.48 mmol, 180 mg) was added and the mixture was stirred at 20° C. for 20 h. The solvent was removed and the crude residue was purified by preparative reverse-phase chromatography to give 75 mg (39% yield) of Cpd 28. $^1$H NMR (CD$_3$OD, 400 MHz): δ=8.23-8.32 (m, 2H), 8.01 (s, 1H), 7.89-7.97 (m, 1H), 7.77-7.85 (m, 2H), 7.73 (dd, J=8.3, 1.2 Hz, 1H), 7.54-7.68 (m, 3H), 5.30 (t, J=11.0 Hz, 1H), 4.64 (t, J=12.0 Hz, 1H), 4.43-4.54 (m, 1H), 4.18-4.34 (m, 2H), 3.92-4.05 (m, 1H), 3.16-3.29 (m, 1H), 2.84-2.99 (m, 1H), 2.47-2.60 (m, 1H), 1.72-2.02 (m, 3H), 1.10-1.34 (m, 2H). MS m/z 473.1 (M+H$^+$).

Following the procedure described above for Example 6, and substituting the appropriate reagents, starting materials and purification methods known to those skilled in the art, the following compounds of the present invention were prepared:

| Cpd | Name and data |
|---|---|
| 34 | 2-Phenyl-6-({3-[1-(1,3-thiazol-4-ylcarbonyl)piperidin-4-yl]azetidin-1-yl}carbonyl)-1,3-benzoxazole. MS m/z 473.1 (M + H⁺). |
| 40 | 2-Phenyl-6-({3-[1-(1H-pyrrol-2-ylcarbonyl)piperidin-4-yl]azetidin-1-yl}carbonyl)-1,3-benzoxazole. MS m/z 455.3 (M + H⁺). |
| 66 | 2-Phenyl-6-({4-[1-(1,3-thiazol-2-ylcarbonyl)azetidin-3-yl]piperidin-1-yl}carbonyl)-1,3-benzoxazole. MS m/z 473.1 (M + H⁺). |
| 67 | 2-Phenyl-6-({4-[1-(1,3-thiazol-4-ylcarbonyl)azetidin-3-yl]piperidin-1-yl}carbonyl)-1,3-benzoxazole. MS m/z 473.1 (M + H⁺). |
| 68 | 2-Phenyl-6-({4-[1-(1H-pyrrol-2-ylcarbonyl)azetidin-3-yl]piperidin-1-yl}carbonyl)-1,3-benzoxazole. MS m/z 455.3 (M + H⁺). |

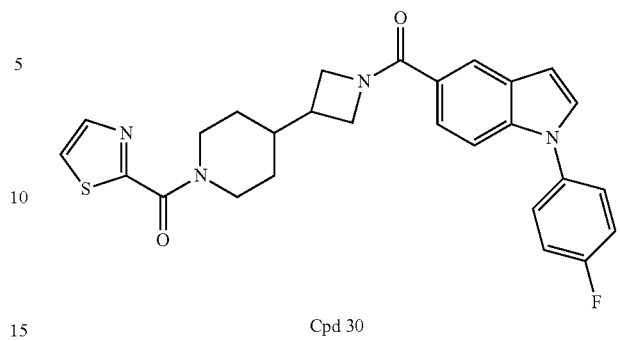

Cpd 30

Example 7

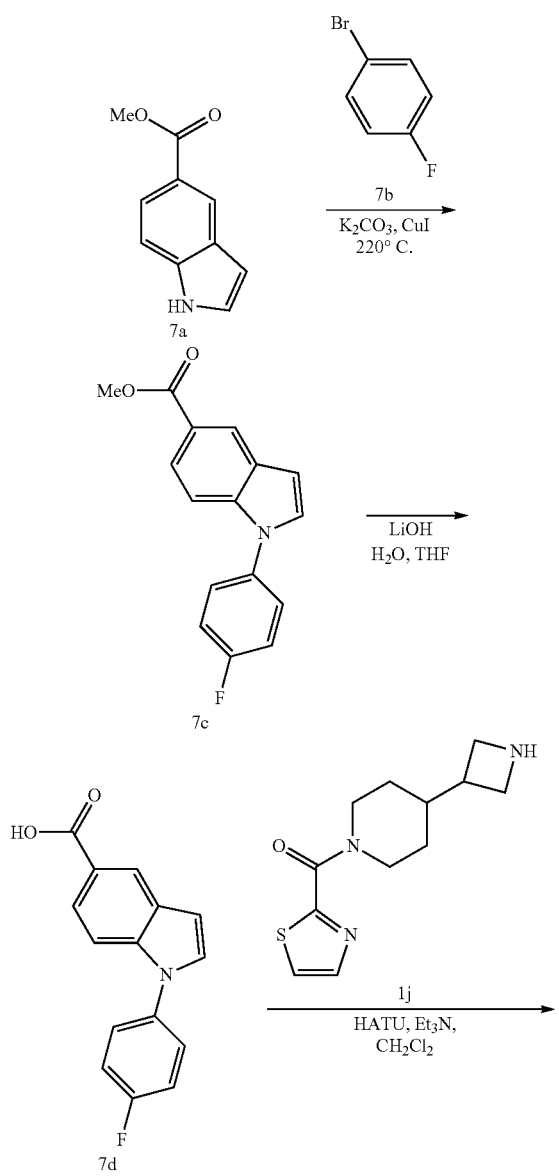

A. Methyl 1-(4-fluorophenyl)-indole-5-carboxylate, 7c. A mixture of methyl indole-5-carboxylate 7a (0.5 g, 2.85 mmol), 1-bromo-4-fluoro-benzene 7b (2 mL, 18.21 mmol), CuI (0.544 g, 2.85 mmol), and $K_2CO_3$ (0.591 g, 4.28 mmol) was heated in a microwave reactor at 220° C. for 2.5 h. The reaction mixture was diluted with $CH_2Cl_2$ and filtered. The solution was concentrated and the residue was purified by flash column chromatography (silica gel, 15% EtOAc/heptane) to give 0.58 g of compound 7c. MS m/z 270.1 (M+H⁺).

B. 1-(4-Fluorophenyl)-indole-5-carboxylic acid, 7d. A mixture of methyl 1-(4-fluorophenyl)-indole-5-carboxylate 7c (0.58 g, 2.15 mmol) and LiOH $H_2O$ (0.36 g, 8.6 mmol) in THF (15 mL) and $H_2O$ (10 mL) was stirred at room temperature for 5 days. Aqueous 10% HCl solution was added to the reaction mixture to adjust pH=3~4. The resulting mixture was extracted with EtOAc (2×). The organic solution was washed with aq. NaCl, dried over $Na_2SO_4$ and concentrated to give 0.5 g of compound 7d. MS m/z 256.2 (M+H⁺).

C. 1-(4-Fluorophenyl)-5-({3-[1-(1,3-thiazol-2-ylcarbonyl)piperidin-4-yl]azetidin-1-yl}carbonyl)-1H-indole, Cpd 30. To a stirring solution of compound 1j (0.40 mmol, 100 mg) and compound 7d (0.44 mmol, 110 mg) in 4 mL of $CH_2Cl_2$ was added $Et_3N$ (1.59 mmol, 0.22 mL). After 20 min at 20° C., HATU (0.48 mmol, 180 mg) was added and the mixture was stirred at 20° C. for 20 h. The solvent was removed and the crude residue was purified by preparative reverse-phase chromatography to give 165 mg (85% yield) of Cpd 30. ¹H NMR (CD₃OD, 400 MHz): δ=7.99 (s, 1H), 7.92 (br. s., 1H), 7.79 (d, J=3.2 Hz, 1H), 7.44-7.58 (m, 5H), 7.30 (t, J=8.7 Hz, 2H), 6.77 (d, J=3.4 Hz, 1H), 5.28 (br. s., 1H), 4.53-4.69 (m, 1H), 4.39-4.51 (m, 1H), 4.10-4.29 (m, 2H), 3.95 (br. s., 1H), 3.10-3.27 (m, 1H), 2.89 (t, J=10.5 Hz, 1H), 2.33-2.56 (m, 1H), 1.65-1.98 (m, J=10.8 Hz, 3H), 1.19 (br. s., 2H). MS m/z 489.1 (M+H⁺).

Following the procedure described above for Example 7, and substituting the appropriate reagents, starting materials, and purification methods known to those skilled in the art, the following intermediate compounds were prepared:

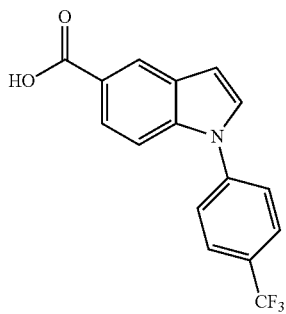
7-I1

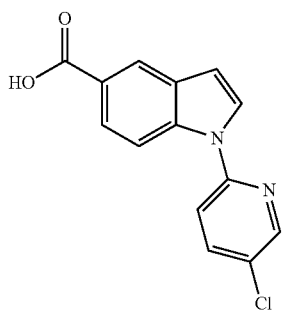
7-I2

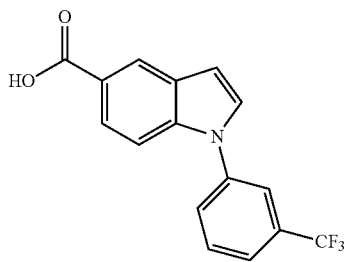
7-I3

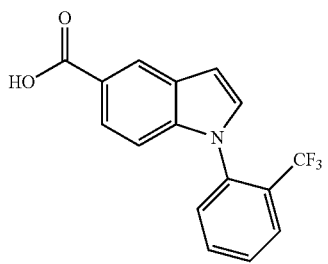
7-I4

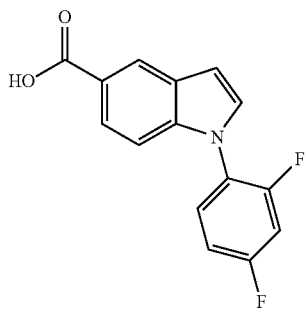
7-I5

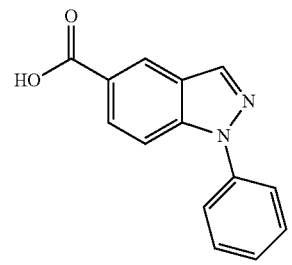
7-I6

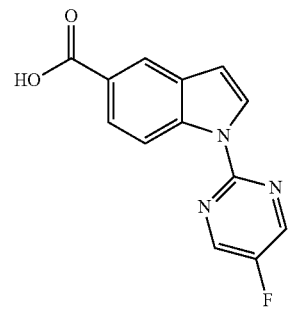
7-I7

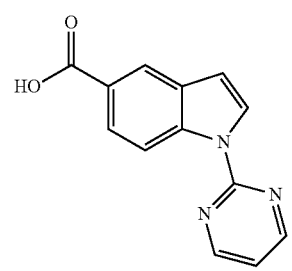
7-I8

Following the procedure described above for Example 7, and substituting the appropriate reagents, starting materials, and purification methods known to those skilled in the art, the following compounds of the invention were prepared:

| Cpd | Name and data |
|---|---|
| 31 | 5-({3-[1-(1,3-Thiazol-2-ylcarbonyl)piperidin-4-yl]azetidin-1-yl}carbonyl)-1-[4-(trifluoromethyl)phenyl]-1H-indole. MS m/z 539.1 (M + H$^+$). |
| 36 | 1-(4-Fluorophenyl)-5-({3-[1-(1,3-thiazol-4-ylcarbonyl)piperidin-4-yl]azetidin-1-yl}carbonyl)-1H-indole. MS m/z 489.1 (M + H$^+$). |
| 37 | 5-({3-[1(1,3-Thiazol-4-ylcarbonyl)piperidin-4-yl]azetidin-1-yl}carbonyl)-1-[4-(trifluoromethyl)phenyl]-1H-indole. MS m/z 539.2 (M + H$^+$). |
| 42 | 1-(4-Fluorophenyl)-5-({3-[1-(1H-pyrrol-2-ylcarbonyl)piperidin-4-yl]azetidin-1-yl}carbonyl)-1H-indole. MS m/z 472.2 (M + H$^+$). |
| 43 | 5-({3-[1-(1H-Pyrrol-2-ylcarbonyl)piperidin-4-yl]azetidin-1-yl}carbonyl)-1-[4-(trifluoromethyl)phenyl]-1H-indole. MS m/z 521.3 (M + H$^+$). |
| 72 | 1-(4-Fluorophenyl)-5-({4-[1-(1,3-thiazol-2-ylcarbonyl)azetidin-3-yl]piperidin-1-yl}carbonyl)-1H-indole. MS m/z 489.1 (M + H$^+$). |
| 73 | 1-(4-Fluorophenyl)-5-({4-[1-(1,3-thiazol-4-ylcarbonyl)azetidin-3-yl]piperidin-1-yl}carbonyl)-1H-indole. MS m/z 489.1 (M + H$^+$). |
| 74 | 1-(4-Fluorophenyl)-5-({4-[1-(1H-pyrrol-2-ylcarbonyl)azetidin-3-yl]piperidin-1-yl}carbonyl)-1H-indole. MS m/z 471.3 (M + H$^+$). |
| 75 | 5-({4-[1(1,3-Thiazol-2-ylcarbonyl)azetidin-3-yl]piperidin-1-yl}carbonyl)-1-[4-(trifluoromethyl)phenyl]-1H-indole. MS m/z 539.2 (M + H$^+$). |
| 76 | 5-({4-[1(1,3-Thiazol-4-ylcarbonyl)azetidin-3-yl]piperidin-1-yl}carbonyl)-1-[4-(trifluoromethyl)phenyl]-1H-indole. MS m/z 539.2 (M + H$^+$). |

| Cpd | Name and data |
|---|---|
| 77 | 5-({4-[1-(1H-Pyrrol-2-ylcarbonyl)azetidin-3-yl]piperidin-1-yl}carbonyl)-1-[4-(trifluoromethyl)phenyl]-1H-indole. MS m/z 521.3 (M + H⁺). |
| 93 | 1-(5-Chloropyridin-2-yl)-5-({3-[1-(1,3-thiazol-2-ylcarbonyl)piperidin-4-yl]azetidin-1-yl}carbonyl)-1H-indole. $^1$H NMR (CDCl$_3$) δ = 8.51 (d, J = 2.5 Hz, 1H), 8.23 (d, J = 8.8 Hz, 1H), 7.95 (d, J = 1.4 Hz, 1H), 7.87 (br. s., 1H), 7.81 (dd, J = 8.7, 2.6 Hz, 1H), 7.70 (d, J = 3.5 Hz, 1H), 7.59 (dd, J = 8.7, 1.5 Hz, 1H), 7.53 (d, J = 3.2 Hz, 1H), 7.45 (d, J = 8.7 Hz, 1H), 6.77 (dd, J = 2.9, 0.6 Hz, 1H), 5.40-5.54 (m, 1H), 4.73 (t, J = 9.8 Hz, 1H), 4.37-4.49 (m, 1H), 4.21-4.32 (m, 1H), 4.03-4.12 (m, 1H), 3.93-4.03 (m, 1H), 3.57-3.72 (m, 1H), 3.06-3.22 (m, 1H), 2.36-2.51 (m, 1H), 1.67-1.94 (m, 3H), 1.10-1.32 (m, 2H). MS m/z 506 (M + H⁺). |

Example 8

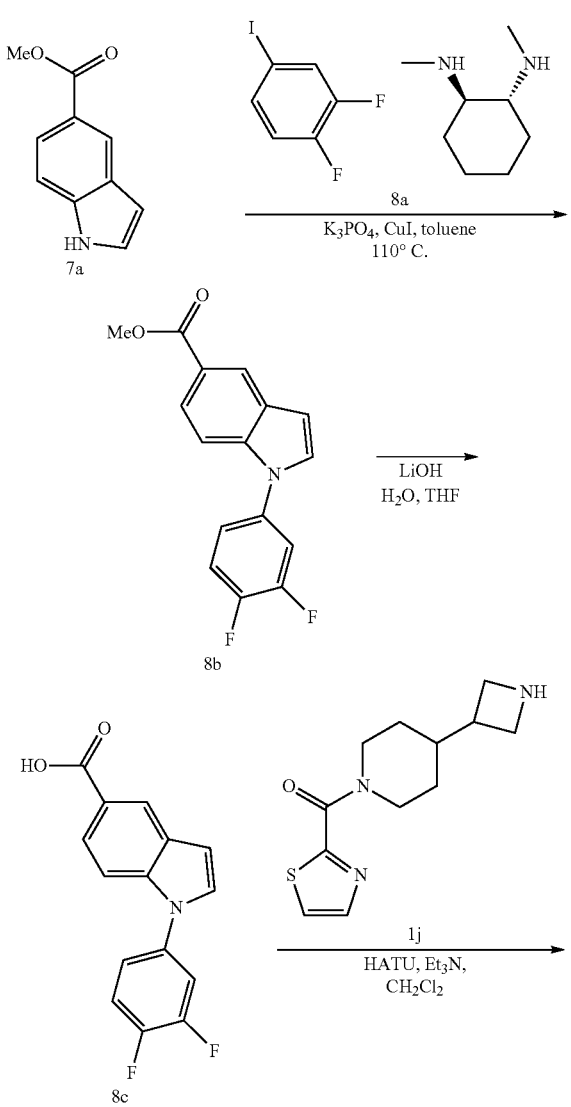

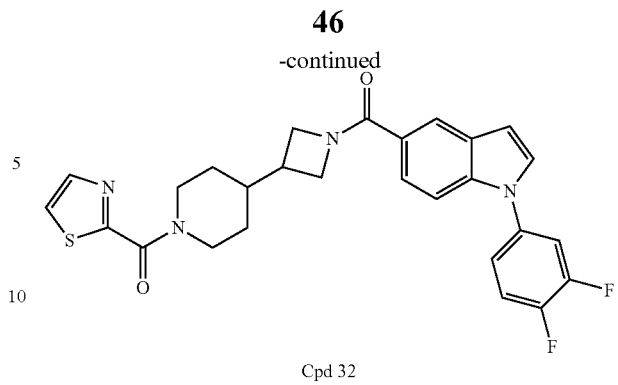

Cpd 32

A. Methyl 1-(3,4-difluorophenyl)-indole-5-carboxylate, 8b. A mixture of methyl indole-5-carboxylate 7a (2 g, 11.4 mmol), 1-iodo-3,4-difluoro-benzene 8a (1.5 mL, 12.5 mmol), CuI (0.22 g, 1.14 mmol), trans-N,N'-dimethylcyclohexane-1,2-diamine (0.54 mL, 3.43 mmol), and K$_3$PO$_4$ (6.06 g, 28.5 mmol) in toluene (12 mL) was heated at 110° C. for 7 h. The reaction mixture was diluted with CH$_2$Cl$_2$ and filtered. The solution was concentrated and the residue was purified by flash column chromatography (silica gel, 20% EtOAc/heptane) to give 3.0 g of compound 8b. MS m/z 288.1 (M+H⁺).

B. 1-(3,4-Difluorophenyl)-indole-5-carboxylic acid, 8c. A mixture of methyl 1-(3,4-difluorophenyl)-indole-5-carboxylate 8b (3.0 g, 10.4 mmol) and LiOH (1.0 g, 41.8 mmol) in THF (120 mL) and H$_2$O (60 mL) was stirred at room temperature for 5 days. Aqueous 10% HCl solution was added to the reaction mixture to adjust pH=3~4. The resulting mixture was extracted with EtOAc (2×). The organic solution was washed with brine, dried over Na$_2$SO$_4$ and concentrated to give 2.85 g of compound 8c. MS m/z 274.2 (M+H⁺).

C. 1-(3,4-Difluorophenyl)-5-({3-[4-(1,3-thiazol-2-ylcarbonyl)piperazin-1-yl]azetidin-1-yl}carbonyl)-1H-indole, Cpd 32. To a stirring solution of compound 1j (0.40 mmol, 100 mg) and compound 8c (0.44 mmol, 120 mg) in 4 mL of CH$_2$Cl$_2$ was added Et$_3$N (1.59 mmol, 0.22 mL). After 20 min at 20° C., HATU (0.48 mmol, 180 mg) was added and the mixture was stirred at 20° C. for 20 h. The solvent was removed and the crude residue was purified by preparative reverse-phase chromatography to give 118 mg (58% yield) of Cpd 32. $^1$H NMR (CD$_3$OD, 400 MHz): δ=8.00 (s, 1H), 7.93 (br. s., 1H), 7.81 (d, J=2.9 Hz, 1H), 7.51-7.60 (m, 4H), 7.44-7.52 (m, 1H), 7.33-7.42 (m, 1H), 6.79 (d, J=3.2 Hz, 1H), 5.22-5.38 (m, 1H), 4.55-4.71 (m, 1H), 4.48 (t, J=8.8 Hz, 1H), 4.14-4.33 (m, 2H), 3.89-4.04 (m, 1H), 3.14-3.28 (m, 1H), 2.83-2.99 (m, 1H), 2.43-2.58 (m, 1H), 1.70-2.00 (m, 3H), 1.09-1.32 (m, 2H). MS m/z 507.1 (M+H⁺).

Following the procedure described above for Example 8, and substituting the appropriate reagents, starting materials, and purification methods known to those skilled in the art, the following intermediate compounds were prepared:

8-11

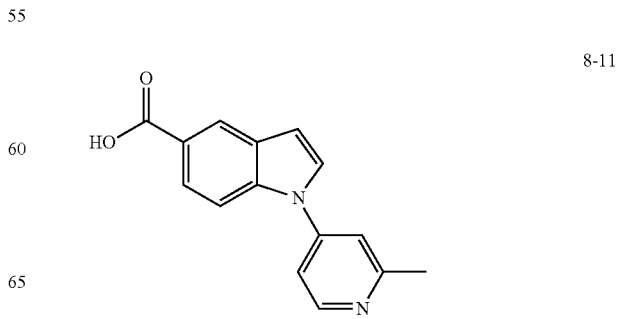

8-12 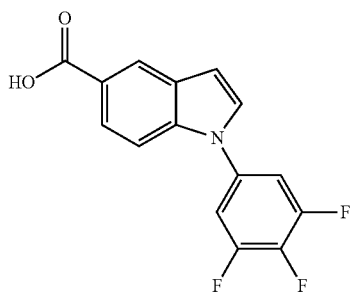
8-13 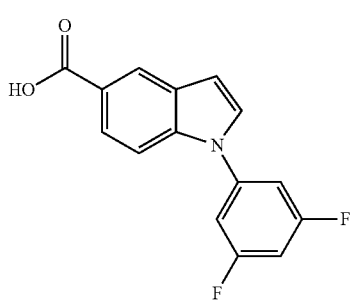
8-14 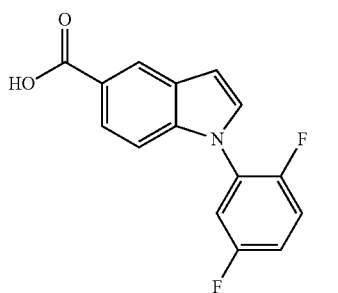
8-15 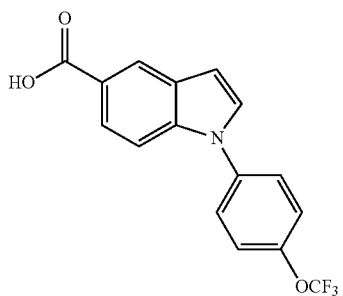
8-16 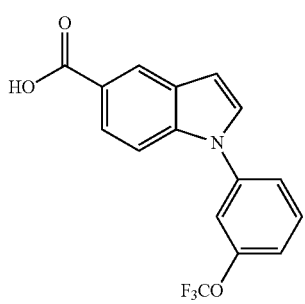
8-17 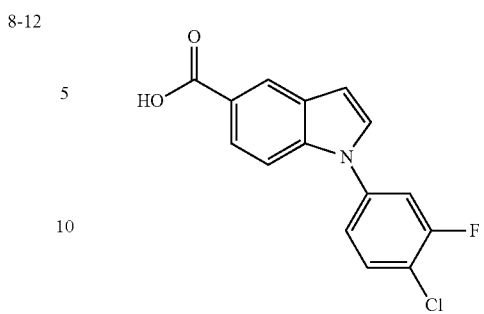
8-18 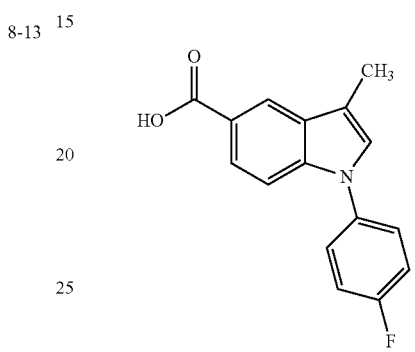
8-19 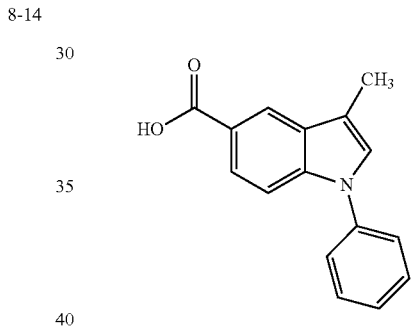
8-110 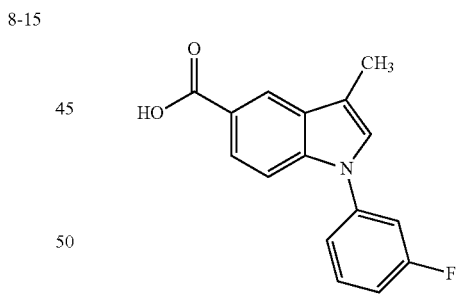
8-111 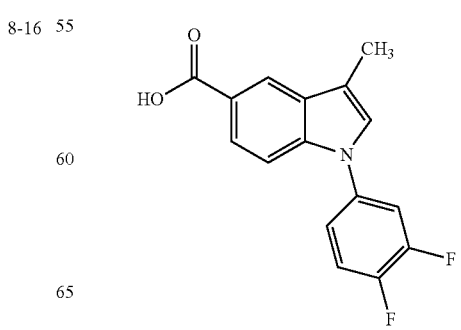

8-112 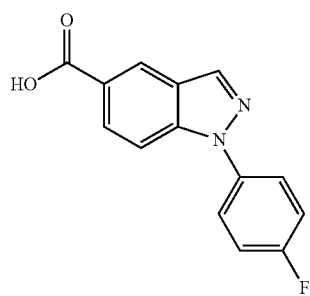
8-113 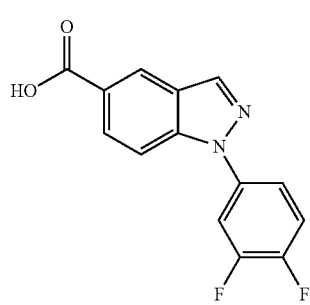
8-114 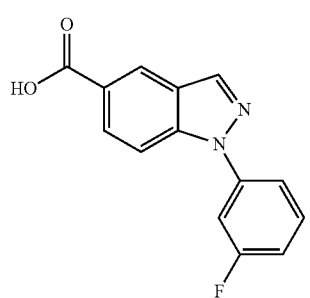
8-115 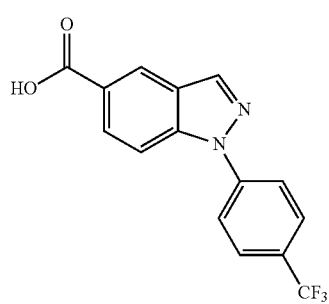
8-116 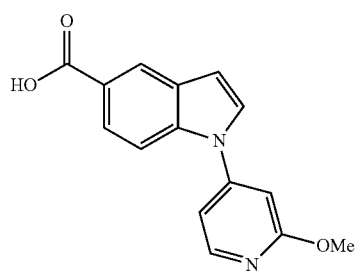
8-117 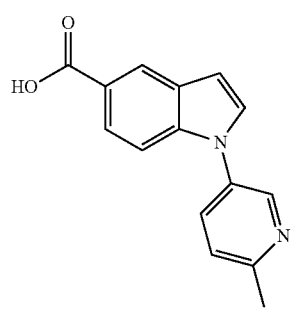
8-118 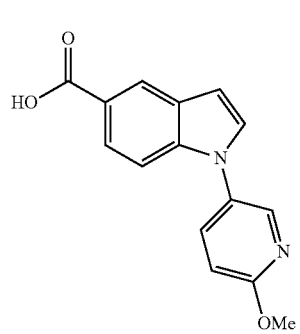
8-119 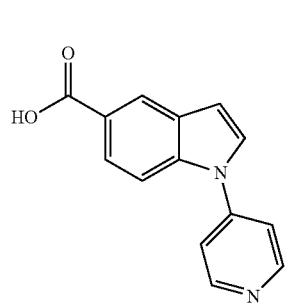
8-120 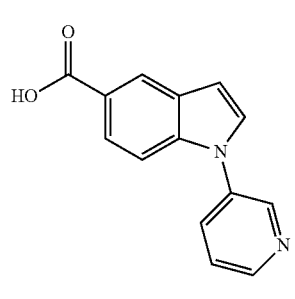
8-121 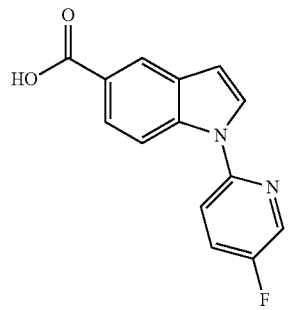

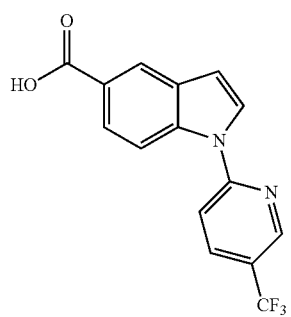
8-122
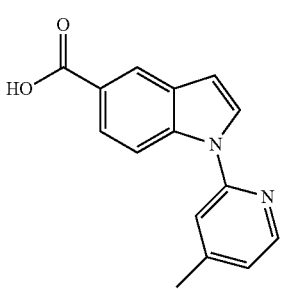
8-127
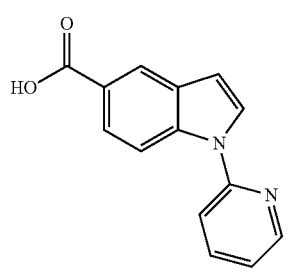
8-123
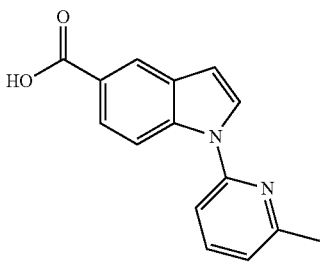
8-128
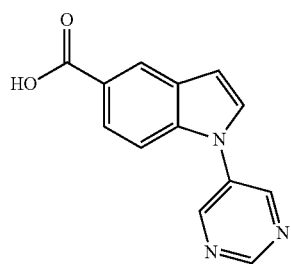
8-124
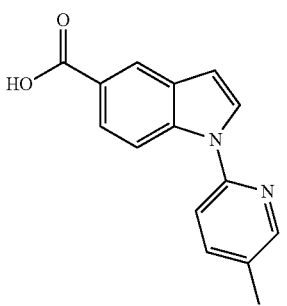
8-129
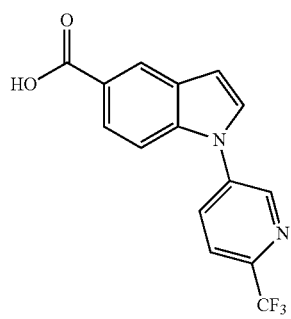
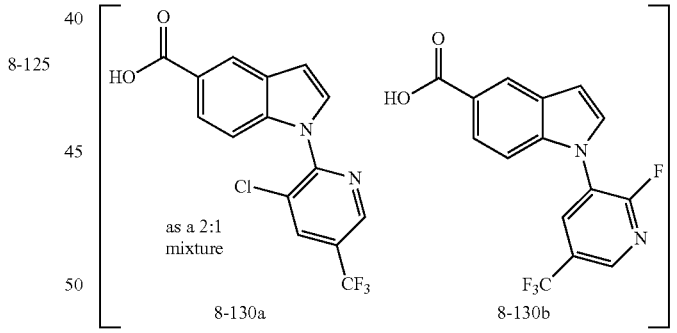
as a 2:1 mixture
8-125
8-130a    8-130b
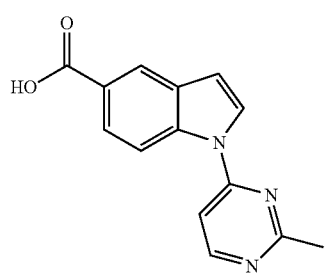
8-126
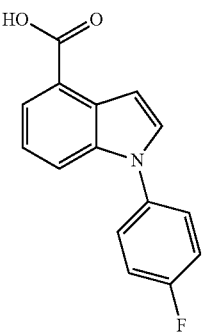
8-131

| | |
|---|---|
| 8-132 | 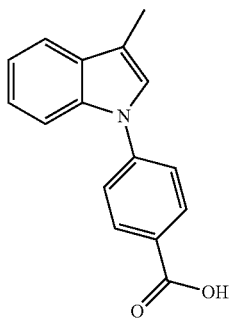 |
| 8-133 | 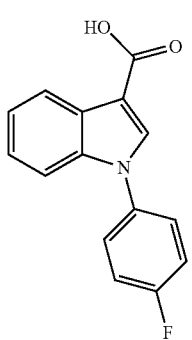 |
| 8-134 | 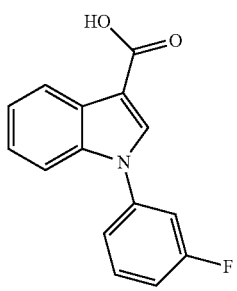 |
| 8-135 | 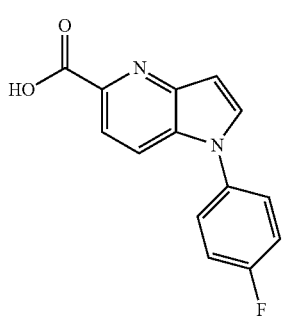 |
| 8-136 | 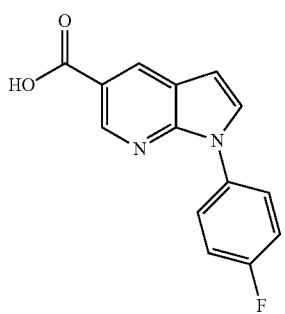 |
| 8-137 | 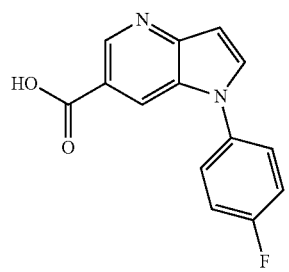 |

Following the procedure described above for Example 8, and substituting the appropriate reagents, starting materials, and purification methods known to those skilled in the art, the following compounds of the present invention were prepared:

| Cpd | Name and data |
|---|---|
| 38 | 1-(3,4-Difluorophenyl)-5-({3-[1-(1,3-thiazol-4-ylcarbonyl)piperidin-4-yl]azetidin-1-yl}carbonyl)-1H-indole). MS m/z 507.1 (M + H⁺). |
| 44 | 1-(3,4-Difluorophenyl)-5-({3-[1-(1H-pyrrol-2-ylcarbonyl)piperidin-4-yl]azetidin-1-yl}carbonyl)-1H-indole). MS m/z 489.3 (M + H⁺). |
| 78 | 1-(3,4-Difluorophenyl)-5-({4-[1-(1,3-thiazol-2-ylcarbonyl)azetidin-3-yl]piperidin-1-yl}carbonyl)-1H-indole. MS m/z 507.1 (M + H⁺). |
| 79 | 1-(3,4-Difluorophenyl)-5-({4-[1-(1,3-thiazol-4-ylcarbonyl)azetidin-3-yl]piperidin-1-yl}carbonyl)-1H-indole. MS m/z 507.1 (M + H⁺). |
| 80 | 1-(3,4-Difluorophenyl)-5-({4-[1-(1H-pyrrol-2-ylcarbonyl)azetidin-3-yl]piperidin-1-yl}carbonyl)-1H-indole. MS m/z 489.2 (M + H⁺). |
| 95 | 1-(2-Methylpyridin-4-yl)-5-({3-[1-(1,3-thiazol-2-ylcarbonyl)piperidin-4-yl]azetidin-1-yl}carbonyl)-1H-indole. ¹H NMR (CDCl₃) δ = 8.63 (d, J = 5.4 Hz, 1H), 8.00 (s, 1H), 7.87 (br. s., 1H), 7.70 (d, J = 8.7 Hz, 1H), 7.61 (dd, J = 8.7, 1.4 Hz, 1H), 7.53 (d, J = 3.1 Hz, 1H), 7.44 (d, J = 3.4 Hz, 1H), 7.24-7.36 (m, 2H), 6.79 (d, J = 3.3 Hz, 1H), 5.50 (d, J = 12.5 Hz, 1H), 4.64-4.84 (m, 1H), 4.37-4.53 (m, 1H), 4.21-4.37 (m, 1H), 3.91-4.14 (m, 2H), 3.06-3.25 (m, 1H), 2.73-2.89 (m, 1H), 2.67 (s, 3H), 2.46 (d, J = 8.1 Hz, 1H), 1.65-1.94 (m, 3H), 1.09-1.35 (m, 2H). |

Example 9

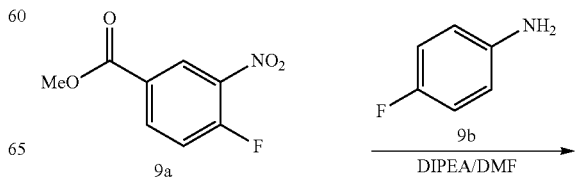

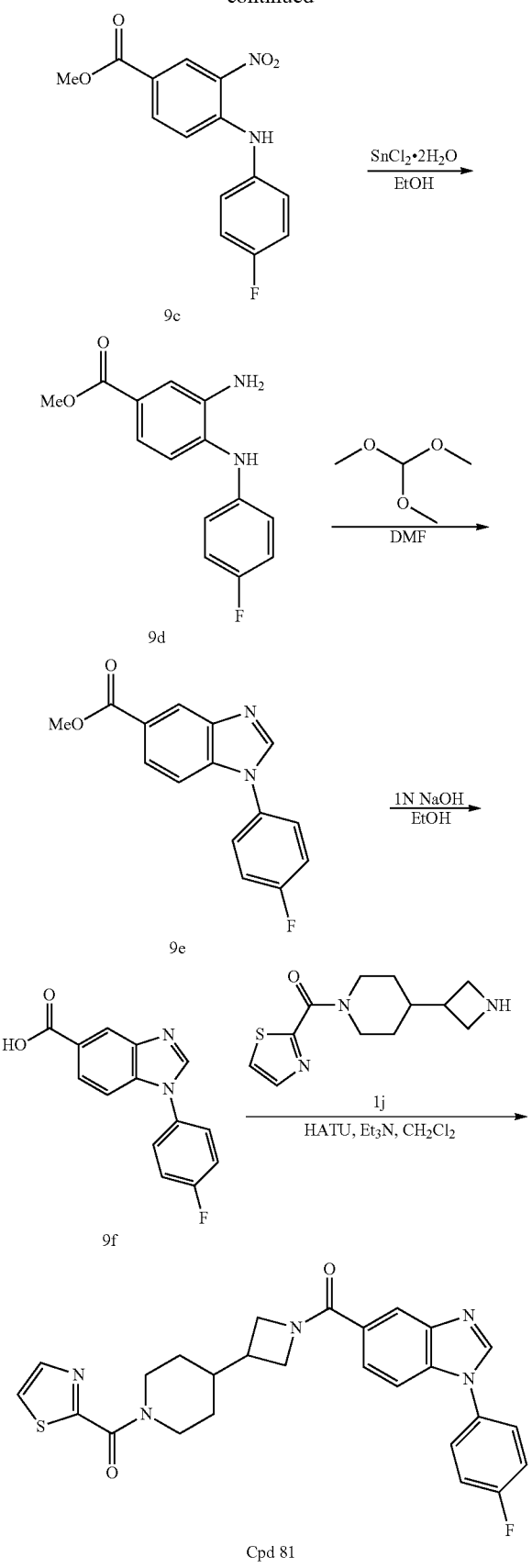

A. Methyl 4-((4-fluorophenyl)amino)-3-nitrobenzoate, 9c. A mixture of methyl 4-fluoro-3-nitrobenzoate 9a (1 g, 5.02 mmol), 4-fluoroaniline 9b (4.34 mL, 5.02 mmol), and DIPEA (1.04 mL, 6.03 mmol) in DMF (10 mL) was stirred at room temperature for 2 h. Water was added to the mixture, the resulting solid was collected by filtration, washed with water, and dried. The crude compound 9c was used in the next reaction without further purification.

B. Methyl 3-amino-4-((4-fluorophenyl)amino)benzoate, 9d. A mixture of compound 9c (1.4 g, 4.8 mmol) and $SnCl_2 \cdot 2H_2O$ (4.9 g, 21.7 mmol) in EtOH (50 mL) was stirred at 80° C. After 4 h, the mixture was cooled to room temperature and was slowly added to saturated aqueous $NaHCO_3$. The solid was collected by filtration and washed with $H_2O$. The solid was triturated with EtOAc and the filtrate was concentrated. The crude compound 9d was used in the next reaction without further purification. MS m/z 261.1 (M+H$^+$).

C. Methyl 1-(4-fluorophenyl)-1H-benzo[d]imidazole-5-carboxylate, 9e. A mixture of compound 9d (0.18 g, 0.693 mmol) and trimethyl orthoformate (0.7 mL, 6.39 mmol) in DMF (2 mL) was refluxed for 5 h and then cooled to room temperature. Water was added to the mixture. The resulting solid was collected by filtration, washed with water, and dried. The crude compound 9e was used in the next reaction without further purification. MS m/z 271.1 (M+H$^+$).

D. 1-(4-Fluorophenyl)-1H-benzo[d]imidazole-5-carboxylic acid, 9f. To a solution of compound 9e (0.18 g, 0.666 mmol) in EtOH (10 mL) was added 1N aqueous NaOH (2.5 mL, 2.5 mmol). The mixture was stirred at room temperature for 4 d. The solvent was evaporated and 1N aqueous HCl was added, followed by extraction with EtOAc. The organic layer was dried over $MgSO_4$ and concentrated. The crude compound 9f was purified by preparative reverse phase chromatography. MS m/z 257.1 (M+H$^+$).

E. 1-(4-Fluorophenyl)-5-({3-[1-(1,3-thiazol-2-ylcarbonyl)piperidin-4-yl]azetidin-1-yl}carbonyl)-1H-benzimidazole, Cpd 81. To a solution of compound 1j (0.058 g, 0.178 mmol) and HATU (0.081 g, 0.214 mmol) in 3 mL of $CH_2Cl_2$ was added $Et_3N$ (0.099 mL, 0.713 mmol). The mixture was stirred at 20° C. for 30 min, and then compound 9f (0.050 g, 0.196 mmol) was added. The reaction mixture was stirred at 20° C. for 20 h. Water (6 mL) was added and the mixture was extracted with EtOAc. The organic layer was dried over $MgSO_4$ and concentrated. The crude product was purified by preparative reverse phase chromatography to give 46 mg (47% yield) of Cpd 81. $^1$H NMR (CD$_3$OD) δ=8.14 (s, 1H), 7.93 (br. s., 1H), 7.78-7.84 (m, 2H), 7.67-7.78 (m, 3H), 7.45 (t, J=8.7 Hz, 2H), 5.23-5.38 (m, 1H), 4.57-4.71 (m, 1H), 4.44-4.54 (m, 1H), 4.29 (t, J=9.7 Hz, 1H), 4.22 (br. s., 1H), 4.00 (br. s., 1H), 3.17-3.27 (m, 1H), 2.85-2.99 (m, 1H), 2.48-2.61 (m, 1H), 1.70-2.02 (m, 3H), 1.09-1.34 (m, 2H) MS m/z 490.2 (M+H$^+$).

Following the procedure described above for Example 9 and substituting the appropriate reagents, starting materials and purification methods known to those skilled in the art, the following intermediate compounds were prepared.

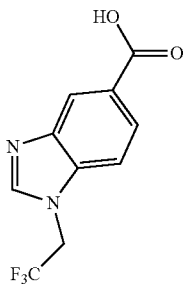

9-I1

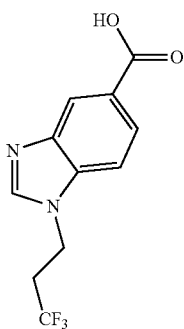

9-I2

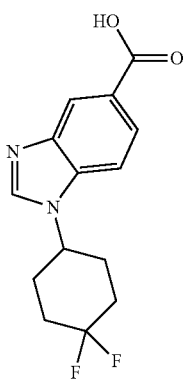

9-I3

9-I4

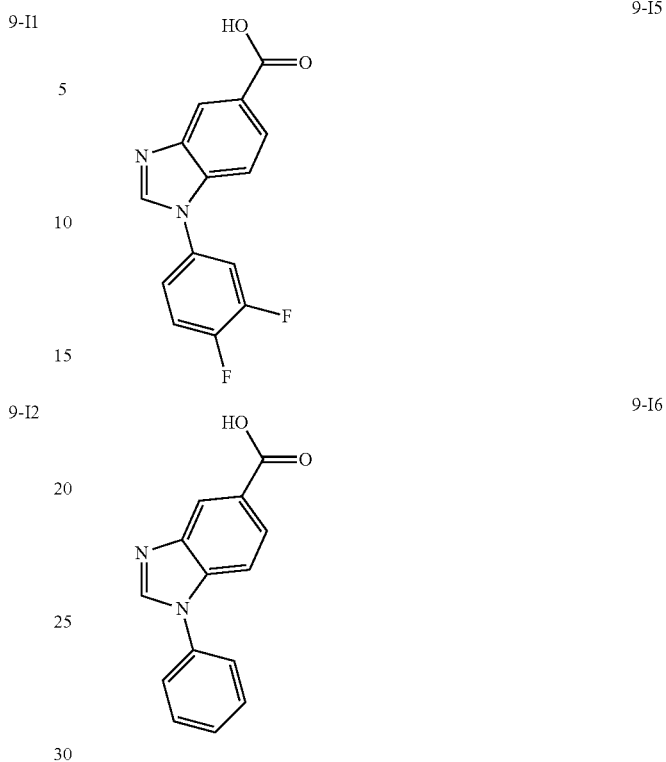

9-I5

9-I6

Following the procedure described above for Example 9 and substituting the appropriate reagents, starting materials and purification methods known to those skilled in the art, the following compounds of the present invention were prepared:

| Cpd | Name and data |
|---|---|
| 82 | 1-(3,4-Difluorophenyl)-5-({3-[1-(1,3-thiazol-2-ylcarbonyl)piperidin-4-yl]azetidin-1-yl}carbonyl)-1H-benzimidazole. MS m/z 508.2 (M + H⁺). |
| 83 | 5-({30[1-(1,3-Thiazol-2-ylcarbonyl)piperidin-4-yl]azetidin-1-yl}carbonyl)-1-[4-(trifluoromethyl)phenyl]-1H-benzimidazole. MS m/z 540.2 (M + H⁺). |
| 84 | 5-({3-[1-(1,3-Thiazol-2-ylcarbonyl)piperidin-4-yl]azetidin-1-yl}carbonyl)-1-(2,2,2-trifluoroethyl)-1H-benzimidazole. MS m/z 478.2 (M + H⁺). |
| 85 | 5-({3-[1-(1,3-Thiazol-2-ylcarbonyl)piperidin-4-yl]azetidin-1-yl}carbonyl)-1-(3,3,3-trifluoropropyl)-1H-benzimidazole. MS m/z 492.1 (M + H⁺). |

Example 10

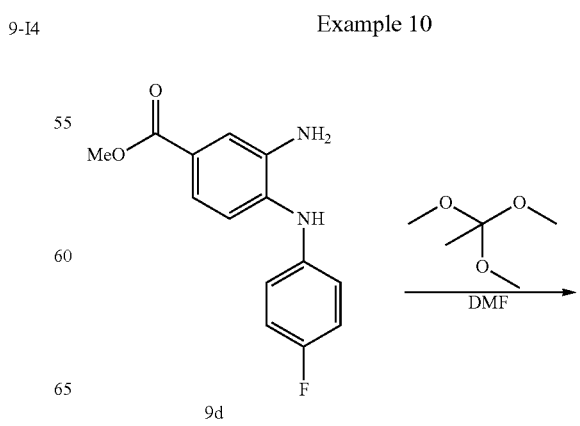

9d

-continued

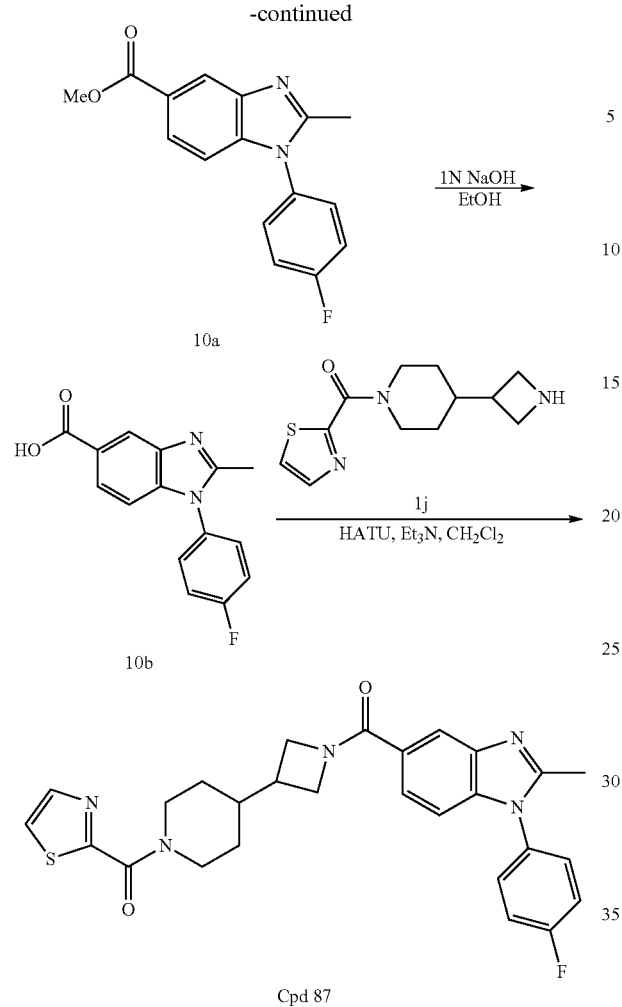

Following the procedure described above for Example 10 and substituting the appropriate reagents, starting materials and purification methods known to those skilled in the art, the following intermediate compounds were prepared:

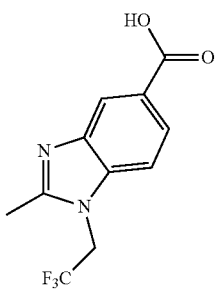

10-I1

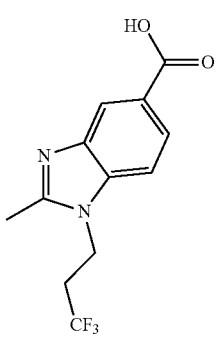

10-I2

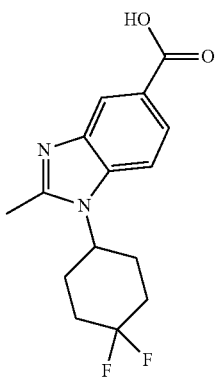

10-I3

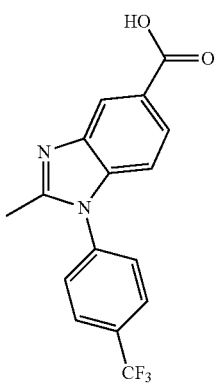

10-I4

A. Methyl 2-methyl-1-(4-fluorophenyl)-1H-benzo[d]imidazole-5-carboxylate, 10a. The title compound 10a was prepared using the method described in Example 9, substituting trimethyl orthoacetate for trimethyl orthoformate in Step C. The crude compound 10a was used in the next reaction without further purification. MS m/z 285.1 (M+H$^+$).

B. 2-Methyl-1-(4-fluorophenyl)-1H-benzo[d]imidazole-5-carboxylate, 10b. The title compound 10b was prepared using the method described in Example 9, substituting compound 10a for compound 9e in Step D. The crude product 10b was used in the next reaction without further purification. MS m/z 271.2 (M+H$^+$).

C. 1-(4-Fluorophenyl)-2-methyl-5-({3-[1-(1,3-thiazol-2-ylcarbonyl)piperidin-4-yl]azetidin-1-yl}carbonyl)-1H-benzimidazole, Cpd 87. The title compound Cpd 87 was prepared using the method described in Example 9, substituting compound 10b for compound 9f in Step E. The crude product was purified by preparative reverse phase chromatography to give 23 mg (50% yield) of Cpd 87. $^1$H NMR (CD$_3$OD) δ=8.08 (s, 1H), 7.93 (br. s., 1H), 7.76-7.84 (m, 2H), 7.68 (dd, J=8.7, 4.5 Hz, 2H), 7.50 (t, J=8.6 Hz, 2H), 7.43 (d, J=8.8 Hz, 1H), 5.31 (br. s., 1H), 4.64 (t, J=13.0 Hz, 1H), 4.45 (t, J=8.4 Hz, 1H), 4.29 (t, J=9.7 Hz, 1H), 4.15-4.24 (m, 1H), 4.00 (br. s., 1H), 3.17-3.27 (m, 1H), 2.83-2.99 (m, 1H), 2.71 (s, 3H), 2.55 (q, J=7.7 Hz, 1H), 1.74-2.00 (m, 3H), 1.15-1.31 (m, 2H). MS m/z 504.0 (M+H$^+$).

-continued

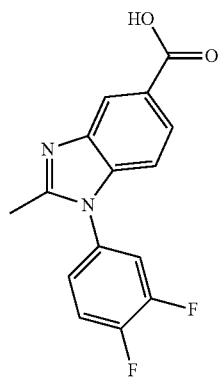
10-I5

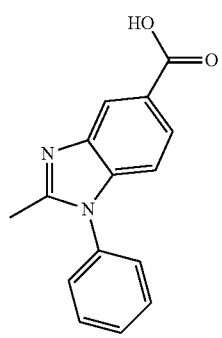
10-I6

Following the procedure described above for Example 10 and substituting the appropriate reagents, starting materials and purification methods known to those skilled in the art, the following compounds of the present invention were prepared:

| Cpd | Name and data |
|---|---|
| 86 | 2-Methyl-1-phenyl-5-({3-[1-(1,3-thiazol-2-ylcarbonyl)piperidin-4-yl]azetidin-1-yl}carbonyl)-1H-benzimidazole. MS m/z 486.1 (M + H⁺). |
| 88 | 1-(3,4-Difluorophenyl)-2-methyl-5-({3-[1-(1,3-thiazol-2-ylcarbonyl)piperidin-4-yl]azetidin-1-yl}carbonyl)-1H-benzimidazole. MS m/z 522.0 (M + H⁺). |
| 89 | 2-Methyl-5-({3-[1-(1,3-thiazol-2-ylcarbonyl)piperidin-4-yl]azetidin-1-yl}carbonyl)-1-[4-(trifluoromethyl)phenyl]-1H-benzimidazole. MS m/z 554.1 (M + H⁺). |
| 90 | 2-Methyl-5-({3-[1-(1,3-thiazol-2-ylcarbonyl)piperidin-4-yl]azetidin-1-yl}carbonyl)-1-(2,2,2-trifluoroethyl)-1H-benzimidazole. MS m/z 492.1 (M + H⁺). |
| 91 | 2-Methyl-5-({3-[1-(1,3-thiazol-2-ylcarbonyl)piperidin-4-yl]azetidin-1-yl}carbonyl)-1-(3,3,3-trifluoropropyl)-1H-benzimidazole. MS m/z 506.2 (M + H⁺). |
| 92 | 1-(4,4-Difluorocyclohexyl)-2-methyl-5-({3-[1-(1,3-thiazol-2-ylcarbonyl)piperidin-4-yl]azetidin-1-yl}carbonyl)-1H-benzimidazole. MS m/z 528.3 (M + H⁺). |

Example 11

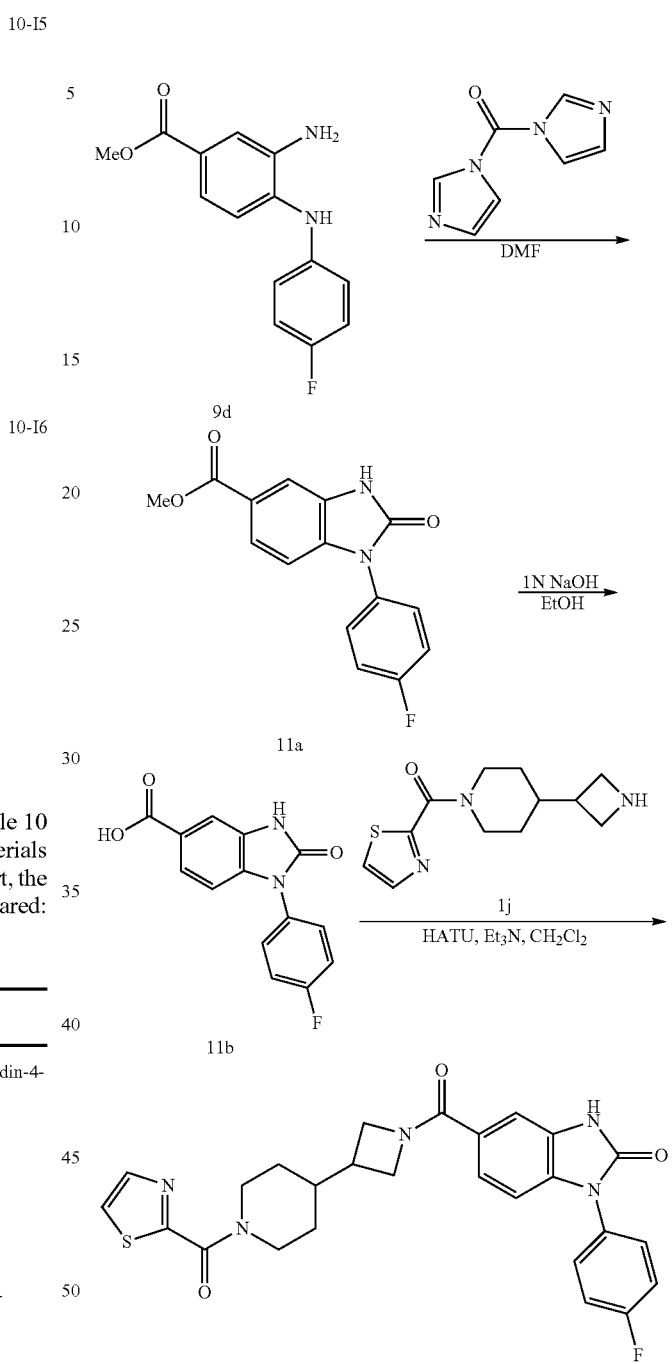

A. Methyl 1-(4-fluorophenyl)-2-oxo-2,3-dihydro-1H-benzo[d]imidazole-5-carboxylate, 11a. A mixture of compound 9d (0.20 g, 0.826 mmol) and 1,1'-carbonyldiimidazole (0.535 g, 3.3 mmol) in DMF (8 mL) was heated at 90° C. for 2 h. The solvent was removed and the residue was triturated with water (15 mL). The resulting precipitate was collected by filtration and washed several times with water. The crude product 11a was used in the next reaction without further purification. MS m/z 287.1 (M+H⁺).

B. 1-(4-Fluorophenyl)-2-oxo-2,3-dihydro-1H-benzo[d]imidazole-5-carboxylate, 11b. The title compound 11b was prepared using the method described in Example 9, substituting compound 11a for compound 9e in Step D. The crude product 11b was used in the next reaction without further purification. MS m/z 273.1 (M+H+).

C. 1-(4-Fluorophenyl)-5-({3-[1-(1,3-thiazol-2-ylcarbonyl)piperidin-4-yl]azetidin-1-yl}carbonyl)-1,3-dihydro-2H-benzimidazol-2-one, Cpd 97. The title compound Cpd 97 was prepared using the method described in Example 9, substituting compound 11b for compound 9f in Step E. The crude product was purified by preparative reverse phase chromatography to give 51 mg (32% yield) of Cpd 97. $^1$H NMR (CD$_3$OD) δ=7.93 (br. s., 1H), 7.81 (d, J=3.2 Hz, 1H), 7.51-7.59 (m, 2H), 7.45 (s, 1H), 7.41 (dd, J=8.3, 1.2 Hz, 1H), 7.33 (t, J=8.7 Hz, 2H), 7.04 (d, J=8.1 Hz, 1H), 5.30 (br. s., 1H), 4.56-4.69 (m, 1H), 4.40-4.51 (m, 1H), 4.21-4.29 (m, 1H), 4.18 (br. s., 1H), 3.95 (br. s., 1H), 3.15-3.27 (m, 1H), 2.83-2.99 (m, 1H), 2.43-2.58 (m, 1H), 1.71-2.00 (m, 3H), 1.22 (br. s., 2H). MS m/z 506.1 (M+H+).

Following the procedure described above for Example 11 and substituting the appropriate reagents, starting materials and purification methods known to those skilled in the art, the following intermediate compounds were prepared.

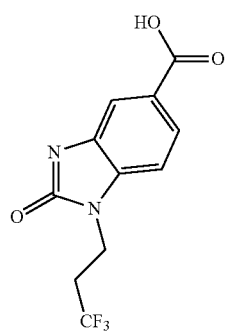

11-I1

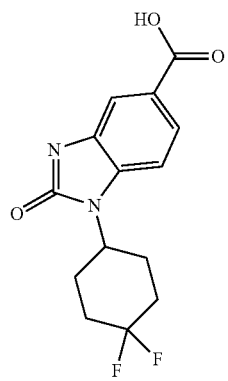

11-I2

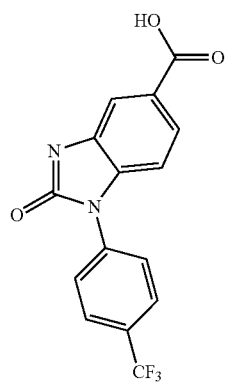

11-I3

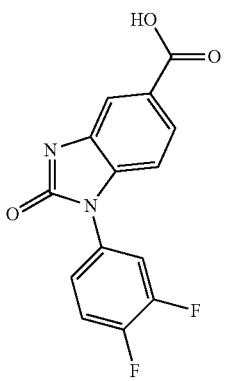

11-I4

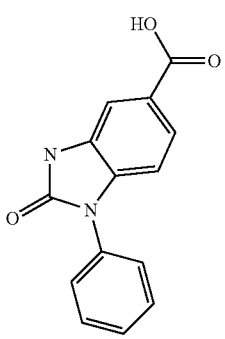

11-I5

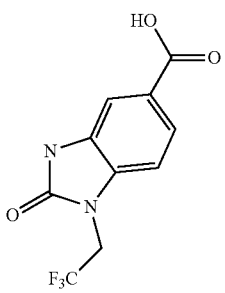

11-I6

Following the procedure described above for Example 11 and substituting the appropriate reagents, starting materials and purification methods known to those skilled in the art, the following compounds of the present invention were prepared.

| Cpd | Name and data |
|---|---|
| 96 | 1-Phenyl-5-({3-[1-(1,3-thiazol-2-ylcarbonyl)piperidin-4-yl]azetidin-1-yl}carbonyl)-1,3-dihydro-2H-benzimidazol-2-one. MS m/z 488.1 (M + H+). |
| 98 | 1-(3,4-Difluorophenyl)-5-({3-[1-(1,3-thiazol-2-ylcarbonyl)piperidin-4-yl]azetidin-1-yl}carbonyl)-1,3-dihydro-2H-benzimidazol-2-one. MS m/z 524.1 (M + H+). |
| 99 | 5-({3-[1-(1,3-Thiazol-2-ylcarbonyl)piperidin-4-yl]azetidin-1-yl}carbonyl)-1-[4-(trifluoromethyl)phenyl]-1,3-dihydro-2H-benzimidazol-2-one. $^1$H NMR (CD$_3$OD) δ = 7.84-7.97 (m, 3H), 7.74-7.83 (m, 3H), 7.38-7.48 (m, 2H), 7.19 (d, J = 8.3 Hz, 1H), 5.22-5.36 (m, 1H), 4.56-4.69 (m, 1H), 4.39-4.53 (m, 1H), 4.11-4.30 (m, 2H), 3.90-4.01 (m, 1H), 2.83-3.00 (m, 1H), 2.43-2.59 (m, 1H), 1.68-2.01 (m, 3H), 1.13-1.29 (m, 2H). |
| 100 | 5-({3-[1-(1,3-Thiazol-2-ylcarbonyl)piperidin-4-yl]azetidin-1-yl}carbonyl)-1-(3,3,3-trifluoropropyl)-1,3-dihydro-2H-benzimidazol-2-one. MS m/z 508.2 (M + H+). |

| Cpd | Name and data |
|---|---|
| 101 | 1-(4,4-Difluorocyclohexyl)-5-({3-[1-(1,3-thiazol-2-ylcarbonyl)piperidin-4-yl]azetidin-1-yl}carbonyl)-1,3-dihydro-2H-benzimidazol-2-one. MS m/z 530.2 (M + H⁺). |

Example 12

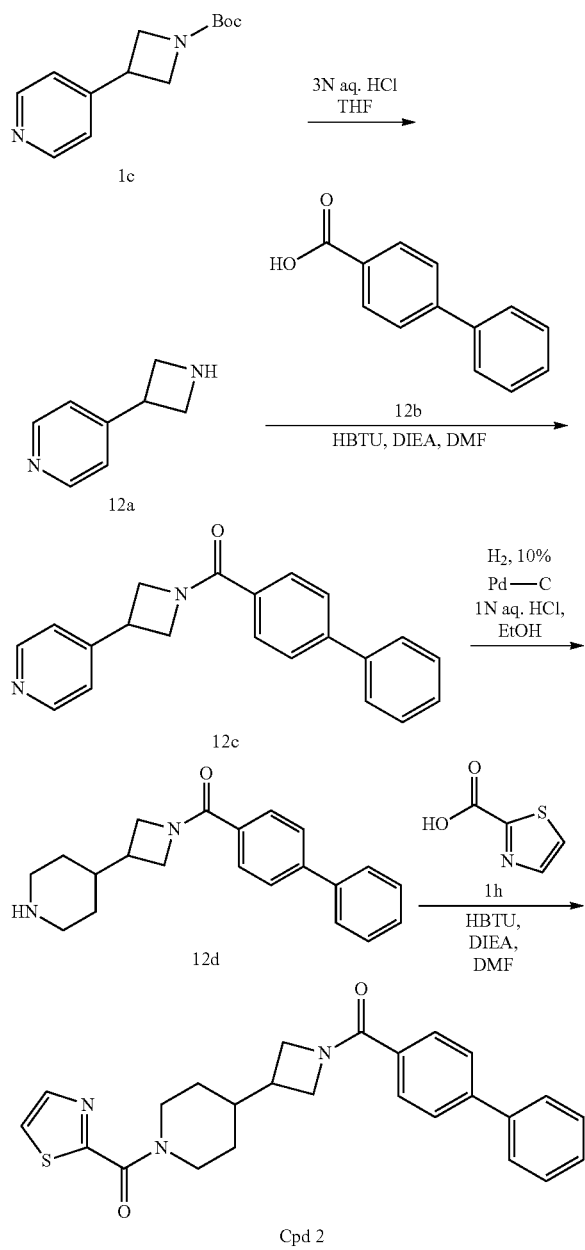

A. 3-(Pyridin-4-yl)azetidine, 12a. Compound 1c was dissolved in a mixture of 3N aqueous HCl and THF and stirred until compound 1c was completely consumed. The mixture was concentrated under reduced pressure and the aqueous residue was lyophilized to give compound 12a as the dihydrochloride salt, which was used in the next step without further purification.

B. [1,1'-Biphenyl]-4-yl-(3-(pyridin-4-yl)azetidin-1-yl) methanone, 12c. Compound 12a (4.5 mmol, 928 mg), [1,1'-biphenyl]-4-carboxylic acid 12b (4.95 mmol, 980 mg), HBTU (6.43 mmol, 2.44 g), and DIEA (20.2 mmol, 3.49 mL) were combined in DMF and stirred at 20° C. for 20 h. The crude reaction mixture was purified by preparative reverse-phase HPLC to give compound 12c. $^1$H NMR (CD$_3$OD, 400 MHz): δ=8.68 (d, J=6.6 Hz, 2H), 7.92 (d, J=6.8 Hz, 2H), 7.68-7.77 (m, 2H), 7.60-7.68 (m, 2H), 7.57 (dd, J=8.3, 1.2 Hz, 2H), 7.38 (t, J=7.5 Hz, 2H), 7.23-7.34 (m, 1H), 4.56-4.68 (m, 1H), 4.43-4.56 (m, 1H), 4.12-4.34 (m, 2H).

C. [1,1'-Biphenyl]-4-yl-(3-(piperidin-4-yl)azetidin-1-yl) methanone, 12d. Compound 12c and 10% palladium on carbon were combined in a 1:5 mixture of 1N aqueous HCl and ethanol in a Parr pressure bottle. The mixture was purged with N$_2$ and then shaken under a 55 psi H$_2$ atmosphere at 20° C. When the reaction was complete, the catalyst was removed by filtration through a diatomaceous earth pad. The filtrate was concentrated and lyophilized to provide compound 12d in quantitative yield as the hydrochloride salt.

D. 4-[1-(Biphenyl-4-ylcarbonyl)azetidin-3-yl]-1-(1,3-thiazol-2-ylcarbonyl)piperidine, Cpd 2. A solution of compound 12d HCl salt (0.28 mmol, 98 mg), thiazole-2-carboxylic acid 1h (0.33 mmol, 43 mg), and HBTU (0.33 mmol, 126 mg) in 2.5 mL of DMF was stirred for 10 min. DIEA (1.1 mmol, 0.2 mL) was added and the mixture was stirred at 20° C. for 20 h. The crude reaction mixture was purified by preparative reverse-phase HPLC to give Cpd 2. $^1$H NMR (CD$_3$OD, 400 MHz): δ=7.84 (br. s., 1H), 7.69-7.75 (m, 1H), 7.60-7.69 (m, 4H), 7.53-7.60 (m, 2H), 7.37 (t, J=7.5 Hz, 2H), 7.24-7.33 (m, 1H), 5.13-5.29 (m, 1H), 4.54 (t, J=11.6 Hz, 1H), 4.38 (t, J=8.7 Hz, 1H), 4.04-4.22 (m, 2H), 3.80-3.94 (m, 1H), 3.07-3.18 (m, 1H), 2.73-2.91 (m, 1H), 2.35-2.50 (m, 1H), 1.63-1.91 (m, 3H), 0.99-1.25 (m, 2H). MS m/z 432.0 (M+H⁺).

Following the procedure described above for Example 12 and substituting the appropriate reagents, starting materials and purification methods known to those skilled in the art, the following compounds of the present invention were prepared:

| Cpd | Name and data |
|---|---|
| 1 | 4-[1-(Biphenyl-4-ylcarbonyl)azetidin-3-yl]-1-(1,3-thiazol-4-ylcarbonyl)piperidine. MS m/z 432.0 (M + H⁺). |
| 3 | 4-[1-(Biphenyl-4-ylcarbonyl)azetidin-3-yl]-1-(isothiazol-5-ylcarbonyl)piperidine. MS m/z 432.0 (M + H⁺). |
| 4 | 4-[1-(Biphenyl-4-ylcarbonyl)azetidin-3-yl]-1-(1H-pyrrol-3-ylcarbonyl)piperidine. MS m/z 414 (M + H⁺). |
| 5 | 4-[1-(Biphenyl-4-ylcarbonyl)azetidin-3-yl]-1-(1,3-thiazol-5-ylcarbonyl)piperidine. MS m/z 432.0 (M + H⁺). |

Example 13

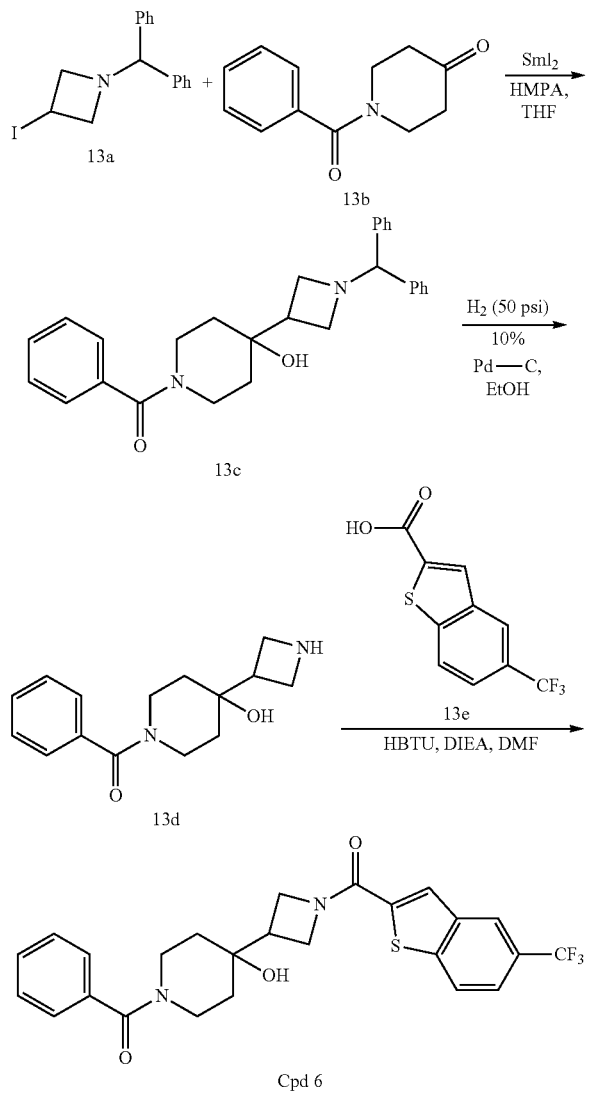

A. (4-(1-Benzhydrylazetidin-3-yl)-4-hydroxypiperidin-1-yl)(phenyl)methanone, 13c. A solution of 1-benzhydryl-3-iodoazetidine 13a (1.4 mmol, 490 mg) in 5 mL of THF was added to a stirring mixture of $SmI_2$ (0.1 M THF solution, 3 mmol, 30 mL) and 1.7 mL of HMPA. After 5 min, a solution of 1-benzoylpiperidin-4-one 13b (3.1 mmol, 626 mg) in 5 mL of THF was added. The reaction mixture was stirred for 2 h. Saturated aqueous $NH_4Cl$ solution (20 mL) was added and the suspension was filtered through a diatomaceous earth pad. The solids were washed with chloroform and the combined organic layers were washed with brine, dried, and concentrated. The crude residue was purified by preparative reverse-phase chromatography to give 400 mg (55% yield) of compound 13c (mono-TFA salt) as a yellow oil. MS m/z 401.2 ($M+H^+$).

B. (4-(Azetidin-3-yl)-4-hydroxypiperidin-1-yl)(phenyl)methanone, 13d. Compound 13c mono-TFA salt (0.34 mmol, 180 mg) and 10% palladium on carbon (40 mg) were combined in a 30 mL of ethanol in a Parr pressure bottle. The mixture was purged with $N_2$ and then shaken under a 50 psi $H_2$ atmosphere at 20° C. for 20 h. The catalyst was removed by filtration through a diatomaceous earth pad and the filtrate was concentrated. Water, $CH_2Cl_2$, and aqueous HCl were added and the mixture was frozen and lyophilized to give 82 mg (81% yield) of compound 13d (mono-HCl salt). MS m/z 261.1 ($M+H^+$).

C. 1-(Phenylcarbonyl)-4-(1-{[5-(trifluoromethyl)-1-benzothiophen-2-yl]carbonyl}azetidin-3-yl)piperidin-4-ol, Cpd 6. A solution of 5-(trifluoromethyl)benzo[b]thiophene-2-carboxylic acid 13e (0.30 mmol, 75 mg), DIEA (0.83 mmol, 0.15 mL), and HBTU (0.33 mmol, 126 mg) in 2 mL of DMF was stirred for 10 min. The HCl salt of compound 13d (0.28 mmol, 82 mg) was added and the mixture was stirred at 20° C. for 20 h. The reaction mixture was filtered through 3 g of silica gel carbonate and 3 g of aminopropyl silica gel using $CH_3CN$ as eluant. The $CH_3CN$ was removed under reduced pressure and the residue was purified by preparative reverse-phase HPLC to give 45 mg (33% yield) of Cpd 6. $^1$H NMR ($CD_3OD$, 400 MHz): δ=8.13-8.24 (m, 1H), 8.04 (d, J=8.6 Hz, 1H), 7.82-7.90 (m, 1H), 7.60 (d, J=8.6 Hz, 1H), 7.27-7.42 (m, 5H), 4.44-4.59 (m, 2H), 4.25-4.39 (m, J=15.0, 2.8 Hz, 1H), 3.98-4.19 (m, 2H), 3.42-3.54 (m, 1H), 3.32-3.42 (m, 1H), 2.79 (quin, J=7.4 Hz, 1H), 1.57-1.69 (m, 1H), 1.31-1.56 (m, 3H). MS m/z 489.1 ($M+H^+$).

Example 14

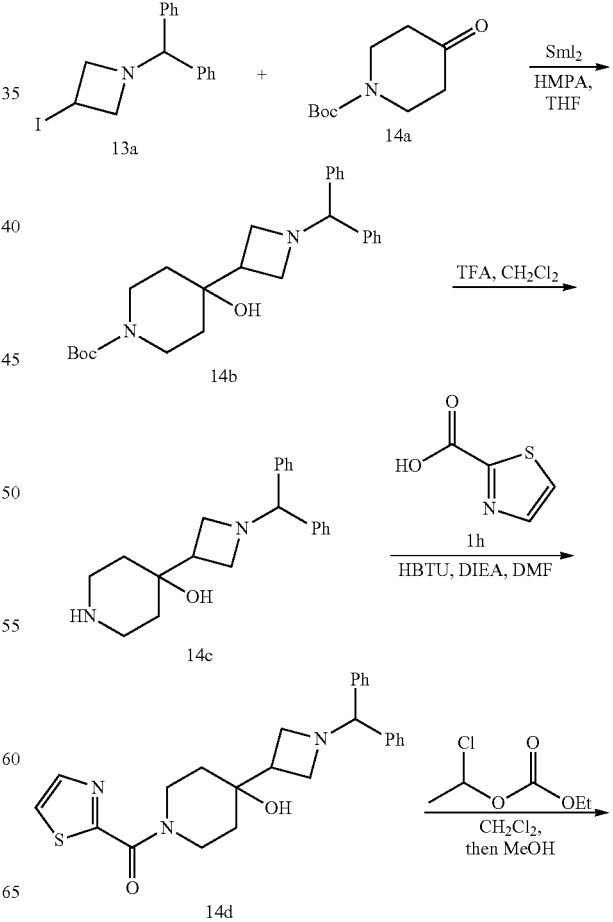

-continued

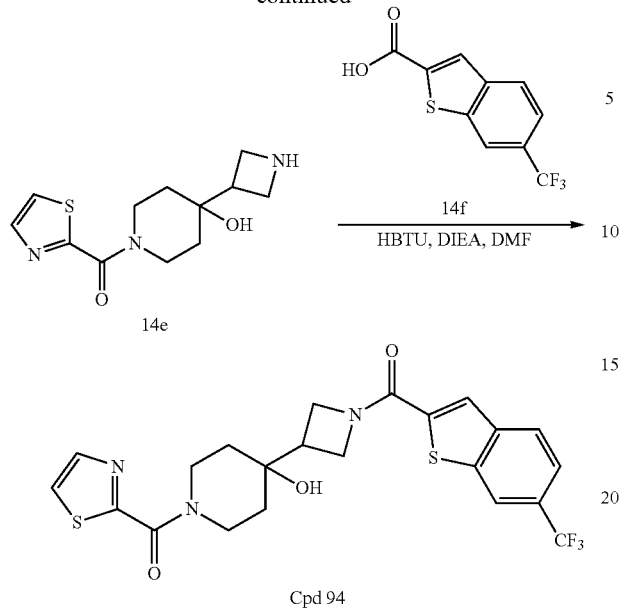

A. (tert-Butyl 4-(1-benzhydrylazetidin-3-yl)-4-hydroxypiperidine-1-carboxylate, 14b. A solution of 1-benzhydryl-3-iodoazetidine 13a (4.75 mmol, 1.66 g) in 10 mL of THF was added to a stirring mixture of SmI$_2$ (0.1 M THF solution, 9.98 mmol, 99.8 mL) and 5.6 mL of HMPA. After 15 min, a solution of tert-butyl 4-oxopiperidine-1-carboxylate 14a (4.75 mmol, 0.95 g) in 15 mL of THF was added. The reaction mixture was stirred for 18 h. Saturated aqueous NH$_4$Cl solution (40 mL) was added and the suspension was filtered through a diatomaceous earth pad. The solids were washed with chloroform and the combined organic layers were washed with brine, dried, and concentrated. The crude residue was purified by preparative reverse-phase chromatography to give 1.0 g (45% yield) of 90% pure compound 14b as a clear oil. MS m/z 423.3 (M+H$^+$).

B. 4-(1-Benzhydrylazetidin-3-yl)piperidin-4-ol, 14c. Compound 14c was prepared according to the procedure described in Example 1, Step F, substituting compound 14b for compound 1i.

C. (4-(1-Benzhydrylazetidin-3-yl)-4-hydroxypiperidin-1-yl)(thiazol-2-yl)methanone, 14d. A solution of thiazole-2-carboxylic acid 1 h (1.79 mmol, 232 mg), DIEA (6.53 mmol, 1.12 mL), and HBTU (1.96 mmol, 742 mg) in 11 mL of DMF was stirred for 10 min. Compound 14c (1.63 mmol, 526 mg) was added and the mixture was stirred at 20° C. for 20 h. The reaction mixture was purified by preparative reverse-phase HPLC to give 298 mg (33% yield) of compound 14d as a buff powder. MS m/z 434.2 (M+H$^+$).

D. 4 (4-(Azetidin-3-yl)-4-hydroxypiperidin-1-yl)(thiazol-2-yl)methanone, 14e. 1-Chloroethyl chloroformate (7.06 mmol, 0.76 mL) was added dropwise to a solution of compound 14d in 20 mL of CH$_2$Cl$_2$ in an ice-water bath. After 30 min, the cooling bath was removed and the reaction mixture was stirred for 2 h at 20° C. The CH$_2$Cl$_2$ was evaporated, 20 mL of MeOH was added, and the resulting solution was refluxed for 2 h. The solvent was evaporated and the residue was partitioned between CH$_2$Cl$_2$ and 0.2 N aqueous HCl. The aqueous layer was lyophilized to give compound 14e, which was carried on to the next step without purification. MS m/z 267.7 (M+H$^+$).

E. 1-(1,3-Thiazol-2-ylcarbonyl)-4-(1-{[6-(trifluoromethyl)-1-benzothiophen-2-yl]carbonyl}azetidin-3-yl)piperidin-4-ol, Cpd 94. A solution of 6-(trifluoromethyl)benzo[b]thiophene-2-carboxylic acid 14f (0.30 mmol, 75 mg), DIEA (0.98 mmol, 0.17 mL), and HBTU (0.30 mmol, 112 mg) in 2 mL of DMF was stirred for 10 min. Compound 14e (0.25 mmol, 66 mg) was added and the mixture was stirred at 20° C. for 20 h. The reaction mixture was purified by preparative reverse-phase HPLC to give 77 mg (62% yield) of Cpd 94 as a white powder. $^1$H NMR (DMSO-d$_6$): δ=8.39 (s, 1H), 8.29 (d, J=8.6 Hz, 1H), 8.02-8.08 (m, 1H), 8.00 (s, 2H), 7.76 (dd, J=8.6, 1.5 Hz, 1H), 4.99 (d, J=12.7 Hz, 1H), 4.46-4.56 (m, 2H), 4.25 (d, J=12.2 Hz, 1H), 4.06-4.15 (m, 1H), 3.97-4.06 (m, 1H), 3.17-3.27 (m, 2H), 2.74-2.86 (m, J=14.8, 7.3, 7.3 Hz, 1H), 1.36-1.66 (m, 4H). MS m/z 496.1 (M+H$^+$).

BIOLOGICAL EXAMPLES

In Vitro Methods

Example 1

MGL Enzyme Activity Assay

All rate-based assays were performed in black 384-well polypropylene PCR microplates (Abgene) in a total volume of 30 μL. Substrate 4-methylumbelliferyl butyrate (4MU-B; Sigma) and either purified mutant MGL (mut-MGLL 11-313 L179S L186S) or purified wild type MGL (wt-MGLL 6H-11-313) were diluted separately into 20 mM PIPES buffer (pH=7.0), containing 150 mM NaCl and 0.001% Tween 20. Compounds of Formula (I) were pre-dispensed (50 nL) into the assay plate using a Cartesian Hummingbird prior to adding 4MU-B (25 μL of 1.2× solution to a final concentration of 10 μM) followed by enzyme (5 μL of a 6× solution to a final concentration of 5 nM) to initiate the reaction. Final compound concentrations ranged from 17 to 0.0003 μM. The fluorescence change due to 4MU-B cleavage was monitored with excitation and emission wavelengths of 335 and 440 nm, respectively, and a bandwidth of 10 nm (Safire$^2$, Tecan) at 37° C. for 5 min.

The IC$_{50}$ values for compounds of Formula (I) were determined using Excel from a fit of the equation to the concentration-response plot of the fractional activity as a function of inhibitor concentration.

TABLE 1

Biological Data

| Cpd | MGL mutant inh IC$_{50}$ (μM) | MGL wild type inh IC$_{50}$ (μM) |
|---|---|---|
| 1 | 0.079 | 0.258 |
| 2 | <0.005 | <0.005 |
| 3 |  | 0.0339 |
| 4 |  | 0.154 |
| 5 |  | 0.0876 |
| 6 |  | 0.918 |
| 7 |  | 0.0565 |
| 8 |  | 0.007 |
| 9 |  | 0.114 |
| 10 |  | 0.0155 |
| 11 |  | 0.498 |
| 12 |  | 0.01 |
| 13 |  | <0.005 |
| 14 |  | 0.005 |
| 15 |  | 0.007 |
| 16 |  | 0.007 |
| 17 |  | 0.0173 |

TABLE 1-continued

Biological Data

| Cpd | MGL mutant inh $IC_{50}$ (μM) | MGL wild type inh $IC_{50}$ (μM) |
|---|---|---|
| 18 | | 0.0125 |
| 19 | | <0.005 |
| 20 | | <0.005 |
| 21 | | 0.0124 |
| 22 | | 0.008 |
| 23 | | 0.368 |
| 24 | | 0.0379 |
| 25 | | 0.0120 |
| 26 | | <0.005 |
| 27 | | 0.00900 |
| 28 | | 0.0164 |
| 29 | | 0.00600 |
| 30 | | <0.005 |
| 31 | | <0.005 |
| 32 | | <0.005 |
| 33 | | <0.005 |
| 34 | | 0.0544 |
| 35 | | <0.005 |
| 36 | | <0.005 |
| 37 | | <0.005 |
| 38 | | 0.005 |
| 39 | | <0.005 |
| 40 | | 0.00900 |
| 41 | | <0.005 |
| 42 | | <0.005 |
| 43 | | <0.005 |
| 44 | | <0.005 |
| 45 | | <0.005 |
| 46 | | 0.111 |
| 47 | | 0.0379 |
| 48 | | <0.005 |
| 49 | | 0.00600 |
| 50 | | <0.005 |
| 51 | | <0.005 |
| 52 | | 0.0715 |
| 53 | | 0.0466 |
| 54 | | <0.005 |
| 55 | | 0.0130 |
| 56 | | <0.005 |
| 57 | | 0.0170 |
| 58 | | <0.005 |
| 59 | | 0.011 |
| 60 | | 0.01 |
| 61 | | 0.211 |
| 62 | | <0.005 |
| 63 | | <0.005 |
| 64 | | <0.005 |
| 65 | | <0.005 |
| 66 | | 0.0192 |
| 67 | | 0.0665 |
| 68 | | 0.0621 |
| 69 | | <0.005 |
| 70 | | 0.008 |
| 71 | | 0.0120 |
| 72 | | 0.0170 |
| 73 | | 0.0120 |
| 74 | | 0.0138 |
| 75 | | <0.005 |
| 76 | | 0.0114 |
| 77 | | <0.005 |
| 78 | | <0.005 |
| 79 | | 0.00900 |
| 80 | | <0.005 |
| 81 | | 0.0232 |
| 82 | | 0.0355 |
| 83 | | 0.00916 |
| 84 | | 0.175 |
| 85 | | 0.280 |
| 86 | | 0.0187 |
| 87 | | 0.0316 |
| 88 | | 0.00949 |
| 89 | | 0.0341 |
| 90 | | 0.173 |
| 91 | | 0.237 |
| 92 | | 0.163 |
| 93 | | <0.005 |
| 94 | | 0.01 |
| 95 | | 0.0140 |
| 96 | | 0.0781 |
| 97 | | 0.0340 |
| 98 | | 0.0166 |
| 99 | | 0.0173 |
| 100 | | 0.101 |
| 101 | | 0.104 |

Example 2

2-AG Accumulation Assay

To measure the accumulation of 2-AG due to inhibition of MGL, one g rat brain was homogenized using a Polytron homogenizer (Brinkmann, PT300) in 10 mL of 20 mM HEPES buffer (pH=7.4), containing 125 mM NaCl, 1 mM EDTA, 5 mM KCl and 20 mM glucose. Compounds of Formula (I) (10 μM) were pre-incubated with rat brain homogenate (50 mg). After a 15-min incubation time at 37° C., $CaCl_2$ (final concentration=10 mM) was added and then incubated for 15 min at 37° C. in a total volume of 5 mL. The reactions were stopped with 6 mL organic solvent extraction solution of 2:1 chloroform/methanol. Accumulated 2-AG in the organic phase was measured by a HPLC/MS method, according to the following equation:

percent vehicle=(2-AG accumulation in the presence of compound/2-AG accumulation in vehicle)×100.

TABLE 2

Biological Data

| Cpd | Rat Brain 2AG % VehCntrl (%) @1 μM |
|---|---|
| 1 | 109 |
| 2 | 329 |
| 3 | 135 |
| 7 | 185 |
| 8 | 523 |
| 10 | 194 |
| 12 | 134 |
| 13 | 335 |
| 14 | 231 |
| 15 | 281 |
| 16 | 493 |
| 17 | 184 |
| 18 | 457 |
| 19 | 559 |
| 20 | 728 |
| 21 | 287 |
| 22 | 470 |
| 24 | 298 |
| 25 | 540 |
| 26 | 303 |
| 27 | 634 |
| 28 | 777 |
| 29 | 800 |
| 30 | 443 |
| 31 | 779 |
| 32 | 1026 |
| 33 | 696 |
| 34 | 517 |

TABLE 2-continued

Biological Data

| Cpd | Rat Brain 2AG % VehCntrl (%) @1 μM |
|---|---|
| 35 | 724 |
| 36 | 507 |
| 37 | 163 |
| 38 | 425 |
| 39 | 371 |
| 40 | 361 |
| 41 | 272 |
| 42 | 498 |
| 43 | 611 |
| 44 | 107 |
| 45 | 385 |
| 47 | 153 |
| 48 | 1022 |
| 49 | 908 |
| 50 | 561 |
| 51 | 266 |
| 52 | 193 |
| 53 | 225 |
| 54 | 736 |
| 55 | 733 |
| 56 | 285 |
| 57 | 869 |
| 58 | 370 |
| 59 | 346 |
| 60 | 508 |
| 62 | 422 |
| 63 | 435 |
| 64 | 383 |
| 65 | 241 |
| 66 | 889 |
| 67 | 590 |
| 68 | 453 |
| 69 | 539 |
| 70 | 561 |
| 71 | 552 |
| 72 | 657 |
| 73 | 875 |
| 74 | 788 |
| 75 | 1135 |
| 76 | 731 |
| 77 | 714 |
| 78 | 1046 |
| 79 | 946 |
| 80 | 860 |

Example 3

MGL ThermoFluor® Assay—Mutant

The ThermoFluor (TF) assay is a 384-well plate-based binding assay that measures thermal stability of proteins[1,2]. The experiments were carried out using instruments available from Johnson & Johnson Pharmaceutical Research & Development, LLC. TF dye used in all experiments was 1,8-ANS (Invitrogen: A-47). Final TF assay conditions used for MGL studies were 0.07 mg/ml of mutant MGL, 100 μM ANS, 200 mM NaCl, 0.001% Tween-20 in 50 mM PIPES (pH=7.0).

Screening compound plates contained 100% DMSO compound solutions at a single concentration. For follow-up concentration-response studies, compounds were arranged in a pre-dispensed plate (Greiner Bio-one: 781280), wherein compounds were serially diluted in 100% DMSO across 11 columns within a series. Columns 12 and 24 were used as DMSO reference and contained no compound. For both single and multiple compound concentration-repsonse experiments, the compound aliquots (46 nL) were robotically predispensed directly into 384-well black assay plates (Abgene: TF-0384/k) using the Hummingbird liquid handler. Following compound dispension, protein and dye solutions were added to achieve the final assay volume of 3 μL. The assay solutions were overlayed with 1 μl of silicone oil (Fluka, type DC 200: 85411) to prevent evaporation.

Bar-coded assay plates were robotically loaded onto a thermostatically controlled PCR-type thermal block and then heated from 40 to 90° C. degrees at a ramp-rate of 1° C./min for all experiments. Fluorescence was measured by continuous illumination with UV light (Hamamatsu LC6), supplied via fiber optics and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. A single image with 20-sec exposure time was collected at each temperature, and the sum of the pixel intensity in a given area of the assay plate was recorded vs temperature and fit to standard equations to yield the $T_m$[1].

1. Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) *J Biomol Screen* 6, 429-40.
2. Matulis, D., Kranz, J. K., Salemme, F. R., and Todd, M. J. (2005) *Biochemistry* 44, 5258-66.

The $K_d$ values for compounds of Formula (I) were determined from a fit of the equation to the concentration-response plot of the fractional activity as a function of $T_m$. For some experiments, quantitative NMR spectroscopy (qNMR) was used to measure concentration of the initial 100% DMSO compound solutions and, using the same fitting method, $qK_d$ values were determined

TABLE 3

Biological Data

| Cpd | MGL mutant ThermoFluor Kd (μM) | MGL mutant ThermoFluor qKd (μM) (using qNMR conc.) |
|---|---|---|
| 1 | 0.100 | |
| 2 | 0.0089 | |
| 3 | 0.0557 | |
| 4 | 0.162 | |
| 5 | 0.0641 | |
| 6 | 0.258 | |
| 7 | 0.0250 | |
| 8 | 0.0040 | |
| 9 | 0.100 | |
| 10 | 0.0110 | |
| 11 | 0.732 | |
| 12 | 0.0220 | |
| 13 | 0.0280 | |
| 14 | 0.0050 | |
| 15 | 0.0090 | |
| 16 | 0.0020 | |
| 17 | 0.0990 | |
| 18 | 0.0030 | |
| 19 | 0.0090 | |
| 20 | 0.0010 | 0.0013 |
| 21 | 0.0286 | |
| 22 | 0.0066 | |
| 23 | 0.500 | |
| 24 | 0.0199 | |
| 25 | 0.0275 | |
| 26 | 0.0036 | |
| 27 | 0.0133 | |
| 28 | 0.0111 | |
| 29 | 0.0003 | 0.0012 |
| 30 | 0.0025 | |

TABLE 3-continued

Biological Data

| Cpd | MGL mutant ThermoFluor Kd (μM) | MGL mutant ThermoFluor qKd (μM) (using qNMR conc.) |
|---|---|---|
| 31 | 0.0026 | |
| 32 | 0.0006 | |
| 33 | 0.0626 | |
| 34 | 0.198 | |
| 35 | 0.0025 | 0.0057 |
| 36 | 0.0225 | |
| 37 | 0.0160 | |
| 38 | 0.0155 | |
| 39 | | 0.0489 |
| 40 | | 0.0946 |
| 41 | 0.0041 | 0.0031 |
| 42 | | 0.0245 |
| 43 | | 0.0264 |
| 44 | | 0.0213 |
| 45 | | 0.0122 |
| 46 | | 0.0200 |
| 47 | 0.0767 | 0.0333 |
| 48 | | 0.0010 |
| 49 | | 0.0010 |
| 50 | | 0.0010 |
| 51 | | 0.0180 |
| 52 | 0.0304 | 0.0322 |
| 53 | | 0.0333 |
| 54 | | 0.0018 |
| 55 | | 0.0020 |
| 56 | 0.0055 | 0.0033 |
| 57 | | 0.0059 |
| 58 | | 0.0069 |
| 59 | 0.0202 | 0.0094 |
| 60 | 0.0008 | 0.0005 |
| 61 | 0.0006 | 0.0005 |
| 62 | 0.0013 | 0.0006 |
| 63 | | 0.0174 |
| 64 | | 0.0189 |
| 65 | | 0.0404 |
| 66 | | 0.0067 |
| 67 | | 0.0066 |
| 68 | | 0.0145 |
| 69 | | 0.0012 |
| 70 | | 0.0006 |
| 71 | | 0.0012 |
| 72 | | 0.0027 |
| 73 | | 0.0048 |
| 74 | | 0.0080 |
| 75 | | 0.0039 |
| 76 | | 0.0083 |
| 77 | | 0.0050 |
| 78 | | 0.0023 |
| 79 | | 0.0033 |
| 80 | | 0.0049 |
| 81 | | 0.0148 |
| 82 | | 0.0228 |
| 83 | | 0.0136 |
| 84 | | 0.0663 |
| 85 | | 0.0645 |
| 86 | | 0.0106 |
| 87 | | 0.0075 |
| 88 | | 0.0133 |
| 89 | | 0.0077 |
| 90 | | 0.0237 |
| 91 | | 0.0325 |
| 92 | | 0.0034 |
| 93 | 0.0055 | |
| 94 | | 0.0249 |
| 95 | | 0.0386 |
| 96 | | 0.0247 |
| 97 | | 0.0221 |
| 98 | | 0.0436 |
| 99 | | 0.0167 |
| 100 | | 0.0888 |
| 101 | | 0.0039 |

In Vivo Methods

Example 4

CFA-Induced Paw Radiant Heat Hypersensitivity

Each rat was placed in a test chamber on a warm glass surface and allowed to acclimate for approximately 10 min. A radiant thermal stimulus (beam of light) was focused through the glass onto the plantar surface of each hind paw in turn. The thermal stimulus was automatically shut off by a photoelectric relay when the paw was moved or when the cut-off time was reached (20 sec for radiant heat at ~5 amps). An initial (baseline) response latency to the thermal stimulus was recorded for each animal prior to the injection of complete Freund's adjuvant (CFA). Twenty-four hours following intraplantar CFA injection, the response latency of the animal to the thermal stimulus was re-evaluated and compared to the animal's baseline response time. Only rats that exhibited at least a 25% reduction in response latency (i.e., are hyperalgesic) were included in further analysis. Immediately following the post-CFA latency assessment, the indicated test compound or vehicle was administered orally. Post-compound treatment withdrawal latency was assessed at fixed time intervals, typically 30, 60, 120, 180, and 300 min.

The percent reversal (% R) of hypersensitivity was calculated in one of two different ways: 1) using group mean values or 2) using individual animal values. More specifically:

Method 1. For all compounds, the % R of hypersensitivity was calculated using the mean value for groups of animals at each time point according to the following formula:

% reversal=[(group treatment response−group CFA response)/(group baseline response−group CFA response)]×100

Results are given for the maximum % reversal observed for each compound at any time point tested.

Method 2. For some compounds, the % R of hypersensitivity was calculated separately for each animal according to the following formula:

% reversal=[(individual treatment response−individual CFA response)/(individual baseline response−individual CFA response)]×100.

Results are given as a mean of the maximum % reversal values calculated for each individual animal.

Biological Data Table 4

| Cpd No. | dose (mg/kg, p.o.) | vehicle | no. of animals | last time point (min) | Method 1: peak % reversal | Method 2: peak % reversal |
|---|---|---|---|---|---|---|
| 20 | 30 | 20% HPβCD | 8 | 300 | −6.7 | Not calculated |
| 29 | 30 | 10% NMP/ 20% solutol | 8 | 300 | 17.9 | Not calculated |

Example 5

CFA-Induced Paw Pressure Hypersensitivity

Prior to testing, rats may be acclimated to the handling procedure twice a day for a period of two days. The test consists of placing the left hindpaw on a polytetrafluoroethylene platform and applying a linearly increasing mechanical force (constant rate of 12.5 mmHg/s) in between the third and fourth metatarsal of the dorsum of the rat's hindpaw, with a dome-tipped plinth (0.7 mm in radius), using an analgesymeter (Stoelting, Chicago, Ill.), also known as a Randall-Selitto apparatus. The endpoint may be automatically reached upon hindpaw withdrawal, and the terminal force may be noted (in grams). An initial (baseline) response threshold to the mechanical stimulus may be recorded for each animal prior to the injection of complete Freund's adjuvant (CFA). Forty hours following intraplantar CFA injection, the response threshold of the animal to the mechanical stimulus may be re-evaluated and compared to the animal's baseline response threshold. A response may be defined as a withdrawal of the hindpaw, a struggling to remove the hindpaw, or vocalization. Only rats that exhibit at least a 25% reduction in response threshold (i.e., hyperalgesia) may be included in further analysis. Immediately following the post-CFA threshold assessment, rats may be administered the indicated test compound or vehicle. Post-treatment withdrawal thresholds may be assessed at 1 h. Paw withdrawal thresholds may be converted to percent reversal of hypersensitivity according to the following formula:

% reversal=[(post treatment response−predose response)/(baseline response−predose response)]×100.

Example 6

Chronic Constriction Injury (CCI)-Induced Model of Neuropathic Pain—Cold Acetone-Hypersensitivity Test Male Sprague-Dawley rats (225-450 g) may be used to evaluate the ability of selected compounds to reverse CCI-induced cold hypersensitivity. Four loose ligatures of 4-0 chromic gut may be surgically placed around the left sciatic nerve under inhalation anesthesia as described by Bennett et al. (Bennett G J, Xie Y K. *Pain* 1988, 33(1): 87-107). Fourteen to 35 days following CCI surgery, subjects may be placed in elevated observation chambers containing wire mesh floors, and five applications of acetone (0.05 mL/application separated by approximately 5 minutes) may be spritzed onto the plantar surface of the paw using a multidose syringe. An abrupt withdrawal or lifting of the paw may be considered a positive response. The number of positive responses may be recorded for each rat over the five trials. Following baseline withdrawal determinations, compounds may be administered in the indicated vehicle, by the indicated route (see Table 6). The number of withdrawals may be re-determined 1 to 4 hr after compound administration. Results may be presented as a percent inhibition of shakes, which may be calculated for each subject as [1-(test compound withdrawals/pre-test withdrawals)]×100 and then averaged by treatment.

Example 7

Spinal Nerve Ligation (SNL) Model of Neuropathic Pain—Tactile Allodynia Test

For lumbar 5 ($L_5$) spinal nerve ligation (SNL) studies, anesthesia may be induced and maintained on isoflurane inhalation. Fur may be clipped over the dorsal pelvic area, and a 2-cm skin incision may be made just left of midline over the dorsal aspect of the $L_4$—$S_2$ spinal segments, followed by separation of the paraspinal muscles from spinous processes. The transverse process of $L_6$ may be carefully removed, and the $L_5$ spinal nerve may be identified. The left $L_5$ spinal nerve may be ligated tightly with 6-0 silk thread, the muscle may be sutured with 4-0 vicryl, and the skin may be closed with wound clips. Following surgery, s.c. saline (5 mL) may be administered.

Behavioral testing may be performed four weeks post-ligation. Following baseline von Frey determinations to verify the presence of mechanical allodynia, $L_5$ SNL rats may be orally administered the indicated vehicle or drug. Tactile allodynia may be quantified at 30, 60, 100, 180, and 300 min post-dosing by recording the force at which the paw ipsilateral to the nerve ligation is withdrawn from the application of a series of calibrated von Frey filaments (0.4, 0.6, 1.0, 2.0, 4, 6, 8 and 15 g; Stoelting; Wood Dale, Ill.). Beginning at an intermediate stiffness (2.0 g), filaments may be applied to the mid-plantar hind paw for approximately 5 seconds to determine the response threshold, a brisk paw withdrawal leads to the presentation of the next lighter stimulus, whereas a lack of a withdrawal response leads to the presentation of the next stronger stimulus. A total of four responses after the first threshold detection may be collected. The 50% withdrawal thresholds may be interpolated by the method of Dixon as modified by Chaplan et.al., and when response thresholds fall above or below the range of detection, respective values of 15.0 or 0.25 g may be assigned. Threshold data from von Frey filament testing may be reported as withdrawal threshold in grams. Data may be normalized and results may be presented as % MPE (maximum possible effect) of the drug calculated according to the following formula:

$$\% MPE = \frac{x \text{ g/force} - \text{baseline g/force}}{15 \text{ g/force} - \text{baseline g/force}} \times 100$$

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula (I)

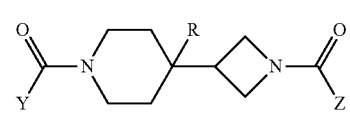

Formula (I)

wherein
  Y and Z are independently selected from Group a) or Group b) such that one of Y and Z is Group a) and the other is Group b);
Group a) is
  i) $C_{6-10}$ aryl is unsubstituted or substituted with a substituent selected from the group consisting of fluoro, chloro, $C_{1-4}$alkyl, $C_{1-4}$alkoxy, cyano, and trifluoromethyl; or
  ii) an unsubstituted heteroaryl selected from the group consisting of thiazolyl, isothiazolyl, and 1H-pyrrolyl;
Group b) is selected from the group consisting of
  i) $C_{6-10}$ aryl;
  ii) a heteroaryl selected from the group consisting of benzoxazolyl, benzothiazolyl, benzimidazolyl, benzothienyl, indazolyl, and indolyl;
  iii) phenylmethyl-phenyl wherein the phenyl group of phenylmethyl is unsubstituted or substituted with trifluoromethyl or fluoro; and iv) 1,3-dihydro-3H-benzimidazol-2-on-yl;
wherein Group b) other than phenylmethyl-phenyl is unsubstituted or substituted with one or two substituents independently selected from the group consisting of bromo, chloro, fluoro, iodo, $C_{1-4}$alkyl, $C_{1-4}$alkoxy, and $R_b$; provided that no more than one substituent is $R_b$; and $R_b$ is selected from the group consisting of trifluoromethyl, 2,2,2-trifluoroethyl, 3,3,3-trifluoropropyl, 4,4-difluorocyclohexyl, thienyl, pyridinyl, and phenyl; wherein said thienyl, pyridinyl, and phenyl of $R_b$ are unsubstituted or substituted with one or two substituents independently selected from the group consisting of trifluoromethyl, methyl, chloro, cyano, and fluoro;
R is hydrogen or hydroxy;
and enantiomers, diastereomers, and pharmaceutically acceptable salts thereof.

2. The compound of claim 1 wherein Group a) is an unsubstituted phenyl or an unsubstituted heteroaryl selected from the group consisting of thiazolyl, isothiazolyl, and 1H-pyrrolyl.

3. The compound of claim 1 wherein Group a) is an unsubstituted phenyl or an unsubstituted heteroaryl selected from the group consisting of thiazol-2-yl, thiazol-4-yl, thiazol-5-yl, isothiazolyl, 1H-pyrrol-2-yl, and 1H-pyrrol-3-yl.

4. The compound of claim 1 wherein Group b) is selected from the group consisting of
i) phenyl;
ii) a heteroaryl selected from the group consisting of benzoxazolyl, benzimidazolyl, benzothienyl, and indolyl;
iii) phenylmethyl-phenyl wherein the phenyl group of phenylmethyl is unsubstituted or substituted with trifluoromethyl or fluoro; and
iv) 1,3-dihydro-3H-benzimidazol-2-on-yl;
wherein Group b) other than phenylmethyl-phenyl is unsubstituted or substituted with one or two substituents independently selected from the group consisting of chloro, fluoro, methyl, and $R_b$; provided that no more than one substituent is $R_b$; and $R_b$ is selected from the group consisting of trifluoromethyl, 2,2,2-trifluoroethyl, 3,3,3-trifluoropropyl, 4,4-difluorocyclohexyl, thienyl, pyridinyl, and phenyl; wherein said thienyl, pyridinyl, and phenyl of $R_b$ are unsubstituted or substituted with one or two substituents independently selected from the group consisting of trifluoromethyl, methyl, chloro, and fluoro.

5. The compound of claim 1 wherein Group b) is delected from the group consisting of
i) phenyl;
ii) a heteroaryl selected from the group consisting of benzoxazolyl, benzimidazolyl, benzothienyl, and indolyl;
iii) phenylmethyl-phenyl wherein the phenyl group of phenylmethyl is unsubstituted or substituted with trifluoromethyl; and
iv) 1,3-dihydro-3H-benzimidazol-2-on-yl;
wherein Group b) other than phenylmethyl-phenyl is unsubstituted or substituted with one or two substituents independently selected from the group consisting of chloro, fluoro, methyl, and $R_b$; provided that no more than one substituent is $R_b$; and $R_b$ is selected from the group consisting of trifluoromethyl, thienyl, pyridinyl, and phenyl; wherein said thienyl, pyridinyl, and phenyl of $R_b$ are unsubstituted or substituted with one or two substituents independently selected from the group consisting of trifluoromethyl, methyl, chloro, and fluoro.

6. The compound of claim 1 wherein R is hydrogen.

7. A compound of Formula (I)

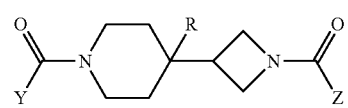

Formula (I)

wherein
Y and Z are independently selected from Group a) or Group b) such that one of Y and Z is Group a) and the other is Group b);
Group a) is an unsubstituted phenyl or an unsubstituted heteroaryl selected from the group consisting of thiazolyl, isothiazolyl, and 1H-pyrrolyl;
Group b) is selected from the group consisting of
i) phenyl;
ii) a heteroaryl selected from the group consisting of benzoxazolyl, benzimidazolyl, benzothienyl, and indolyl;
iii) phenylmethyl-phenyl wherein the phenyl group of phenylmethyl is unsubstituted or substituted with trifluoromethyl or fluoro; and
iv) 1,3-dihydro-3H-benzimidazol-2-on-yl;
wherein Group b) other than phenylmethyl-phenyl is unsubstituted or substituted with one or two substituents independently selected from the group consisting of chloro, fluoro, methyl, and $R_b$; provided that no more than one substituent is $R_b$; and $R_b$ is selected from the group consisting of trifluoromethyl, 2,2,2-trifluoroethyl, 3,3,3-trifluoropropyl, 4,4-difluorocyclohexyl, thienyl, pyridinyl, and phenyl; wherein said thienyl, pyridinyl, and phenyl of $R_b$ are unsubstituted or substituted with one or two substituents independently selected from the group consisting of trifluoromethyl, methyl, chloro, and fluoro;
R is hydrogen;
and enantiomers, diastereomers, and pharmaceutically acceptable salts thereof.

8. A compound of Formula (I)

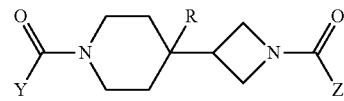

Formula (I)

wherein
Y and Z are independently selected from Group a) or Group b) such that one of Y and Z is Group a) and the other is Group b);
Group a) is an unsubstituted phenyl or unsubstituted heteroaryl selected from the group consisting of thiazolyl, isothiazolyl, and 1H-pyrrolyl;
Group b) is selected from the group consisting of
i) phenyl;
ii) a heteroaryl selected from the group consisting of benzoxazolyl, benzimidazolyl, benzothienyl, and indolyl;
iii) phenylmethyl-phenyl wherein the phenyl group of phenylmethyl is unsubstituted or substituted with trifluoromethyl; and
iv) 1,3-dihydro-3H-benzimidazol-2-on-yl;
wherein Group b) other than phenylmethyl-phenyl is unsubstituted or substituted with one or two substituents independently selected from the group consisting of chloro, fluoro, methyl, and $R_b$; provided that no more than one substituent is $R_b$; and $R_b$ is selected from the group consisting of trifluoromethyl, thienyl, pyridinyl, and phenyl; wherein said thienyl, pyridinyl, and phenyl of $R_b$ are unsubstituted or substituted with one or two substituents independently selected from the group trifluoromethyl, methyl, chloro, and fluoro;

R is hydrogen or hydroxy;

and enantiomers, diastereomers, and pharmaceutically acceptable salts thereof.

9. A compound of Formula (I)

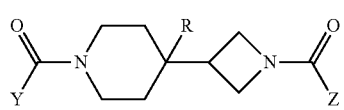

Formula (I)

wherein

Y and Z are independently selected from Group a) or Group b) such that one of Y and Z is Group a) and the other is Group b);

Group a) is an unsubstituted phenyl or an unsubstituted heteroaryl selected from the group consisting of thiazol-2-yl, thiazol-4-yl, thiazol-5-yl, isothiazolyl, 1H-pyrrol-2-yl, and 1H-pyrrol-3-yl;

Group b) is selected from the group consisting of i) phenyl;

ii) a heteroaryl selected from the group consisting of benzoxazolyl, benzimidazolyl, benzothienyl, and indolyl;

iii) phenylmethyl-phenyl wherein the phenyl group of phenylmethyl is unsubstituted or substituted with trifluoromethyl; and iv) 1,3-dihydro-3H-benzimidazol-2-on-yl;

wherein Group b) other than phenylmethyl-phenyl is unsubstituted or substituted with one or two substitutents independently selected from the group consisting of chloro, fluoro, methyl, and $R_b$; provided that no more than one substituent is $R_b$; and $R_b$ is selected from the group consisting of trifluoromethyl, thienyl, pyridinyl, and phenyl; wherein said thienyl, pyridinyl, and phenyl of $R_b$ are unsubstituted or substituted with one or two substituents independently selected from the group consisting of trifluoromethyl, methyl, chloro, and fluoro;

R is hydrogen or hydroxy;

and enantiomers, diastereomers, and pharmaceutically acceptable salts thereof.

10. A compound of Formula (I)

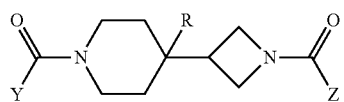

Formula (I)

selected from the group consisting of the compound wherein Y is thiazol-4-yl, Z is biphenyl-4-yl, and R is H;

the compound wherein Y is thiazol-2-yl, Z is biphenyl-4-yl, and R is H;

the compound wherein Y is isothiazol-5-yl, Z is biphenyl-4-yl, and R is H;

the compound wherein Y is 1H-pyrrol-3-yl, Z is biphenyl-4-yl, and R is H;

the compound wherein Y is thiazol-5-yl, Z is biphenyl-4-yl, and R is H;

the compound wherein Y is phenyl, Z is 5-trifluoromethyl-benzothien-2-yl, and R is OH;

the compound wherein Y is thiazol-4-yl, Z is 3-chloro-6-fluoro-benzothien-2-yl, and R is H;

the compound wherein Y is thiazol-2-yl, Z is 3-chloro-6-fluoro-benzothien-2-yl, and R is H;

the compound wherein Y is thiazol-4-yl, Z is 2-fluoro-4-phenyl-phenyl, and R is H;

the compound wherein Y is thiazol-4-yl, Z is 4-(3-trifluoromethylphenyl)-phenyl, and R is H;

the compound wherein Y is thiazol-4-yl, Z is 3-(3-fluorophenyl)-phenyl, and R is H;

the compound wherein Y is thiazol-4-yl, Z is 4-(5-trifluoromethylthien-2-yl)-phenyl, and R is H;

the compound wherein Y is thiazol-4-yl, Z is 4-(3-trifluoromethylphenylmethyl)-phenyl, and R is H;

the compound wherein Y is thiazol-4-yl, Z is 3-methyl-6-trifluoromethyl-benzothien-2-yl, and R is H;

the compound wherein Y is thiazol-2-yl, Z is 2-fluoro-4-phenyl-phenyl, and R is H;

the compound wherein Y is thiazol-2-yl, Z is 4-(3-trifluoromethylphenyl)-phenyl, and R is H;

the compound wherein Y is thiazol-2-yl, Z is 3-(3-fluorophenyl)-phenyl, and R is H;

the compound wherein Y is thiazol-2-yl, Z is 4-(5-trifluoromethylthien-2-yl)-phenyl, and R is H;

the compound wherein Y is thiazol-2-yl, Z is 4-(3-trifluoromethylphenylmethyl)-phenyl, and R is H;

the compound wherein Y is thiazol-2-yl, Z is 3-methyl-6-trifluoromethyl-benzothien-2-yl, and R is H;

the compound wherein Y is 1H-pyrrol-2-yl, Z is 2-fluoro-4-phenyl-phenyl, and R is H;

the compound wherein Y is 1H-pyrrol-2-yl, Z is 4-(3-trifluoromethylphenyl)-phenyl, and R is H;

the compound wherein Y is 1H-pyrrol-2-yl, Z is 3-(3-fluorophenyl)-phenyl, and R is H;

the compound wherein Y is 1H-pyrrol-2-yl, Z is 4-(5-trifluoromethylthien-2-yl)-phenyl, and R is H;

the compound wherein Y is 1H-pyrrol-2-yl, Z is 4-(3-trifluoromethylphenylmethyl)-phenyl, and R is H;

the compound wherein Y is 1H-pyrrol-2-yl, Z is 3-methyl-6-trifluoromethyl-benzothien-2-yl, and R is H;

the compound wherein Y is thiazol-2-yl, Z is 4-(4-trifluoromethylphenylmethyl)-phenyl, and R is H;

the compound wherein Y is thiazol-2-yl, Z is 2-phenyl-benzoxazol-6-yl, and R is H;

the compound wherein Y is thiazol-2-yl, Z is 3-chloro-6-trifluoromethyl-benzothien-2-yl, and R is H;

the compound wherein Y is thiazol-2-yl, Z is 1-(4-fluorophenyl)-1H-indol-5-yl, and R is H;

the compound wherein Y is thiazol-2-yl, Z is 1-(4-trifluoromethylphenyl)-1H-indol-5-yl, and R is H;

the compound wherein Y is thiazol-2-yl, Z is 1-(3,4-difluorophenyl)-1H-indol-5-yl, and R is H;

the compound wherein Y is thiazol-4-yl, Z is 4-(4-trifluoromethylphenylmethyl)-phenyl, and R is H;

the compound wherein Y is thiazol-4-yl, Z is 2-phenyl-benzoxazol-6-yl, and R is H;

the compound wherein Y is thiazol-4-yl, Z is 3-chloro-6-trifluoromethyl-benzothien-2-yl, and R is H;

the compound wherein Y is thiazol-4-yl, Z is 1-(4-fluorophenyl)-1H-indol-5-yl, and R is H;

the compound wherein Y is thiazol-4-yl, Z is 1-(4-trifluoromethylphenyl)-1H-indol-5-yl, and R is H;
the compound wherein Y is thiazol-4-yl, Z is 1-(3,4-difluorophenyl)-1H-indol-5-yl, and R is H;
the compound wherein Y is 1H-pyrrol-2-yl, Z is 4-(4-trifluoromethylphenylmethyl)-phenyl, and R is H;
the compound wherein Y is 1H-pyrrol-2-yl, Z is 2-phenyl-benzoxazol-6-yl, and R is H;
the compound wherein Y is 1H-pyrrol-2-yl, Z is 3-chloro-6-trifluoromethyl-benzothien-2-yl, and R is H;
the compound wherein Y is 1H-pyrrol-2-yl, Z is 1-(4-fluorophenyl)-1H-indol-5-yl, and R is H;
the compound wherein Y is 1H-pyrrol-2-yl, Z is 1-(4-trifluoromethylphenyl)-1H-indol-5-yl, and R is H;
the compound wherein Y is 1H-pyrrol-2-yl, Z is 1-(3,4-difluorophenyl)-1H-indol-5-yl, and R is H;
the compound wherein Y is 2-fluoro-4-phenyl-phenyl, Z is thiazol-2-yl, and R is H;
the compound wherein Y is 2-fluoro-4-phenyl-phenyl, Z is thiazol-4-yl, and R is H;
the compound wherein Y is 1H-pyrrol-2-yl, Z is 2-fluoro-4-phenyl-phenyl, and R is H;
the compound wherein Y is 4-(3-trifluoromethylphenyl)-phenyl, Z is thiazol-2-yl, and R is H;
the compound wherein Y is 4-(3-trifluoromethylphenyl)-phenyl, Z is thiazol-4-yl, and R is H;
the compound wherein Y is 4-(3-trifluoromethylphenyl)-phenyl, Z is 1H-pyrrol-2-yl, and R is H;
the compound wherein Y is 3-(3-fluorophenyl)-phenyl, Z is thiazol-2-yl, and R is H;
the compound wherein Y is 3-(3-fluorophenyl)-phenyl, Z is thiazol-4-yl, and R is H;
the compound wherein Y is 3-(3-fluorophenyl)-phenyl, Z is 1H-pyrrol-2-yl, and R is H;
the compound wherein Y is 4-(5-trifluoromethyl-thien-2-yl)-phenyl, Z is thiazol-2-yl, and R is H;
the compound wherein Y is 4-(5-trifluoromethyl-thien-2-yl)-phenyl, Z is thiazol-4-yl, and R is H;
the compound wherein Y is 4-(5-trifluoromethyl-thien-2-yl)-phenyl, Z is 1H-pyrrol-2-yl, and R is H;
the compound wherein Y is 4-(3-trifluoromethylphenylmethyl)-phenyl, Z is thiazol-2-yl, and R is H;
the compound wherein Y is 4-(3-trifluoromethylphenylmethyl)-phenyl, Z is thiazol-4-yl, and R is H;
the compound wherein Y is 4-(3-trifluoromethylphenylmethyl)-phenyl, Z is 1H-pyrrol-2-yl, and R is H;
the compound wherein Y is 3-methyl-6-trifluoromethyl-benzothien-2-yl, Z is thiazol-2-yl, and R is H;
the compound wherein Y is 3-methyl-6-trifluoromethyl-benzothien-2-yl, Z is thiazol-4-yl, and R is H;
the compound wherein Y is 3-methyl-6-trifluoromethyl-benzothien-2-yl, Z is 1H-pyrrol-2-yl, and R is H;
the compound wherein Y is 4-(4-trifluoromethylphenylmethyl)-phenyl, Z is thiazol-2-yl, and R is H;
the compound wherein Y is 4-(4-trifluoromethylphenylmethyl)-phenyl, Z is thiazol-4-yl, and R is H;
the compound wherein Y is 4-(4-trifluoromethylphenylmethyl)-phenyl, Z is 1H-pyrrol-2-yl, and R is H;
the compound wherein Y is 2-phenyl-benzoxazol-6-yl, Z is thiazol-2-yl, and R is H;
the compound wherein Y is 2-phenyl-benzoxazol-6-yl, Z is thiazol-4-yl, and R is H;
the compound wherein Y is 2-phenyl-benzoxazol-6-yl, Z is 1H-pyrrol-2-yl, and R is H;
the compound wherein Y is 3-chloro-6-trifluoromethyl-benzothien-2-yl, Z is thiazol-2-yl, and R is H;
the compound wherein Y is 3-chloro-6-trifluoromethyl-benzothien-2-yl, Z is thiazol-4-yl, and R is H;
the compound wherein Y is 3-chloro-6-trifluoromethyl-benzothien-2-yl, Z is 1H-pyrrol-2-yl, and R is H;
the compound wherein Y is 1-(4-fluorophenyl)-1H-indol-5-yl, Z is thiazol-2-yl, and R is H;
the compound wherein Y is 1-(4-fluorophenyl)-1H-indol-5-yl, Z is thiazol-4-yl, and R is H;
the compound wherein Y is 1-(4-fluorophenyl)-1H-indol-5-yl, Z is 1H-pyrrol-2-yl, and R is H;
the compound wherein Y is 1-(4-trifluoromethylphenyl)-1H-indol-5-yl, Z is thiazol-2-yl, and R is H;
the compound wherein Y is 1-(4-trifluoromethylphenyl)-1H-indol-5-yl, Z is thiazol-4-yl, and R is H;
the compound wherein Y is 1-(4-trifluoromethylphenyl)-1H-indol-5-yl, Z is 1H-pyrrol-2-yl, and R is H;
the compound wherein Y is 1-(3,4-difluorophenyl)-1H-indol-5-yl, Z is thiazol-2-yl, and R is H;
the compound wherein Y is 1-(3,4-difluorophenyl)-1H-indol-5-yl, Z is thiazol-4-yl, and R is H;
the compound wherein Y is 1-(3,4-difluorophenyl)-1H-indol-5-yl, Z is 1H-pyrrol-2-yl, and R is H;
the compound wherein Y is thiazol-2-yl, Z is 1-(4-fluorophenyl)-1H-benzimidazol-5-yl, and R is H;
the compound wherein Y is thiazol-2-yl, Z is 1-(3,4-difluorophenyl)-1H-benzimidazol-5-yl, and R is H;
the compound wherein Y is thiazol-2-yl, Z is 1-(4-trifluoromethylphenyl)-1H-benzimidazol-5-yl, and R is H;
the compound wherein Y is thiazol-2-yl, Z is 1-(2,2,2-trifluoroethyl)-1H-benzimidazol-5-yl, and R is H;
the compound wherein Y is thiazol-2-yl, Z is 1-(3,3,3-trifluoropropyl)-1H-benzimidazol-5-yl, and R is H;
the compound wherein Y is thiazol-2-yl, Z is 1-phenyl-2-methyl-1H-benzimidazol-5-yl, and R is H;
the compound wherein Y is thiazol-2-yl, Z is 1-(4-fluorophenyl)-2-methyl-1H-benzimidazol-5-yl, and R is H;
the compound wherein Y is thiazol-2-yl, Z is 1-(3,4-difluorophenyl)-2-methyl-1H-benzimidazol-5-yl, and R is H;
the compound wherein Y is thiazol-2-yl, Z is 1-(4-trifluoromethylphenyl)-2-methyl-1H-benzimidazol-5-yl, and R is H;
the compound wherein Y is thiazol-2-yl, Z is 1-(2,2,2-trifluoroethyl)-2-methyl-1H-benzimidazol-5-yl, and R is H;
the compound wherein Y is thiazol-2-yl, Z is 1-(3,3,3-trifluoropropyl)-2-methyl-1H-benzimidazol-5-yl, and R is H;
the compound wherein Y is thiazol-2-yl, Z is 1-(4,4-difluorocyclohexyl)-2-methyl-1H-benzimidazol-5-yl, and R is H;
the compound wherein Y is thiazol-2-yl, Z is 1-(5-chloro-pyridin-2-yl)-1H-indol-5-yl, and R is H;
the compound wherein Y is thiazol-2-yl, Z is 6-trifluoromethyl-benzothien-2-yl, and R is OH;
the compound wherein Y is thiazol-2-yl, Z is 1-(2-methylpyridin-4-yl)-1H-indol-5-yl, and R is H;
the compound wherein Y is thiazol-2-yl, Z is 1-phenyl-1,3-dihydro-3H-benzimidazol-2-on-5-yl, and R is H;
the compound wherein Y is thiazol-2-yl, Z is 1-(4-fluorophenyl)-1,3-dihydro-3H-benzimidazol-2-on-5-yl, and R is H;
the compound wherein Y is thiazol-2-yl, Z is 1-(3,4-difluorophenyl)-1,3-dihydro-3H-benzimidazol-2-on-5-yl, and R is H;
the compound wherein Y is thiazol-2-yl, Z is 1-(4-trifluoromethylphenyl)-1,3-dihydro-3H-benzimidazol-2-on-5-yl, and R is H;

the compound wherein Y is thiazol-2-yl, Z is 1-(3,3,3-trifluoropropyl)-1,3-dihydro-3H-benzimidazol-2-on-5-yl, and R is H;

the compound wherein Y is thiazol-2-yl, Z is 1-(4,4-difluorocyclohexyl)-1,3-dihydro-3H-benzimidazol-2-on-5-yl, and R is H;

and pharmaceutically acceptable salt forms thereof.

11. A pharmaceutical composition comprising the compound of claim 1 or 10 and a member selected from the group consisting of a pharmaceutically acceptable carrier, a pharmaceutically acceptable excipient, and a pharmaceutically acceptable diluent.

12. A pharmaceutical composition of claim 11, wherein the composition is a solid oral dosage form.

13. A pharmaceutical composition of claim 11, wherein the composition is selected from the group consisting of a syrup, an elixir, and a suspension.

14. A method for treating inflammatory pain in a subject in need thereof comprising administering a therapeutically effective amount of the compound of claim 1 or 10 to the subject.

15. The method of claim 14 wherein the inflammatory pain is due to inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain, pain due to physical trauma, headache, sinus headache, tension headache, or arachnoiditis.

16. A compound that is Formula 1g

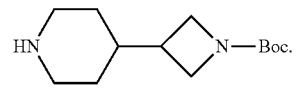

1g

* * * * *